(12) United States Patent
Lincoln

(10) Patent No.: US 12,295,800 B2
(45) Date of Patent: May 13, 2025

(54) ARCH PREPARATION SYSTEM AND METHOD FOR RECEIVING A FULL ARCH DENTAL RESTORATION DEVICE

(71) Applicant: TruBridge Dental L.L.C., Bainbridge Island, WA (US)

(72) Inventor: Helena Soomer Lincoln, Bainbridge Island, WA (US)

(73) Assignee: TruBridge Dental L.L.C., Bainbridge Island, WA (US)

( * ) Notice: Subject to any disclaimer, the term of this patent is extended or adjusted under 35 U.S.C. 154(b) by 0 days.

(21) Appl. No.: 18/632,185

(22) Filed: Apr. 10, 2024

(65) Prior Publication Data

US 2024/0252278 A1    Aug. 1, 2024

Related U.S. Application Data

(63) Continuation-in-part of application No. 18/593,793, filed on Mar. 1, 2024, which is a continuation-in-part of application No. 18/162,497, filed on Jan. 31, 2023.

(Continued)

(51) Int. Cl.
    *A61C 8/00*    (2006.01)
    *A61C 1/08*    (2006.01)

(52) U.S. Cl.
    CPC ............ *A61C 1/084* (2013.01); *A61C 8/0095* (2013.01)

(58) Field of Classification Search
    CPC .............................. A61C 1/084; A61C 8/0095
    See application file for complete search history.

(56) References Cited

U.S. PATENT DOCUMENTS 5,725,376 A * 3/1998 Poirier ................. A61C 9/0053
                                                                433/172
8,231,386 B2    7/2012 Hertz
(Continued)

FOREIGN PATENT DOCUMENTS

EP          3067012 A1    9/2016
JP       2017176486 A    10/2017

OTHER PUBLICATIONS

Office Action issued Apr. 26, 2024 for U.S. Appl. No. 18/162,497, filed Jan. 1, 2023. 26 pages.

(Continued)

*Primary Examiner* — Ralph A Lewis
(74) *Attorney, Agent, or Firm* — Christensen O'Connor Johnson Kindness PLLC

(57) ABSTRACT

A surgical guide for placing implants in a patient's replacement arch to support a teeth-only, gingiva-free, full-arch dental restoration device may include a surgical guide body configured to temporarily, securely mate with teeth and/or gums of a patient's replacement arch and surgical guide sleeves received in the body for guiding implant placement into a corresponding number of post-extraction root sockets of the replacement arch when the surgical guide body is mated with the teeth and/or gums, wherein each surgical guide sleeve is configured to substantially align a longitudinal axis of an implant with an axis of the corresponding post-extraction root socket, and wherein each surgical guide sleeve is configured to limit a depth of an implant within the corresponding post-extraction root socket such that a collar of the implant is generally above the outer cortex layer of the bone at least partially in the gingiva layer.

6 Claims, 44 Drawing Sheets

Related U.S. Application Data

(60) Provisional application No. 63/378,759, filed on Oct. 7, 2022.

(56) References Cited

U.S. PATENT DOCUMENTS

| | | | | |
|---|---|---|---|---|
| 8,992,222 | B2 | 3/2015 | Cottrell | |
| 9,597,160 | B1 | 3/2017 | Gregg, II | |
| 9,730,771 | B2 | 8/2017 | Westover | |
| 10,238,471 | B2* | 3/2019 | Chan | A61C 8/0057 |
| 12,133,779 | B2* | 11/2024 | Lincoln | A61C 8/0095 |
| 2003/0232308 | A1* | 12/2003 | Simmons, Jr. | A61C 8/0031 |
| | | | | 433/173 |
| 2005/0037320 | A1* | 2/2005 | Poirier | A61C 1/084 |
| | | | | 433/76 |
| 2006/0141419 | A1 | 6/2006 | Heo | |
| 2007/0042315 | A1 | 2/2007 | Boutossov | |
| 2010/0304332 | A1 | 12/2010 | Benzon | |
| 2010/0304335 | A1 | 12/2010 | Garcia et al. | |
| 2012/0251974 | A1* | 10/2012 | Katz | A61C 8/0089 |
| | | | | 433/174 |
| 2014/0038134 | A1* | 2/2014 | Nguyen | A61C 8/0089 |
| | | | | 433/175 |
| 2014/0212843 | A1* | 7/2014 | Chiu | A61C 8/0036 |
| | | | | 433/201.1 |
| 2016/0166363 | A1* | 6/2016 | Varsano | A61C 8/0018 |
| | | | | 703/1 |
| 2021/0015584 | A1 | 1/2021 | Gregg, II | |
| 2021/0128280 | A1 | 5/2021 | Gregg, II | |
| 2021/0205051 | A1 | 7/2021 | De Clerck | |
| 2021/0220093 | A1* | 7/2021 | Sato | A61C 8/0095 |
| 2022/0061966 | A1* | 3/2022 | Hafele | A61C 13/10 |
| 2024/0115363 | A1* | 4/2024 | Lincoln | A61C 8/0048 |
| 2024/0115364 | A1* | 4/2024 | Lincoln | A61C 13/097 |
| 2024/0130840 | A1* | 4/2024 | Lincoln | A61C 13/26 |
| 2024/0197439 | A1* | 6/2024 | Lincoln | A61C 8/0048 |
| 2024/0252278 | A1* | 8/2024 | Lincoln | A61C 8/0095 |

OTHER PUBLICATIONS

Lopez-Jarana, P. et al. "Thickness of the buccal bone wall and root angulation in the maxilla and mandible: an approach to cone beam computed tomography." BMC Oral Health. (2018) 18:194. https://doi.org/10.1186/s12903-018-0652-x. 9 pages.

Pozzi, A. et al. "The Implant Biologic Pontic Designed Interface: Description of the Technique and Cone-Beam Computed Tomography Evaluation." Clinical Implant Dentistry and Related Research, vol. 17, Supp. 2, 2015. 10 pages.

Blanchet, E., et al., "An Image-Guided System Based on Custom Templates: Case Reports", Clinical Implant Dentistry and Related Research 6(1):40-47, Oct. 2006.

International Search Report and Written Opinion mailed Jan. 30, 2024, issued in corresponding International Patent Application No. PCT/US2023/076007, filed Oct. 4, 2023, 22 pages.

Pozzi, A., et al., "Clinical and Radiological Outcomes of Two Implants with Different Prosthetic Interfaces and Neck Configurations: Randomized, Controlled, Split-Mouth Clinical Trial," Clinical Implant Dentistry and Related Research 16(1): 96-106, Feb. 2014.

Pozzi, A., et al., "Clinical Reliability of CAD/CAM Cross-Arch Zirconia Bridges on Immediately Loaded Implants Placed With Computer-Assisted/Template-Guided Surgery: A Retrospective Study With a Follow-Up Between 3 and 5 Years", Clinical Implant Dentistry and Related Research, vol. 17, Supplement 1, pp. e86-e96, Jan. 2015.

Pozzi, A., et al., "Monolithic Lithium Disilicate Full-Contour Crowns Bonded on CAD/CAM Zirconia Complete-Arch Implant Bridges With 3 to 5 Years of Follow-Up", Journal of Oral Implantology vol. XLI(4), pp. 450-458, Aug. 2015.

Article by Dr. Siri P.B., Dentist Channel Online, "Forceps in Dental Extraction—Classification, Working principle and Design". Sep. 25, 2021. Accessed via https://dentistchannel.online/forceps-in-dental-extraction-classification-working-principle-and-design/article?for=people> on Feb. 6, 2024 (Year: 2021).

Atcha, I., "3 Approaches to Placing Implants After Tooth Extractions", Aug. 6, 2021. Accessed via <https://newteethchicagodentalimplants.com/3-approaches-to-placing-implants-after-tooth-extractions/> (Year: 2021).

Bhardwaj Dental Clinic, How Does Laser Tooth Extraction Work, https:bhardwajdentalclinic.com/2021/12/how-does-laser-tooth-extraction-work/ (Dec. 3, 2021) (Year: 2021.

Kaufman, Z., and K.S. Parenhos, "Digitally Designed Ovate Pontic as a Predictable Procedure to Improve Accuracy, Hygiene, Esthetics", Compendium of Continuing Education in Dentistry, 43(4):226-230, Apr. 2022.

* cited by examiner

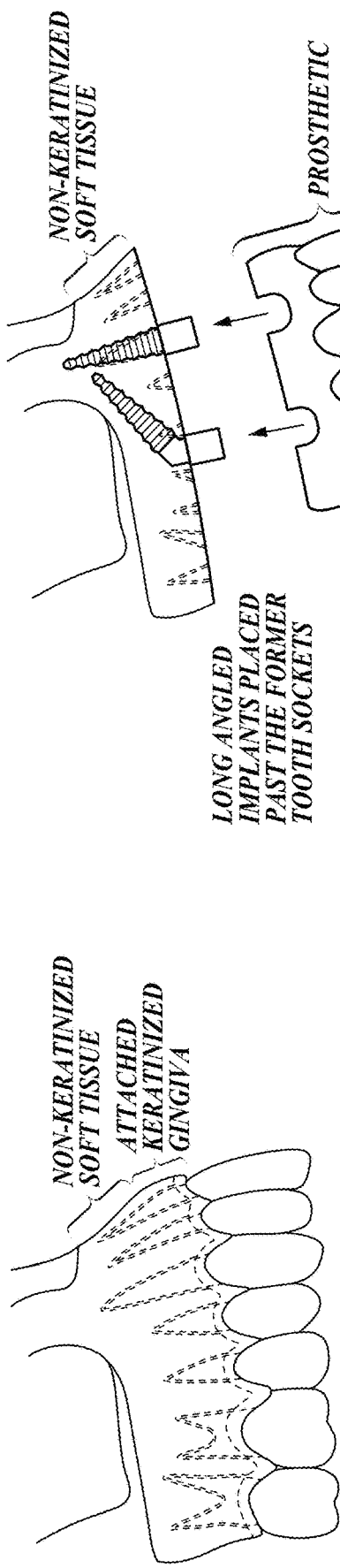
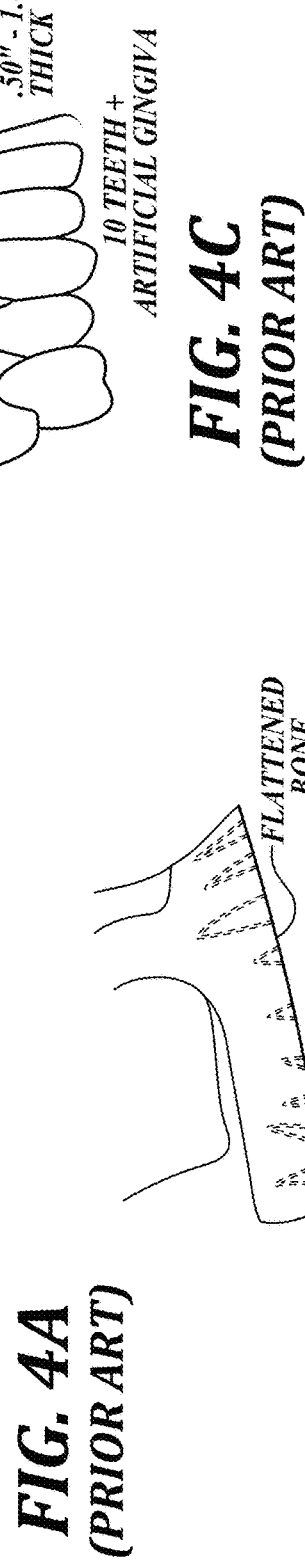
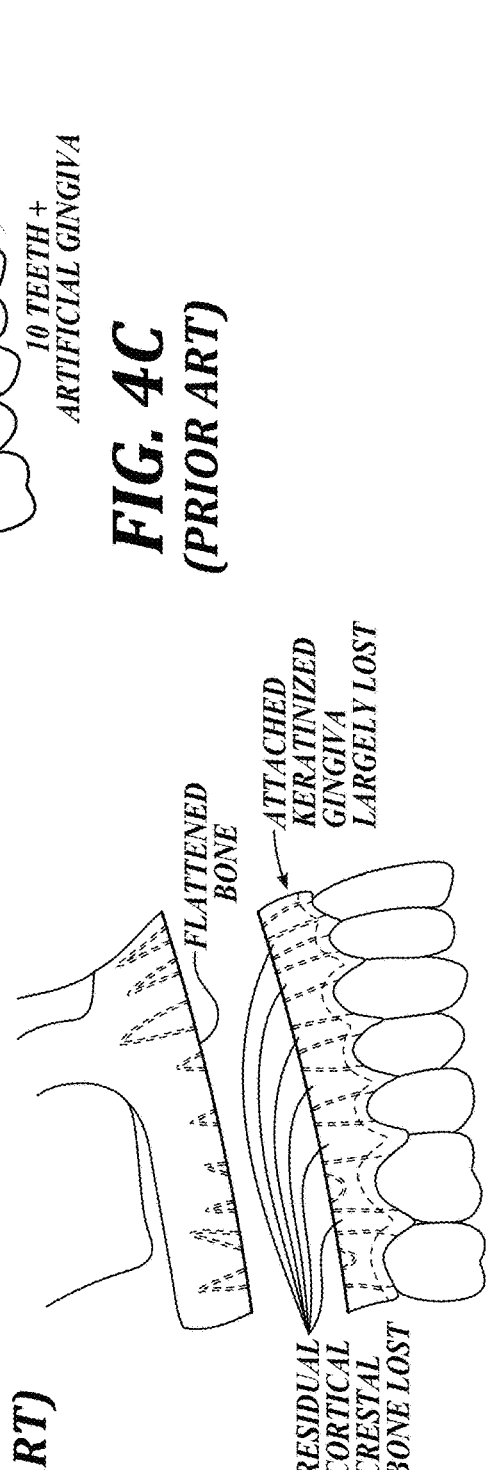
FIG. 4A (PRIOR ART)
FIG. 4B (PRIOR ART)
FIG. 4C (PRIOR ART)

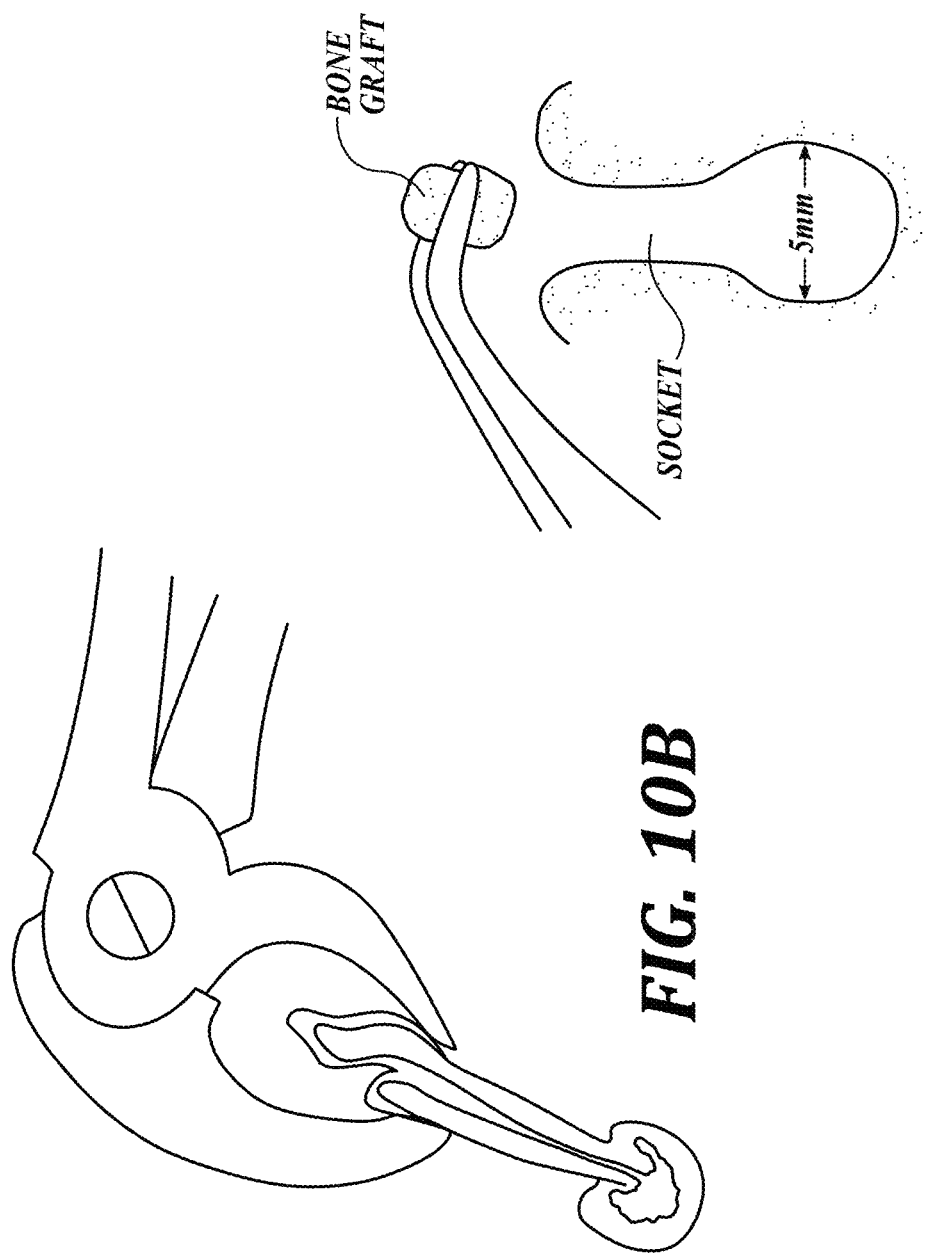
FIG. 10C
FIG. 10B
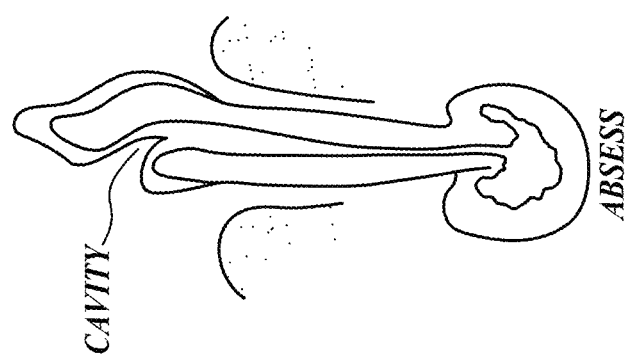
FIG. 10A

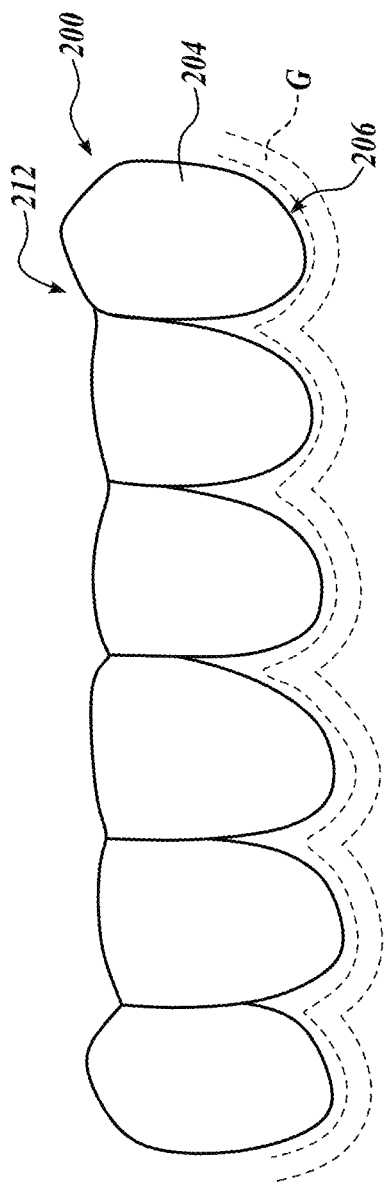
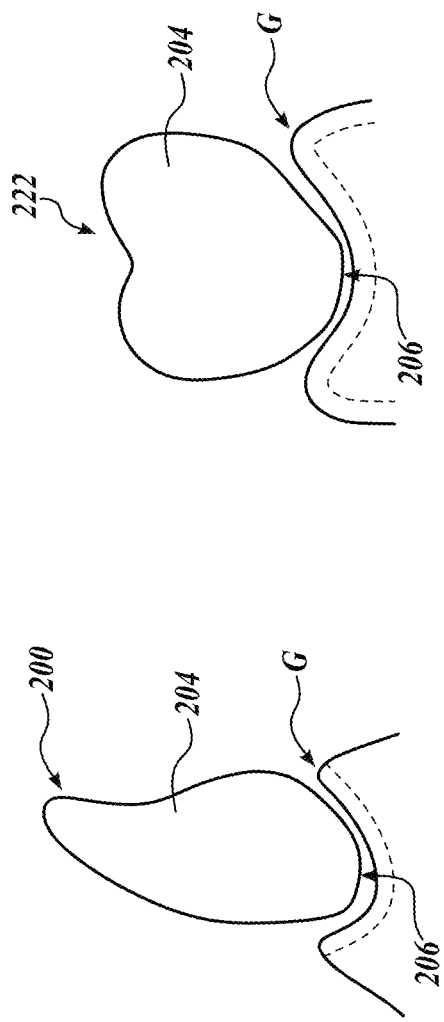
FIG. 19A
FIG. 19B
FIG. 19C

ATRAUMATIC EXTRACTIONS

IMPLANT PLACEMENT INTO FORMER TEETH SOCKETS

ABUTMENTS AND PLACING BRIDGE

ARCH PREPARATION SYSTEM AND METHOD FOR RECEIVING A FULL ARCH DENTAL RESTORATION DEVICE

CROSS-REFERENCES TO RELATED APPLICATIONS

This application is a continuation-in-part of U.S. patent application Ser. No. 18/593,793, filed Mar. 1, 2024, which is a is a continuation-in-part of U.S. patent application Ser. No. 18/162,497, filed Jan. 31, 2023, which claims the benefit of U.S. Provisional Patent Application No. 63/378,759, filed Oct. 7, 2022.

TECHNICAL FIELD

The present disclosure relates to a system and method for preparing a patient's arch for a full mouth (e.g., ten, twelve, or fourteen teeth, upper and/or lower jaw) teeth replacement device.

SUMMARY

In some aspects, the techniques described herein relate to a surgical guide for placing implants in a patient's replacement arch to support a teeth-only, gingiva-free, full-arch dental restoration device, wherein the surgical guide may include: a surgical guide body configured to temporarily, securely mate with at least one of teeth and gums of a patient's replacement arch; and a plurality of surgical guide sleeves received in the body for guiding implant placement into a corresponding number of post-extraction root sockets of the patient's replacement arch when the surgical guide body is mated with the at least one of teeth and gums of a patient's replacement arch, wherein each surgical guide sleeve is configured to substantially align a longitudinal axis of an implant with an axis of the corresponding post-extraction root socket, and wherein each surgical guide sleeve is configured to limit a depth of an implant within the corresponding post-extraction root socket such that a collar of the implant is generally above the outer cortex layer of the bone at least partially in the gingiva layer.

In some aspects, the techniques described herein relate to a method of making a surgical guide for placing implants in a patient's replacement arch to support a teeth-only, gingiva-free, full-arch dental restoration device, wherein the method may include: performing, with a computing device, a tooth socket implant locating step including determining, based on a digital representation of a patient's replacement arch, which of the patient's replacement arch tooth sockets are intended locations of implants for securing a teeth-only, gingiva-free, full-arch dental restoration device to the patient's replacement arch after all original teeth of the patient's replacement arch are extracted; generating, with a computing device, a surgical guide digital design by: performing, with a computing device, a virtual implant placement step including digitally placing each of the implants in a digital representation of the patient' replacement arch; and performing, with a computing device, a surgical guide design step including digitally defining a size and shape of a body of the surgical guide relative to a digital representation of the patient' replacement arch; and outputting, with a computing device, fabrication instructions to a fabrication machine for making a surgical guide based on the surgical guide digital design.

In some aspects, the techniques described herein relate to a method for preparing a patient's replacement arch for a full arch teeth replacement, wherein the method may include: performing, with a computing device, a tooth socket implant locating step including determining, based on a digital representation of the patient's replacement arch, first, second, third, and fourth tooth sockets of the patient's replacement arch that are intended locations of first, second, third, and fourth implants, respectively, for securing a teeth-only, gingiva-free, full-arch dental restoration device to the patient's replacement arch after all original teeth of the patient's replacement arch are extracted; extracting any teeth in the first, second, third, and fourth tooth sockets of the patient's replacement arch, wherein each tooth is extracted in a manner that substantially maintains the original alveolar bone and original keratinized gingiva of the patient's replacement arch; guiding, with a surgical guide, placement of each of the first, second, third, and fourth implants into the first, second, third, and fourth tooth sockets of the patient's replacement arch, respectively, such that a longitudinal axis of each implant is substantially aligned with an axis of the corresponding tooth socket and a collar of each implant is generally above an outer cortex layer of bone at least partially in a gingiva layer of the corresponding tooth socket; and extracting any remaining teeth of the patient's replacement arch in a manner that substantially maintains the patient's original alveolar bone and original keratinized gingiva of the patient's replacement arch.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative examples, in which the principles of the invention are utilized, and the accompanying drawings of which:

FIGS. 4A-4C depict images providing an overview of the prior art dental restoration technique of FIG. 2.

FIGS. 10A-10C depict a tooth having an abscess being removed, including any diseased tissue defining the abscess.

FIGS. 19A-19C depicts front and side views of portions of a dental bridge shown seated against a ridge/gingiva of a patient's jaw preserved in accordance with exemplary aspects of the pre-prosthetic ridge preservation process of FIG. 9.

DETAILED DESCRIPTION

Systems and methods for preparing a patient for a full arch teeth replacement are disclosed herein.

Figure 1:
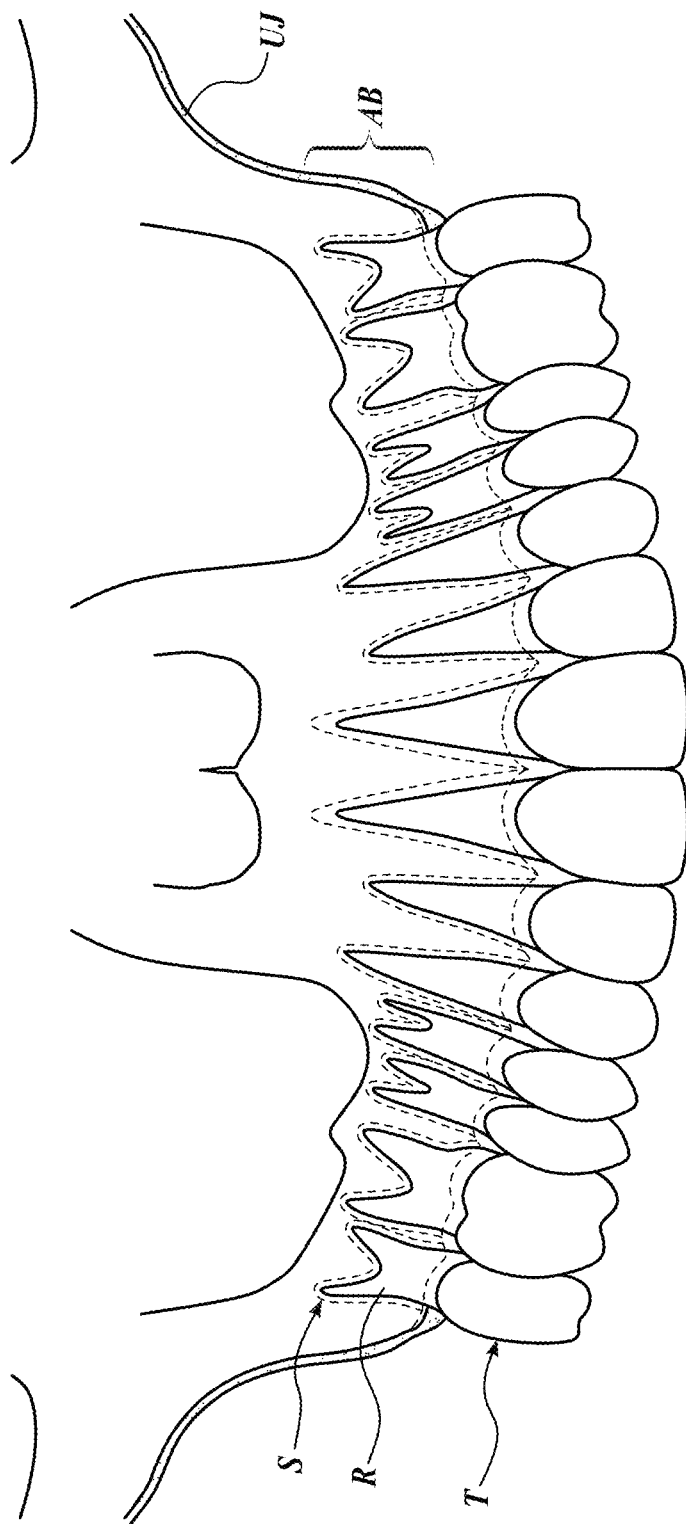
FIG. 1 depicts an image of an exemplary human upper jaw showing fourteen (14) natural teeth each having roots secured within corresponding teeth sockets defined in an upper jawbone.

FIG. 1 depicts an image of an exemplary human upper jaw showing fourteen (14) natural teeth T each having roots R secured within corresponding teeth sockets S defined in an upper jawbone UJ. The portion of the upper jawbone UJ defining the teeth sockets S is called the alveolar bone AB.

Tooth decay can necessitate removal of a diseased part of the tooth and restoration of the same, which is typically an ongoing process. Small restorations (e.g., fillings) can become larger restorations (e.g., crowns or bridges) as the tooth ages. Ultimately, there may be a time when a tooth becomes non-restorable (also sometimes called "non-retainable" or "terminal"). For instance, the tooth may be cracked, a tooth may have decay on the root surface, a tooth may have poor bone support, etc. In such an instance, a dental professional may determine that it is better for the health of the remaining dentition to remove such teeth. In some instances, all or substantially all of the teeth of the upper and/or lower jaw may necessitate replacement, and a full mouth (e.g., 10, 12, or 14-teeth of an upper or lower jaw) teeth replacement is recommended. There are various modalities to replace teeth.

For instance, a dental implant(s) may be secured within a jaw of a patient, and a single tooth, a bridge of teeth, or implant retained dentures are then secured to the dental implant. More specifically, a dental implant, which is a small titanium screw, is positioned into the jawbone to support either a single tooth, a bridge of teeth, or implant retained dentures. In other words, the titanium implant forms the foundation by which the replacement teeth are attached.

For a conventional dental implant procedure, a full arch rehabilitation requires six-to eight (6-8) implants to support a full fixed bridge or implant retained dentures. A limitation of the conventional full arch teeth replacement method arises when screwing the posterior implants into areas of reduced bone density.

An All On 4™ or "Malo bridge" technique as well as other similar prior art techniques has become widely acknowledged as the superior treatment option for a full-arch teeth replacement because only four implants are needed to provide support for the full arch, and the results are instant. Consumers were convinced that this form of treatment for "getting an instant, beautiful smile" was the "clear choice" over other treatment options. Aspects of this prior art treatment, such as the All On 4™ technique, including the full-arch teeth replacement prosthesis used for the technique is shown in FIGS. 2-8.

Figure 2:
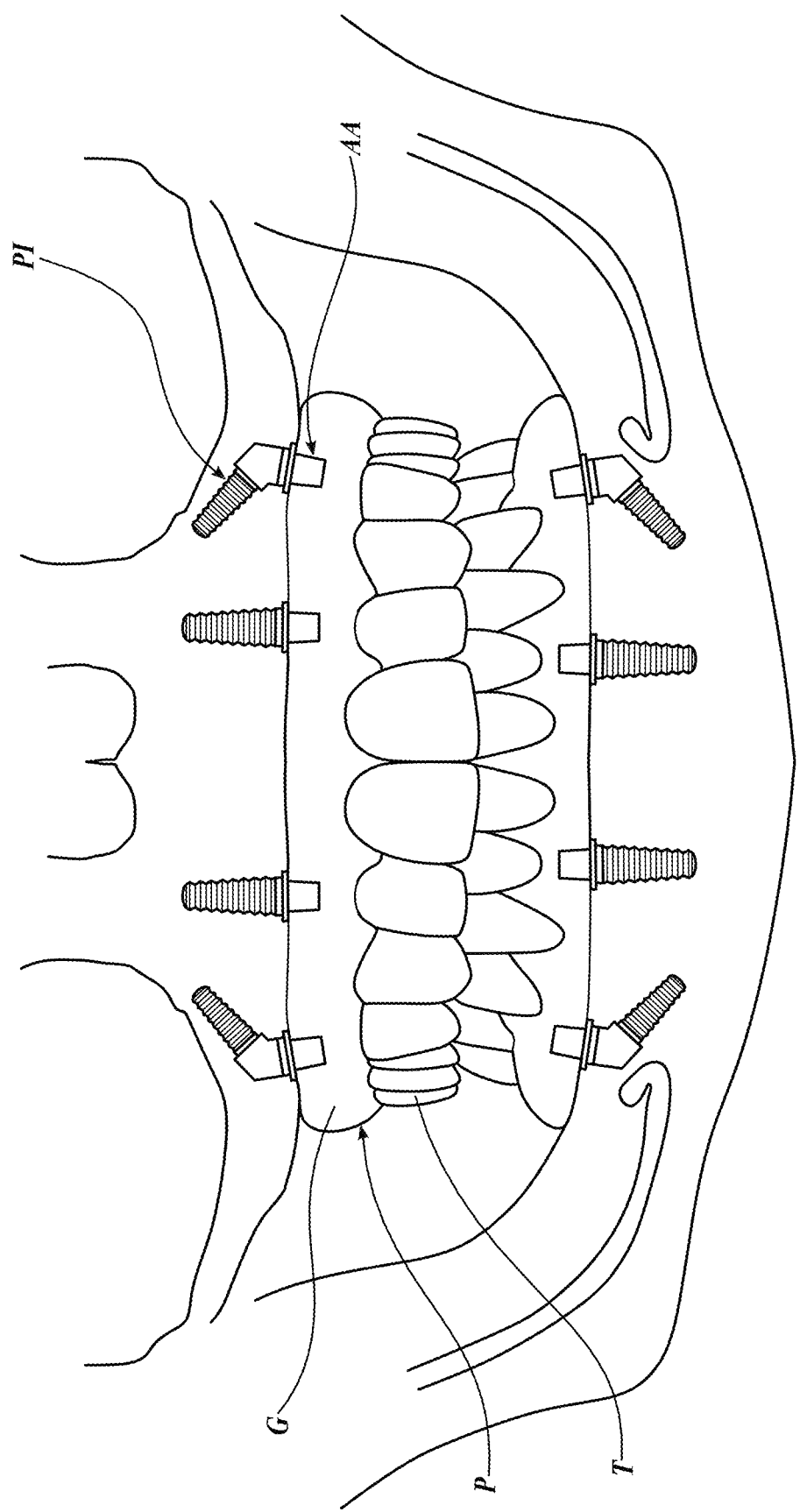
FIG. 2 depicts a front view of an exemplary prior art dental restoration technique, including a full-arch teeth replacement prosthesis having artificial gingiva and teeth secured to angulated implants with angulated abutments.
Figure 3:
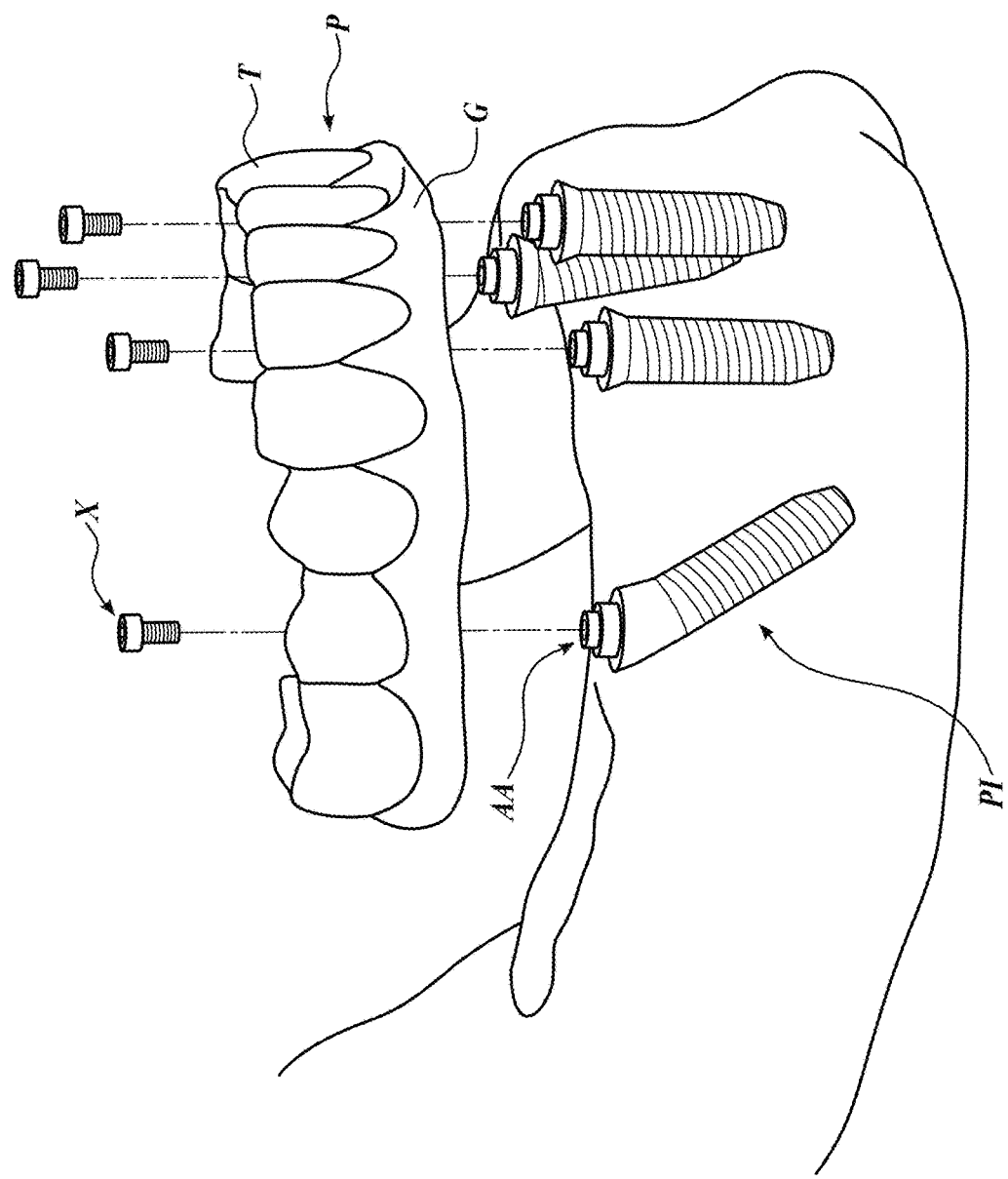
FIG. 3 depicts an isometric view of the prior art dental restoration technique of FIG. 2.

Referring specifically to FIGS. 2 and 3, with the All On 4™ dental implant procedure, the posterior implants PI are tilted 45° towards the rear of the mouth and placed into the anterior maxilla, a region of the jaw with higher bone density. More specifically, long posterior implants PI are inserted at 45-degree angles into the anterior maxilla and mandible, and angled abutments AA (such as multi-unit angulated abutments) are used at the distal end of the posterior implants PI to attach a prior art prosthetic P to the upper and lower jaw. The angled abutments AA are generally at a 45-degree angle relative to the longitudinal axis of the posterior implants PI such that screws X may be inserted transversely through the prosthetic P into the abutment opening.

Compared to other implant methods, the All On 4 technique doesn't require the same density of bone in order to secure the implant. Rather, the introduction of the 45° angulated implant meant that bone-deficient areas of the jaw could be avoided.

For any dental implant procedure, a pre-prosthetic surgery is likely necessary to prepare a patient's mouth before the placement of a prosthesis. For instance, a pre-prosthetic surgery protocol may include smoothing out, reshaping, and/or partially removing the bone surrounding the teeth.

Figure 5:
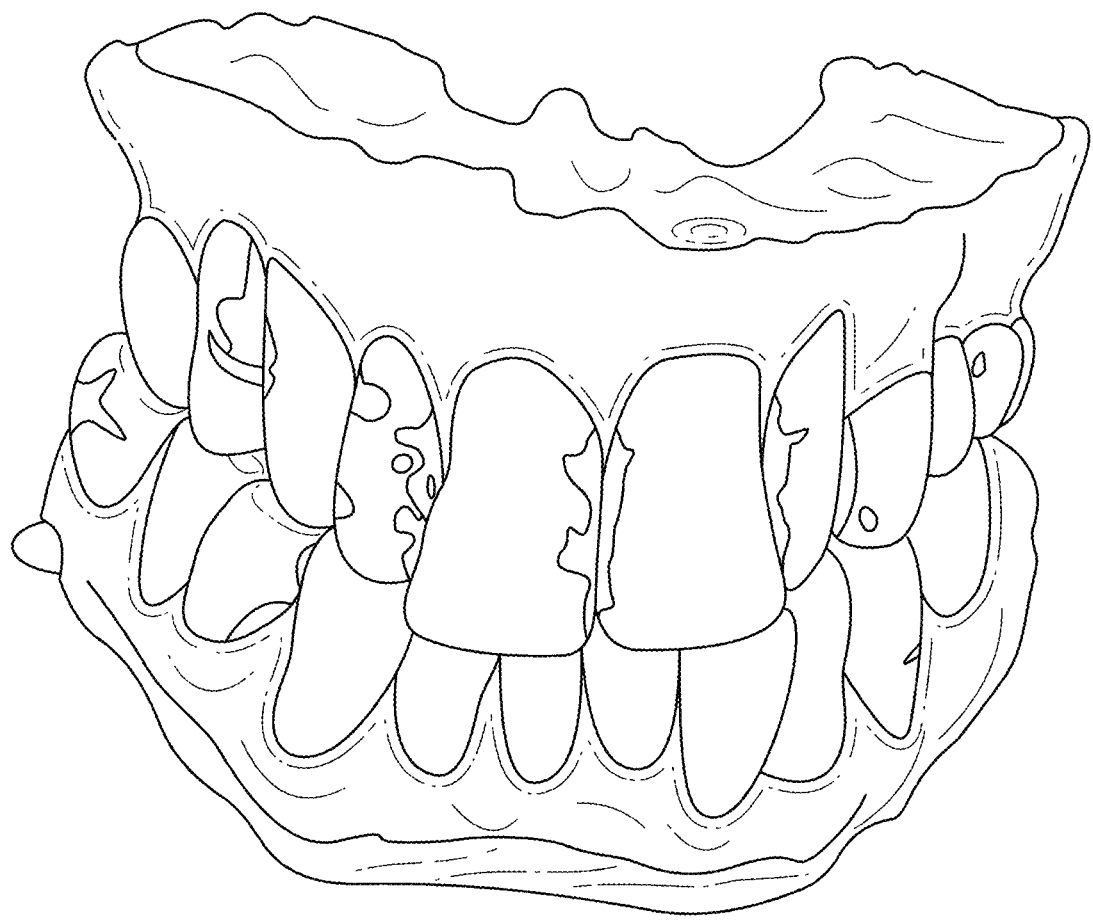
FIGS. 5 and 6 depict photograph images of a patient's teeth and jaw for the upper and lower jaw, respectively, removed using the prior art dental restoration technique of FIG. 2.
Figure 6:
Figure 7:
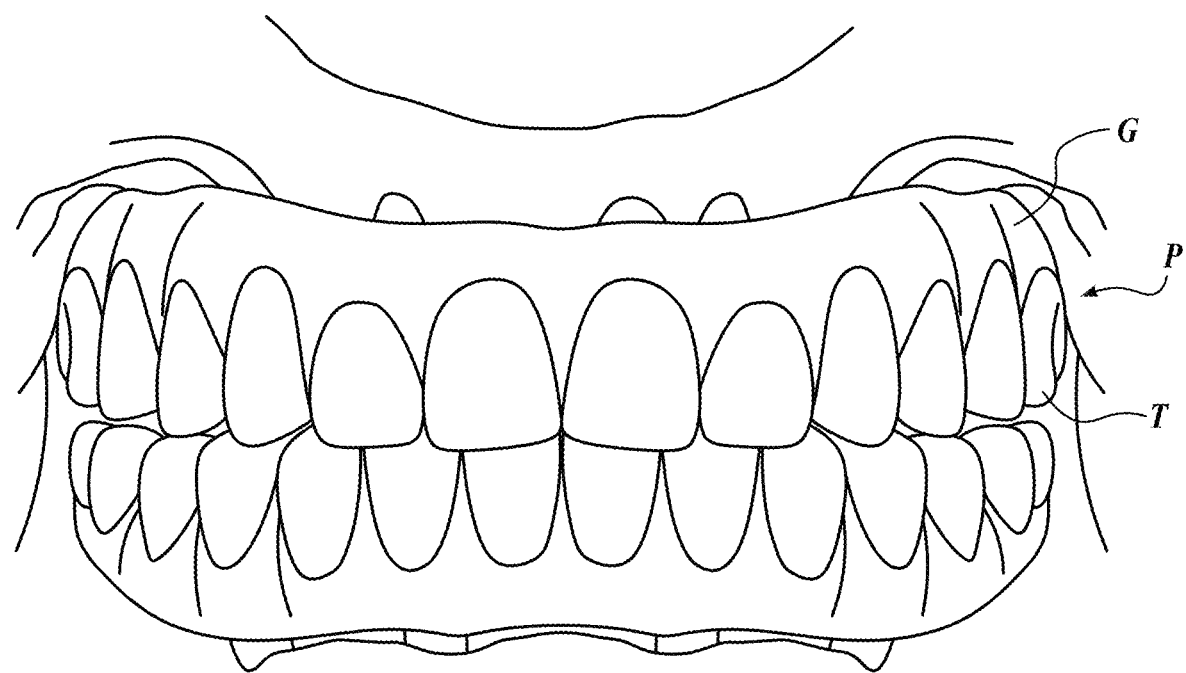
FIG. 7 depicts a photograph image of full-arch teeth replacement prostheses having artificial gingiva and teeth secured to upper and lower jaws of patient.

Referring to FIGS. 4-6, the All On 4™ pre-prosthetic surgery protocol includes removing about one inch of bone (along the height of the jaw) from the maxillary and/or mandibular arches, which includes the alveolar bone that houses the teeth and all of the keratinized gingival tissue KG (i.e., the attached, sturdy tissue that covers the alveolar bone and supports the teeth).

Such a dramatic pre-prosthetic surgery protocol used for the All On 4™ technique is quick compared to smoothing out, reshaping, and/or partially removing the bone surrounding the teeth to accommodate individual teeth, a conventional bridge, etc. The rehabilitation process for the All On 4™ pre-prosthetic surgery is also considerably shorter because the bone does not need to heal to support the new prosthetic. Further, because fewer implant fixtures are used, there is more flexibility to design and fit the optimum replacement teeth compared to conventional full arch teeth replacement or the like. Accordingly, many patients have opted for this "new teeth in a day" procedure.

In instances of a single tooth replacement or a small bridge, the alveolar bone typically houses the implant(s). The All On 4™ technique includes removing the alveolar bone. Accordingly, when using the All On 4™ technique, the posterior implants PI must be drilled into the bone at an angle such that they can be retained within the higher density bone of the anterior maxilla. Angling of the implants is also required in order to avoid anatomical structures, such as a sinus cavity and/or the mandibular nerve, which are located deeper within the jaw bone.

Moreover, with significant portions of the bone removed, the prior art prosthetic P used for the All On 4™ dental implant procedure, which is shown in FIGS. 2-4 and 7, must replace the missing bone and tissue. In that regard, the All On 4™ prior art prosthetic P includes an artificial gum portion AG and artificial teeth AT extending from the gum portion AG. When removing the bone, the maxillary and/or mandibular arches are flattened such that the artificial gum portion AG may be universally designed to generally fit in any patient's mouth. Moreover, a flattened prosthesis interface may easily seat against the jaw for securing to the implant abutments.

The prosthetic P is purposefully made tall (about one-half to one inch tall defined by the height of teeth+the height of the artificial gingiva) and thick to prevent breakage during its use, to hide the transition line from artificial gingiva to patient's natural gingiva, and to provide instant teeth secured to the just-placed implants without a period of healing. However, when so tall and thick, the prosthetic P can include only ten (versus twelve or fourteen) teeth, i.e., the prosthetic P does not usually include the second bicuspid and second molar. If the prosthetic P included all fourteen functional teeth, the prosthetic P would be so large that the patient could not open sufficiently wide to allow for the prosthetic P to be screwed into their jaw.

The design of the prosthetic P includes other drawbacks. For instance, the prosthetic P does not seat with the patient's gum line in a way that teeth naturally do, which makes it very difficult to clean underneath the prosthetic, often leading to chronic tissue irritation and inflammation. Moreover, a tall and thick prosthetic such as the All On 4™ prosthetic P causes speech difficulties, such as in the form of lisping from the gap that forms between the prosthetic and the patient's natural gums. Further, despite being tall and thick, breakage still frequently occurs.

As a further issue, the long-angled implants are placed in the jawbone past the former tooth sockets, into the native bone that is naturally not meant to house roots or implants. Moreover, implants that are at sharp angles and abrupt transitions like the 45-degree angle implants used with the All On 4™ procedure are un-natural to the body and often cause soft tissue irritation and inflammation. Moreover, if the underlying implants fail, the patient cannot later decide to use a different type of prosthetic because the bone and gum has already been permanently removed.

Accordingly, it can be appreciated that the quick teeth replacement fix provided by the All On 4™ procedure or similar procedures has major drawbacks.

Systems and methods disclosed herein are directed to a full arch dental restoration device arch preparation system and method. The arch preparation system and method disclosed herein prepares a patient's arch for receiving a unique dental restoration device that can support a full mouth teeth replacement (e.g., 10 to 14 teeth) while using a minimal number of straight or non-angulated implants (e.g., four non-angulated implants) and while preserving a patient's bone and natural gum line to provide a natural teeth feel and look. In that regard, the exemplary dental restoration device described herein avoids excessive bone removal and a large prosthetic that leads to issues with speech and cleanability. Rather, the exemplary dental restoration device is free of artificial gingiva and includes only artificial teeth that seat against a patient's natural gum line.

Examples of a dental restoration device described herein are generally configured as a dental bridge and will generally hereinafter be referenced as such. However, it should be noted that the dental restoration device may instead be considered to be any other suitable dental restoration device, such as an implant-based denture, a prosthetic, etc. Accordingly, the use of the term "bridge" should not be seen as limiting.

The dental restoration device described herein may be configured as a full arch dental bridge for replacing all the teeth in the upper or lower arch of a patient. In some cases, both an upper and lower arch will need to be replaced. In other cases, only one of the arches needs to be replaced. In any event, the arch designated for replacement with a full arch, teeth-only bridge described herein is a "replacement arch" of the patient, regardless of whether it is the upper or lower arch. The other of the upper or lower arch that is not designated for replacement is considered the antagonist (opposite) arch, regardless of whether it includes original teeth (including crowns, partial bridges, dental implants, prosthetics, dentures, etc.) or a full arch, teeth-only bridge in accordance with examples described herein.

A dental restoration device or bridge formed in accordance with examples of the disclosure can be placed on a patient's replacement arch (using socket sized, non-angulated implants) following the use of a full arch dental restoration device arch preparation system and method, as described herein. The full arch dental restoration device arch preparation system and method may incorporate aspects of a preliminary bridge design process. The full arch dental restoration device arch preparation system and method may also incorporate a pre-prosthetic ridge preservation process, which includes performing atraumatic dental extractions and preserving the original tooth sockets to prepare a patient's mouth for bridge placement. The full arch dental restoration device arch preparation system and method may also incorporate a design and use of a surgical guide configured to aid in implant placement.

An overview of the dental restoration device and the full arch dental restoration device arch preparation system and method formed in accordance with examples of the disclosure will first be described with respect to FIGS. 8 and 9.

Figure 8:
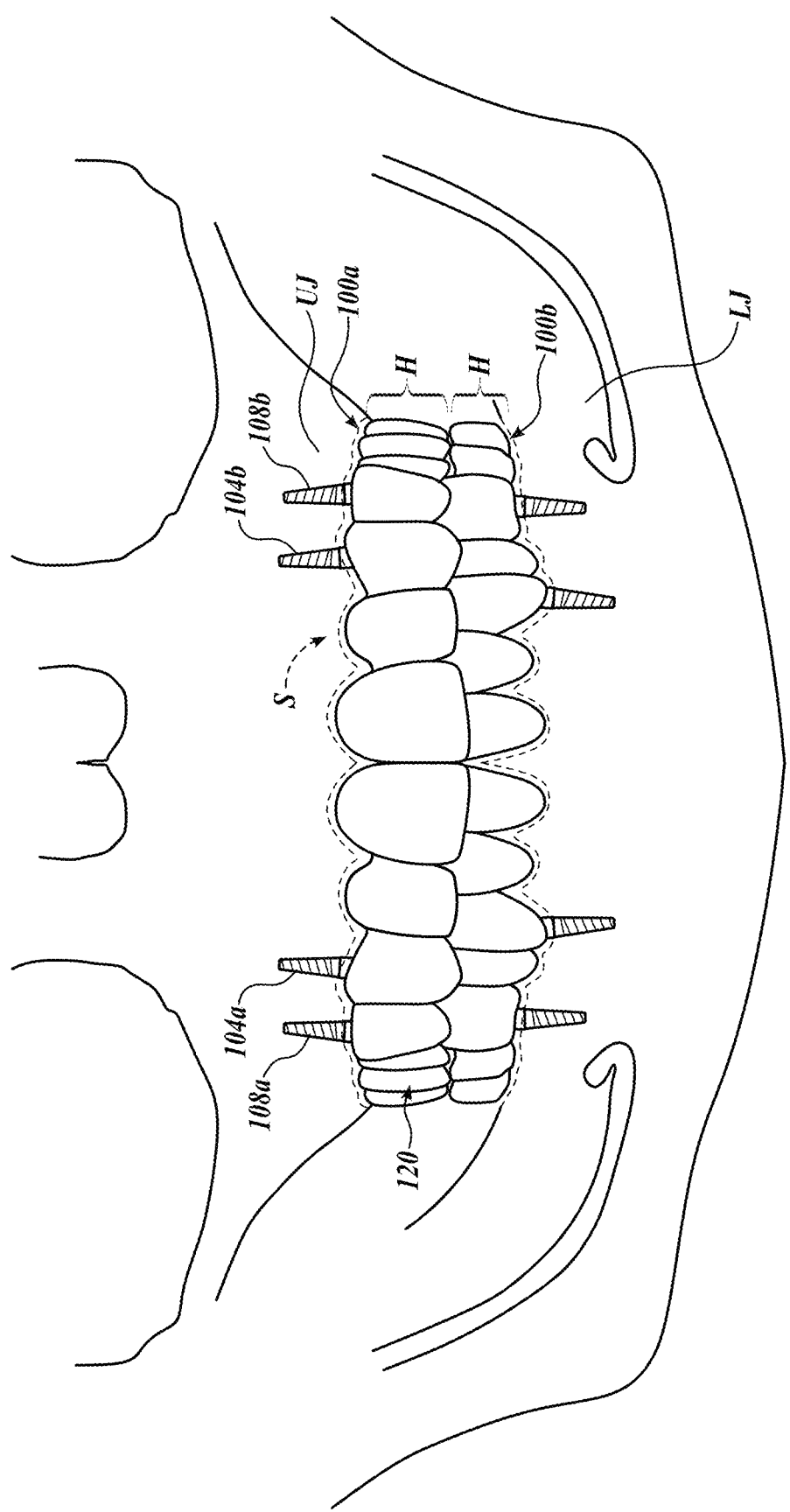
FIG. 8 depicts a front view of examples of first and second dental restoration devices secured to upper and lower jaws, respectively, of a patient, using the systems and described herein.

Referring first to FIG. 8, exemplary aspects of a dental restoration device are shown. More particularly, a first dental restoration device is shown as a first dental bridge 100*a* for an upper jaw and a second dental restoration device is shown as second dental bridge 100*b* for a lower jaw. The first and second dental bridges 100*a* and 100*b* may hereinafter be simply referred to as "dental bridge 100" for simplicity.

The dental bridge 100 is generally a full-arch teeth replacement device for an upper or lower jaw that is without artificial gingiva (e.g., includes only artificial teeth), that can seal or seat against a patient's natural gum line, and that can attach to non-angulated, socket-based implants. The dental bridge 100 is denoted as "full arch" because it is generally designed to include the same number of teeth as the patient's original arch, such as fourteen teeth, twelve teeth, or ten teeth. In some instances, the dental bridge 100 may have less teeth than the original arch if needed for dental/medical reasons. For instance, if a patient's original arch included significant crowding, the bridge may be designed to include fewer teeth to better accommodate the size of the patient's jaw. In any case, the dental bridge 100 is considered a full arch bridge device in that fewer teeth are not needed for the bridge to fit within a patient's mouth, as in the prior art method (see FIG. 4C where the prosthetic includes only ten teeth, whereas the patient originally had fourteen teeth, as shown in FIG. 4A).

The dental bridge 100 includes a light-weight body made from zirconia or a similarly strong, non-porous (e.g., non-staining), hygienic material to provide the strength of natural teeth. The body extends between a gingival side and an occlusal/incisal side and includes a plurality of integrally formed teeth portions each having a tooth axis extending between the gingival side and the occlusal/incisal side that is offset from vertical.

The dental bridge 100 defines an ovate bridge/gingival interface for each tooth portion on the gingival side of the body. The ovate design on the gingival side of the body enables the bridge to seat (e.g., seal) against a patient's upper or lower gums, which are left intact during the pre-prosthetic ridge preservation process. In that regard, the dental bridge 100 is custom-made to fit the unique shape and contours of the patient's gum line defined by the preserved tooth sockets, giving the replacement teeth a natural look and feel. Moreover, when seated against a patient's gums, the height H of the body of the dental bridge 100 is about one-eight inch in height (⅛"), compared to the prosthetic P shown in FIGS. 2-4 that is about one-half to one inch in height (½"-1").

The dental bridge 100 is secured to the upper or lower jaw UJ or LJ with the use of tooth-sized, non-angulated implants placed into tooth sockets S that are preserved, for instance, using the pre-prosthetic ridge preservation process. Tooth or socket sized implants are placed into a necessary number of sockets, such as four sockets for a full mouth replacement. In the example shown in FIG. 8, for the upper jaw UJ on a first side, an anterior tooth-sized implant 104*a* is secured in the canine tooth socket, and a posterior tooth-sized implant 108*a* is secured in the first molar tooth socket. Similarly, an anterior tooth-sized implant 104*b* is secured in the canine tooth socket on a second side of the upper jaw UJ, and a posterior tooth-sized implant 108*b* is secured in the first molar tooth socket on the second side of the upper jaw UJ.

A similar implant arrangement may be used for the lower jaw LJ (not separately labeled).

Tooth-sized (non-angulated) implants can be used in the posterior region of the jaw (e.g., the first molar tooth socket) because the implants can be secured in the alveolar bone of the patient, which is substantially preserved during the pre-prosthetic ridge preservation process or a similar process. In other words, angulated implants, as used in the prior art method, are not necessary because sufficient posterior jawbone density is preserved (i.e., it is not removed during the pre-prosthetic surgery as in the prior art method).

As noted above, anterior and posterior non-angulated tooth-sized implants 104a, 104b and 108a, 108b may be used to secure the dental bridge 100 to the upper or lower jaw UJ or LJ. In that regard, the body of the dental bridge 100 includes a corresponding number of abutment holes extending through respective teeth portions of the body from the gingival side to the occlusal/incisal side. Because only a minimal number of implants are required, in most instances, each tooth portion having an abutment hole is located adjacent to a tooth portion without an abutment hole.

Each of the abutment holes is configured to receive a corresponding abutment for mating with an implant. In that regard, each of the abutment holes includes a longitudinal axis that is substantially coaxially aligned with the tooth axis of the respective teeth portion of the bridge 100, which is substantially coaxially aligned with the implant axis. As will become appreciated from the description below, alignment of the abutment holes with the teeth axis allows for the bridge 100 to be secured to corresponding non-angulated implants that are placed in the preserved tooth sockets.

Figures 9A, 9B, 9C:
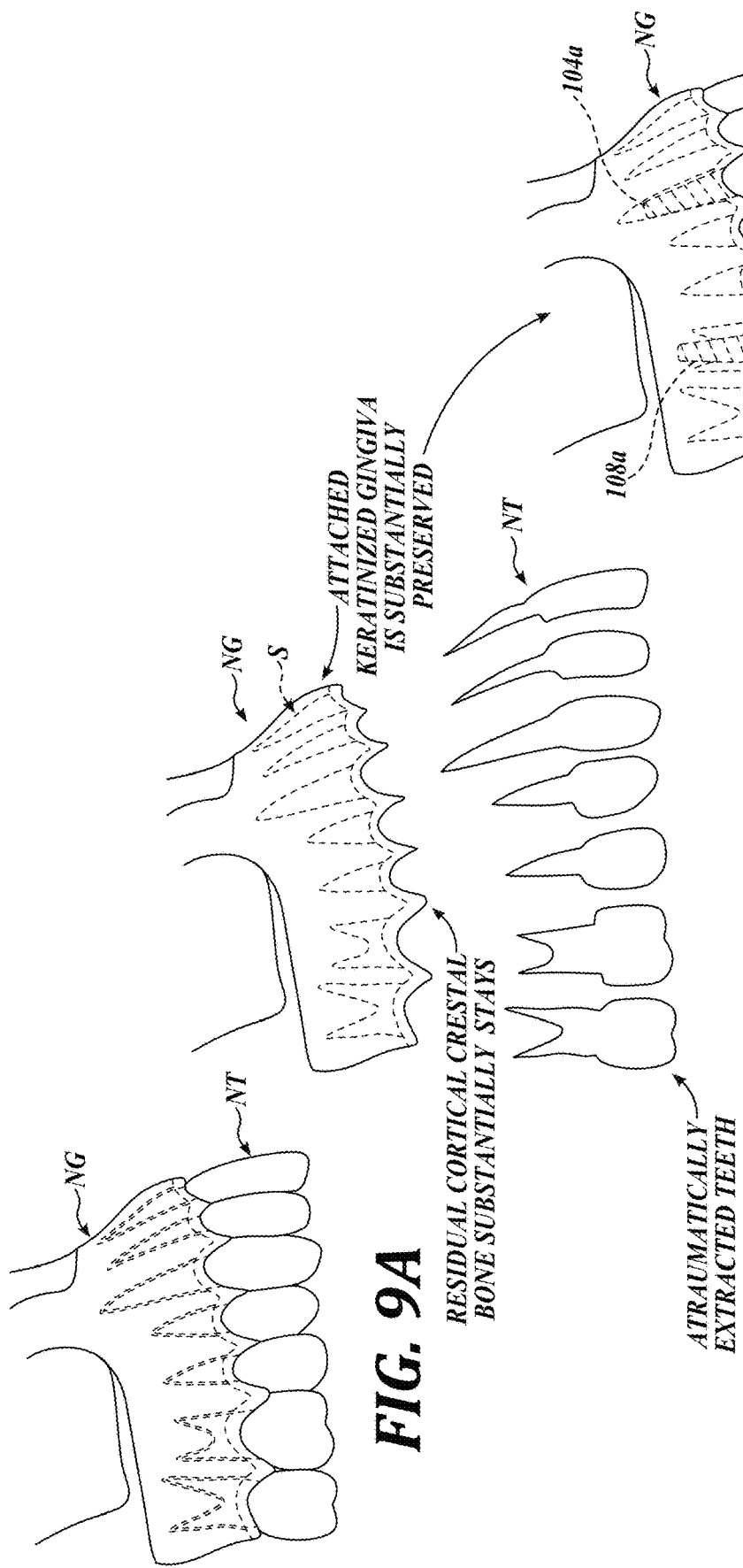
FIGS. 9A-9C depict an overview of a pre-prosthetic ridge preservation process and a dental restoration device (or simply a "dental bridge") formed in accordance with examples of the disclosure will first be described.

Referring now briefly to FIG. 9, an overview of the full arch dental restoration device arch preparation system and method will now be described. As noted above, the full arch dental restoration device arch preparation system and method may incorporate aspects of a preliminary bridge design process, a pre-prosthetic ridge preservation process, and a design and use of a surgical guide.

A preliminary bridge design process may include using foresight, such as with visualization of a final bridge design and/or visualization of bridge design steps to determine a strategy for performing at least one of the pre-prosthetic ridge preservation process and a design and use of a surgical guide. Foresight of bridge design may be based on techniques, know-how, learnings, etc., of a process used to design a dental bridge 100. For instance, foresight may be based on the systems and methods described in U.S. application Ser. No. 18/631,602, entitled "System and Method for Full Arch, Teeth-Only Bridge Design", filed Apr. 10, 2024, the entire disclosure of which is hereby incorporated herein.

As described in U.S. application Ser. No. 18/631,602, a design process for a dental bridge 100 may include capturing scan data of a patient's replacement arch, receiving a model of the replacement arch of the patient generated from the scan data, generating a model of a bridge having individual replacement teeth portions, each individual replacement tooth portion having a tooth axis extending between a gingival section and an incisal/occlusal section of the tooth portion, designating individual replacement teeth portions to include abutment holes based on a location of corresponding implants secured within post-extraction tooth sockets, modifying at least one of a location, shape, and size of one or more of the teeth portions, and outputting information regarding the model of the bridge for fabricating the bridge.

The preliminary bridge design process may include using foresight, such as with visualization of a final bridge design and/or visualization of bridge design steps, to at least preliminarily designate a socket for implant placement, define surgical guide use strategy (e.g., determine whether a surgical guide may benefit implant placement), define design aspects of a surgical guide (e.g., type, size, configuration), define aspects of teeth extraction and ridge preservation, etc.

As noted above, the full arch dental restoration device arch preparation system and method may also incorporate aspects of a pre-prosthetic ridge preservation process. The pre-prosthetic ridge preservation process generally includes performing atraumatic dental extractions of each tooth to prepare the patient's jaw for mating with the dental bridge 100. The dental extractions are done atraumatically in a manner that substantially preserves the bone and tissue defining the patient's natural tooth sockets. In other words, the pre-prosthetic ridge preservation process substantially preserves the patient's bone and gum line for seating against the dental bridge 100 in the manner generally described above. The pre-prosthetic ridge preservation process may also include placing implants into the preserved post-extraction tooth sockets, such as manually or with a surgical guide.

Exemplary detailed aspects of the pre-prosthetic ridge preservation process will now be described.

Pre-Prosthetic Ridge Preservation Process

As noted above, the pre-prosthetic ridge preservation process may include performing atraumatic extractions of all the teeth of the upper and/or lower jaw and placing implants into preserved post-extraction tooth sockets.

Atraumatic Extractions

Exemplary aspects of steps for performing atraumatic extractions of all the teeth of the upper and/or lower jaw using the pre-prosthetic ridge preservation process will first be described with reference to FIGS. 8-15. As noted above, the pre-prosthetic ridge preservation process is used to remove the patient's teeth while substantially preserving the patient's bone and gum line to provide the foundation against which the dental bridge may be placed.

Regarding the patient's bone, each tooth is extracted atraumatically to preserve the alveolar bone substantially in its entirety. The alveolar bone, which houses the teeth roots, includes an outer cortex that encloses an inner medulla. The outer cortex is generally a hard, thick, outer bone, and the medulla is a soft, spongy, inner bone. The outer cortex defines a dental inter-radicular ridge, and when extracting the teeth atraumatically using suitable techniques such as those described herein, substantially the full height and width of the patient's original dental inter-radicular ridge is preserved (see FIGS. 9, 14, and 15). In other words, the bone is not substantially clipped or cut down during extraction (as in the prior art methods), and in most instances, no bone is removed. Rather, the integrity of the alveolar bone, including the original dental inter-radicular ridge and the inter-dental and interseptal bone, is substantially maintained in its entirety. Further, all four walls of the post-extraction root socket (e.g., the 360-degree enclosed wall of the socket) are substantially left intact.

Regarding the patient's gum line, the atraumatic extraction of the tooth also preserves the original keratinized gingiva that defines the naturally shaped gingival ridge. During extraction, the gingival cuff surrounding each tooth is gently elevated and substantially undisturbed during tooth extraction and in post-recovery healing. In other words, typically no flap is created, thereby preserving the interdental papilla.

Suitable techniques for extracting a tooth atraumatically to preserve the alveolar bone and the gingiva in accordance with exemplary aspects of the pre-prosthetic ridge preservation process will be described with particular reference to FIGS. 10-13. Generally, suitable techniques for extracting a tooth in accordance with examples herein include assessing each tooth for removal, elevating the gingival cuff surrounding the tooth, and gripping and moving the tooth with a suitable tool to pull the tooth out of the socket.

In an initial step, each tooth may be assessed to determine a patient's overall candidacy for teeth replacement and/or to determine any unique aspects of a tooth that may affect the technique used for tooth removal and/or the expected result of the tooth removal. For instance, an assessment of each tooth may be performed using a cone beam computer tomography scan ("CBCT scan"). The CBCT scan is used to analyze each tooth, including its root system and surrounding alveolar bone structure. An intraoral scan may also be used.

For instance, each tooth may be analyzed to determine if the tooth has a lesion at the apex of the root, for example, an abscess, as shown in FIG. 10A. Such a tooth may be designated as non-restorable and must be removed substantially in its entirety along with the lesion in the bone. FIG. 10B depicts a tooth having an abscess being removed, including any diseased tissue defining the abscess. In some instances, as shown in FIG. 10C, after the socket is cleaned, the defect area may be more than a certain size (e.g., more than 5 mm wide) and the socket may be augmented with a bone graft (e.g., bone graft putty).

Figure 11:
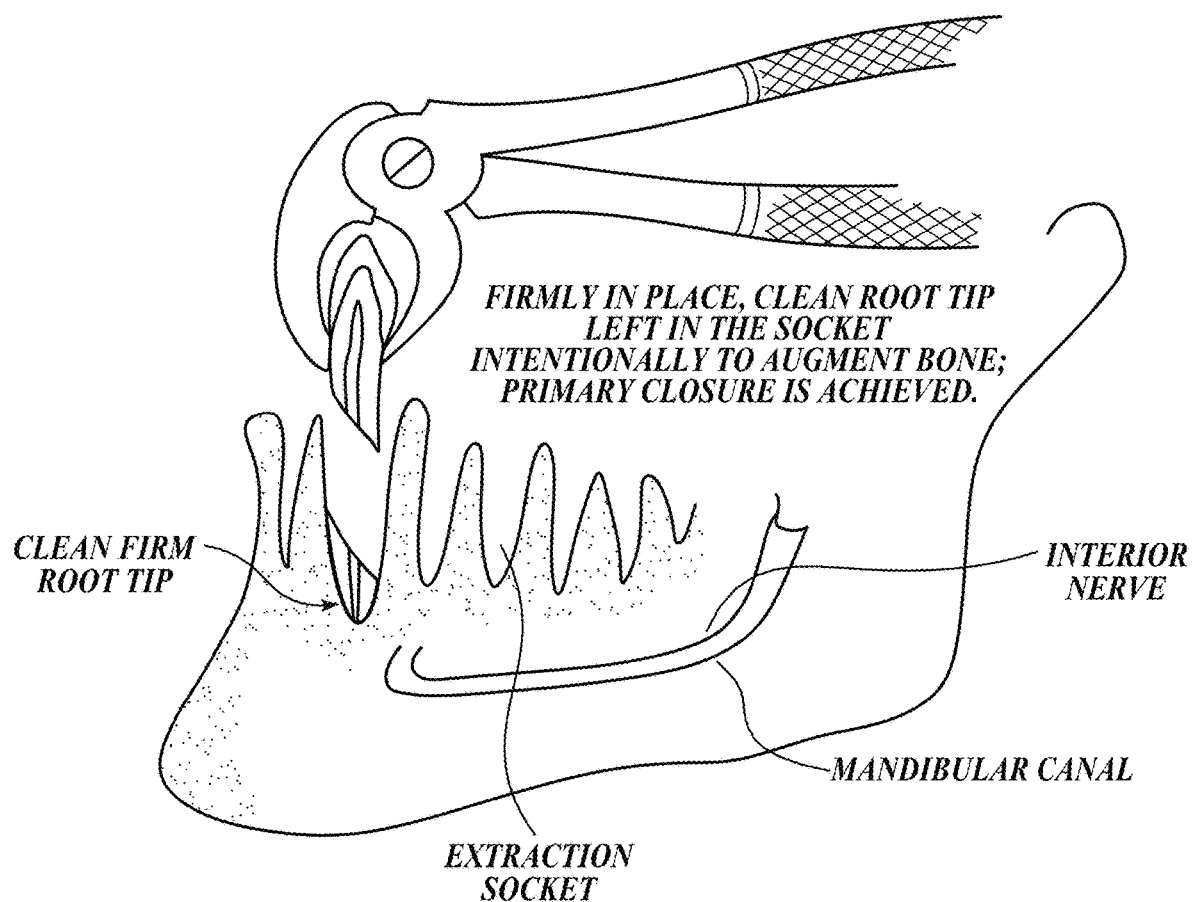
FIG. 11 depicts a tooth having a hooked root tip, wherein the tooth is being extracted and a portion of the root tip is left in the alveolar bone.

Other aspects of the teeth may also be assessed and noted. For instance, a tooth may or may not include a periapical lesion, but a tooth root may have a curve or angulation away from the longitudinal axis of the tooth (e.g., a "hook" in the end of the root). Such a curved or hooked root-tips of can be allowed to remain in the alveolar bone, such as if the root breaks during the extraction, as shown in FIG. 11. In such an instance, the firm root-tip intentionally left in the socket can be cleaned to augment the alveolar bone.

The strategy for each tooth extraction as well as the overall mouth replacement (e.g., whether it makes sense to perform a total mouth replacement) can be assessed in this preliminary step using a CBCT scan or similar. For instance, if a majority of the teeth are designated as non-restorable, the patient may be designated as a candidate for total teeth replacement.

Figure 12A:
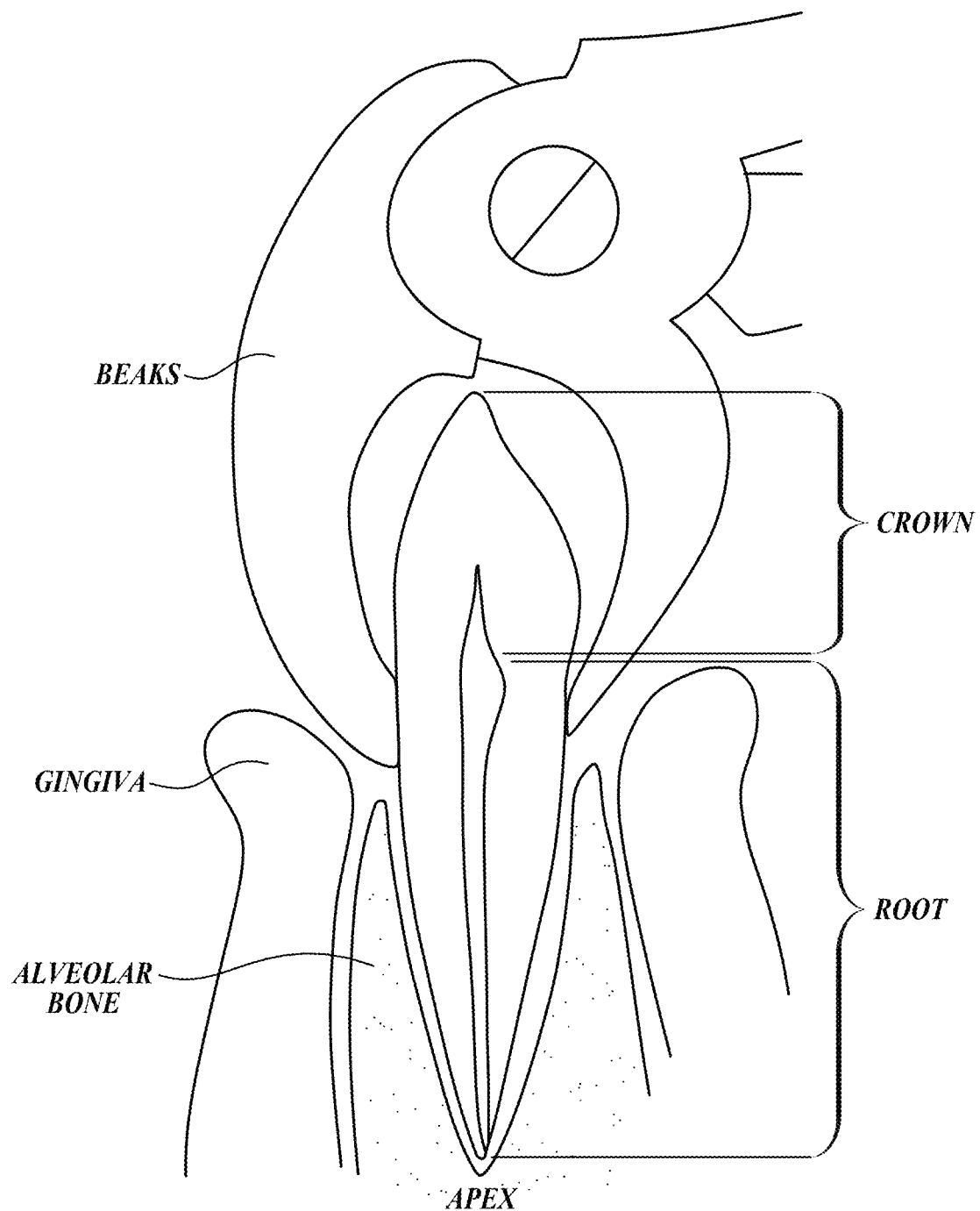
FIGS. 12A-12E depict images showing aspects of an atraumatic tooth extraction in accordance with exemplary aspects of the pre-prosthetic ridge preservation process of FIG. 9.

Referring to FIG. 12A, after an (optional) assessment is performed, the pre-prosthetic ridge preservation process includes extracting teeth atraumatically. Any suitable atraumatic technique may be used, such as a flapless technique. Preferably, the atraumatic tooth extraction process may be performed without fully anesthetizing the patient. Instead, the patient's alveolar ridge (the teeth, gingiva, and alveolar bone) may simply be anesthetized locally. In some aspects, such as in steps using a high-powered laser, local anesthetization can be completely avoided or minimized.

The atraumatic tooth extraction process may include an initial step of gently elevating or relieving the gingival cuff around the tooth (or separating or reflecting the gum tissue from the tooth) to help support atraumatic extraction. The gingival cuff may be generally understood to be the portion of the gums or soft tissue surrounding the upper (coronal) quadrant of the root surface of the tooth. By relieving or otherwise separating the gingival cuff from the tooth, the upper (coronal) quadrant of the root surface of the tooth is exposed and can be accessed by a tooth extraction tool.

Any suitable technique may be used to relieve or otherwise separate the gingival cuff from the tooth. For instance, in one example, the gingival cuff is relieved around the tooth or otherwise substantially separated from the tooth using a scalpel, such as a Lucas's curette or a similar tool. In such an instance, local anesthetization may be used.

In another example, the gingival cuff is relieved around the tooth or otherwise substantially separated from the tooth using light from a high-powered laser. For instance, in one example, a Waterlase iPlus all-tissue laser available from BIOLASE, Inc. of Foothill Ranch, CA may be used. The descriptions provided herein may simply refer to a "laser" or a "high-powered laser", which may include the Waterlase iPlus all-tissue laser or another suitable laser configured for carrying out the functions, steps, etc., described herein.

A high-powered laser such as the Waterlase iPlus all-tissue laser referenced above combines water, air, and laser energy for safe use on human tissue in the mouth. Teeth and tissue are partially made up of water, and when the water stream and beam of energy of the laser contacts the tooth or tissue, it excites the water molecules to cut through the tooth/tissue. In that regard, laser light energy may be directed at the intersection of the gingival cuff tissue and the outer surface of the tooth. The laser energy separates or otherwise peels away the gum tissue from the tooth.

As noted above, a high-powered laser such as the Waterlase iPlus all-tissue laser excites water molecules in the tooth/tissue to cut through the tooth/tissue. While the laser is exciting molecules, a continuous spray of air and water cools the area, so no heat is felt, giving the patient a virtually pain-free or low pain experience. In that regard, the gingival cuff may be elevated around the tooth with a minimal amount of local anesthetization.

Minimizing the use of local anesthetization can significantly decrease the overall procedure time and minimize discomfort to the patient, both during and after the procedure. For instance, the patient can receive less anesthetics by injections or the like, which is uncomfortable during the procedure and can cause post-procedure inflammation, bruising, etc. Thus, use of a high-powered laser, such as the Waterlase iPlus all-tissue laser described herein, supports a more natural, gentle, atraumatic approach to tooth extraction and ridge preservation.

The energy of a high-powered laser can also be used to cauterize the gum tissue as it is separated from the tooth. Cauterization of the newly exposed gum tissue seals off blood vessels to stop, minimize, or otherwise control bleeding. By controlling bleeding, complexity of the atraumatic extraction process is decreased, leading to a shorter and more predictable procedure. In that regard, the laser may be used at various steps associated with or defining part of the dental restoration method described herein to minimize or otherwise control bleeding. For instance, the laser may be used to control bleeding during gingival cuff elevation, extraction, implant placement, tissue removal, etc.

A high-powered laser also has bactericidal properties. For instance, laser energy can provide an ionized oxygen layer in the treated area, such as in the gingival sulcus. The ionized oxygen layer is known to be substantially inhospitable to bacteria. As a result, when using a laser to elevate the gingival cuff, remove bone, or treat other areas of the patient's gums when performing the dental restoration method, substantially any bacteria in the treated area can be killed. In that regard, the laser may be used to help disinfect any areas in the gum tissue, around the tooth, and/or inside the post-extraction tooth socket during various steps associated with or defining part of the dental restoration method described herein. For instance, the laser may be used to disinfect areas of the gums or sockets during gingival cuff elevation, bone removal, tooth extraction, implant placement, etc.

As can be appreciated, elevating the gingival cuff with a laser such as the Waterlase iPlus all-tissue laser can decrease procedure time, minimize discomfort, and accelerate healing and recovery. In that regard, when using a high-powered laser to elevate the gingival cuff, the exposed root surface area of the tooth can be maximized without increasing pain, bleeding, or procedure time, such as when using a scalpel. In other words, an increased area of the tooth root may be exposed without causing increased pain, bleeding, or procedure time, allowing for easier access by a tooth extraction tool.

A high-powered laser may also be used to remove a small, controlled amount of alveolar bone near a tooth root to help support a clean extraction of the tooth. Removing a small amount of alveolar bone can support extraction of a tooth without damaging or otherwise breaking portions of the alveolar bone defining the original dental inter-radicular ridge and the interdental and interseptal bone and without compromising the post-extraction root socket walls (e.g., the 360-degree enclosed wall of the socket).

In one example, a high-powered laser may be used to remove a small, controlled amount of alveolar bone around at least a portion of the circumference of the tooth. For instance, the laser can be used to remove alveolar bone circumferentially around the entire tooth root along a longitudinal section of the tooth root. In this manner, an annular gap is effectively defined between the root surface of the tooth and the remaining alveolar bone. In other instances, the laser can be used to remove alveolar bone circumferentially around a portion of the tooth root that is adjacent to the buccal plate along a longitudinal section of the tooth root. In this manner, a gap is effectively defined between the root surface of the tooth and the buccal plate.

Referring to FIGS. 12B-12E, a high-powered laser may also be used to remove a small, controlled amount of alveolar bone near a buccal side of a tooth root to substantially prevent damage or breakage of the buccal plate for that tooth. The buccal plate BP, or the bone that is on the buccal side of the of the tooth's root, may define part of the tooth socket walls, the inter-radicular ridge, the interdental bone, and/or the interseptal bone. It is often difficult to extract upper and lower canines without damaging or otherwise breaking the buccal plate corresponding to that canine.

The buccal plate is especially susceptible to damage or breakage when extracting canines because those teeth are typically the longest rooted teeth, and they are positioned very closely to the buccal plate. More specifically, canines are generally round in cross-section and bigger than incisors, and consequently, the canines sit very close to the edge of the corresponding buccal plate. As a result, the buccal plate corresponding to a canine is thin and almost fused with the root of the canine. The thin, almost fused buccal plate corresponding to a canine is thus very susceptible to breaking during extraction of the canine.

As shown in FIGS. 12B-12E, a high-powered laser L can help separate the buccal plate BP from the root R of the corresponding canine CT before extraction. In one example, a high-powered laser L may be used to remove a small, controlled amount of alveolar bone defining the buccal plate BP and/or a portion of the root of the canine CT extending along the buccal plate BP.

Figure 12B:
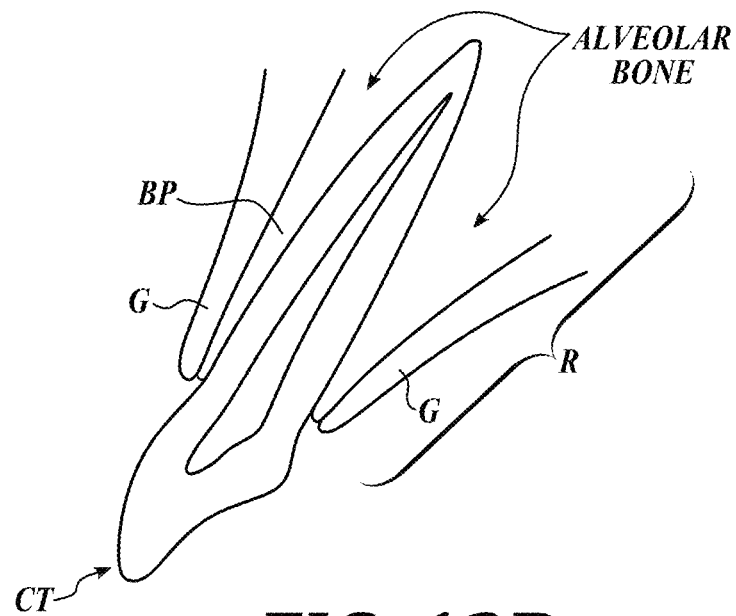

For instance, referring specifically to FIG. 12B, the buccal plate BP extends along a buccal portion of the root R of a canine CT. After optionally elevating the gingival cuff such as in a manner described herein, a tip T of a high-powered laser L may be located near the intersection of the gingiva G and the root R such that the water-energized laser beam of the laser L can be directed at the outer surface of the root R and/or the buccal plate BP.

Figure 12C:
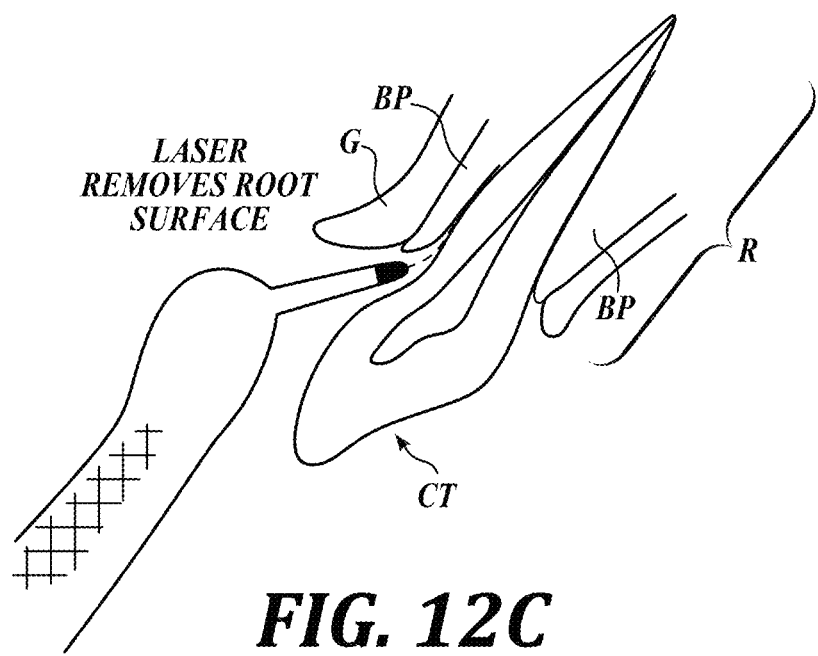
Figure 12D:
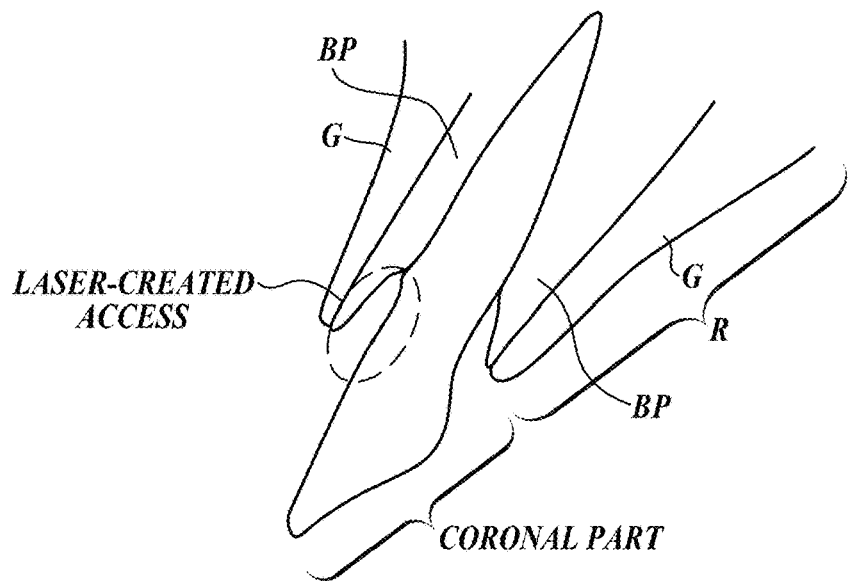
Figure 12E:
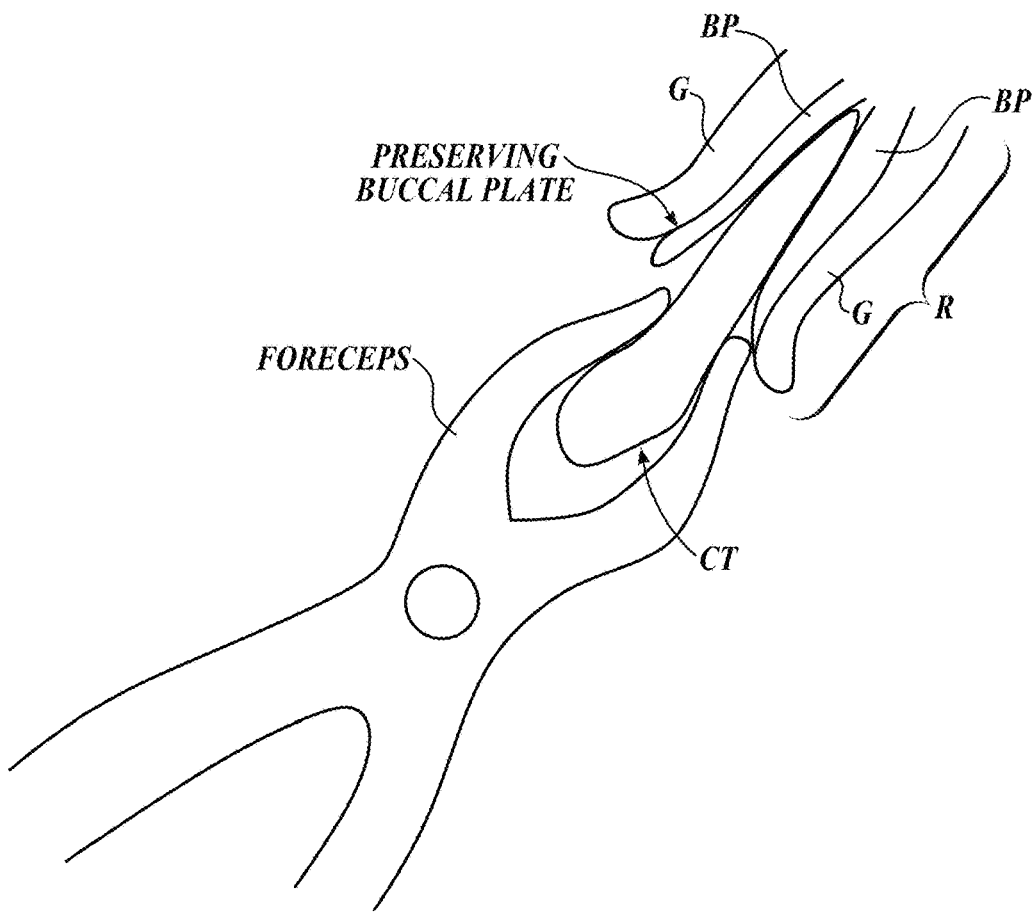

In the example shown in FIG. 12C, the tip T of a high-powered laser L is located between an elevated gingival cuff GC and a coronal portion of a canine CT. The water-energized laser beam of the laser L is directed at the outer surface of the root R between the root and the buccal plate BP. The energy of the laser may be used to remove or cut away a small amount of the root R between the root and the buccal plate BP. The removed amount may extend along a length of the root generally from an intersection of the coronal portion and root portion of the canine CT toward an apex of the root R. Any suitable amount of the root R may be removed to help enable forceps to be inserted into the area between the buccal plate BP and the tooth root R (see FIG. 12E). For instance, the amount of root R removed or cut away may be about 1 mm in depth and about 3-4 mm in length (see also FIG. 12D).

In addition, or in the alternative, a small, controlled amount of alveolar bone defining the buccal plate BP may be removed. In that regard, the tip T of a high-powered laser L may be located between an elevated gingival cuff GC and a coronal portion of a canine CT, as shown in FIG. 12C. The water-energized laser beam of the laser L may be directed at the lingual/palatal surface of the buccal plate BP. The energy of the laser may be used to remove or cut away a small amount of the buccal plate BP on the lingual/palatal side of the buccal plate BP. The removed amount may extend along a length of the buccal plate BP generally from a tip of the buccal plate BP to toward an apex of the root R. Any suitable amount of the buccal plate BP may be removed to help enable forceps to be inserted into the area between the buccal plate BP and the tooth root R. For instance, the amount of the buccal plate BP removed or cut away may be about 1 mm in depth and about 3-4 mm in length.

Preferably, only the root R of the canine is removed or cut away, and little to no portion of the buccal plate BP is removed. As can be appreciated, removing any portion of the buccal plate BP, even a small amount, can weaken the buccal plate BP. If significant portions of the buccal plate BP are removed, a bone graft may be required to strengthen the post-extraction tooth socket defined by the buccal plate BP such that it can support an implant and/or mate with the ovate contours of the dental bridge without breaking. Removing a portion of the root R, on the other hand, does not compromise the strength of buccal plate BP. Only the strength of the tooth is compromised, but seeing as the tooth is extracted, there is no impact on the ultimate such Removing a portion of the root R further does not compromise the mating interface between the gingival ridge and the dental bridge because the tooth is entirely replaced by the dental bridge.

It can be appreciated that by removing a small, controlled amount of a tooth root and/or the buccal plate, the canine CT can be extracted without breaking or damaging the remaining alveolar bone, including the intact buccal plate. The remaining alveolar bone, including the intact buccal plate, defines a suitable post-extraction tooth socket for receiving a socket-sized implant as described herein. Moreover, the original dental inter-radicular ridge and the interdental and interseptal bone remains intact for mating with the dental bridge as described herein. Thus, as noted above, use of a high-powered laser, such as the Waterlase iPlus all-tissue laser described herein, supports a natural, gentle, atraumatic approach to tooth extraction and ridge preservation.

A high-powered laser may also be used to cut a tooth into two or more sections along its length that substantially correspond to the number of roots for that tooth. Sometimes teeth can have two or more roots, and removing the tooth with each root substantially in tact and without damaging the surrounding alveolar bone can be difficult without first cutting the tooth into sections. For instance, molars can have two, three, or four roots. Thus, for single teeth extractions and replacements, it has been common practice to cut the tooth axially along its length into different sections that substantially align with the tooth root. In that manner, each section of the tooth, including its coronal and root portion, can be removed without damaging the surrounding alveolar bone.

Prior art methods include using a surgical hand piece (such as a fissure burr) to cut the tooth into sections. Such methods are time consuming, traumatic, and require significant anesthesia. In accordance with the systems and methods disclosed herein, which aim to support a gentle, atraumatic approach to extraction and ridge preservation, a high-powered laser is used. For instance, the Waterlase iPlus all-tissue laser described herein may be used to cut a tooth into two or more sections along its length that substantially corresponds to the number of roots for that tooth. The water-energized laser beam of the laser can be directed at the incisal/occlusal surface of the tooth and a cut can be made along the length of the tooth. Specifically, the tooth may be cut to define a tooth section having a coronal portion and a corresponding root portion. After the tooth section is separated from the remaining portion of the tooth, the section may be independently removed.

A high-powered laser may be used at different settings depending on the application. In some examples, the high-powered laser may be controllable by a computing device having instructions stored thereon for operating the laser at a certain power level, frequency, etc., depending on the input received by a user. For instance, a user may interact with an input device of an associated computing device (e.g., a control panel) to select a power (Wattage or W), frequency (Hertz or Hz), air level (spray %), and water level (spray %) suitable for the application. Generally, a treatment may be started at a low power level and increased as necessary using clinical judgment.

In some examples, the associated computing device may have programmable laser presets stored in system memory such that a user may simply select an application, category, etc., and the laser is then set at a certain power (W), frequency (Hz), air level, and water level. When a particular combination of customized values is found to be especially effective and useful, the user may also store them as a new preset in system memory.

In some examples, one of various "soft tissue" laser presets may be chosen to perform certain operations relative to the gum tissue, such as elevating the gingival cuff, recovering an implant covered by gingival tissue, creating an insertion opening for an implant, etc. A soft tissue preset may have a power level between about 1.5 W-2.25 W and a frequency level between about 25-50 Hz, with corresponding air and water supply (spray %) to provide comfort to the patient during use. A "gingivectomy" setting or similar may be used for at least one of elevating a gingival cuff, cauterizing gingiva, disinfecting areas in the gum tissue and/or around the tooth, etc.

An "implant uncover" setting or similar may be used for recovering an implant covered by gingival tissue. For instance, to cut through gum tissue to recover an implant, the laser may be used at a power setting of about 2.00 W and a frequency of about 40 Hz. In another instance, the laser may be used at a power setting of about 1.50 W and a frequency of about 50 Hz to contour gingiva, such as around an implant collar.

In some examples, one of various "bone" or "hard tissue" presets may be chosen for effectively removing or penetrating through bone. For instance, to remove a small amount of bone, such as near the buccal plate, the laser may be used at a power setting of about 3.00 W and a frequency of about 25 Hz, with corresponding air and water supply (spray %) to provide comfort to the patient during use. The amount of air and water supply (spray %) may be increased for a hard tissue preset to account for the higher amount of power used.

As can be appreciated, the laser may be used at a higher power (W) and lower frequency (Hz) level to cut through thicker tissue or bone, and it may be used at a lower power (W) and higher frequency (Hz) level to treat tissue or bone more delicately. In any event, if the laser is a Waterlase iPlus all-tissue laser, it may use a Biolase proprietary wavelength of 2780 nm Er,Cr:YSGG.

When elevating the gingival cuff, care is taken to try to avoid laying a full thickness mucoperiosteal flap longer than about 2 mm around the tooth in the active quadrant. With the gingival cuff elevated around the tooth, the upper (coronal) quadrant of the root surface is exposed, and the beaks of forceps may be placed around the upper quadrant of the root surface (e.g., past the crown, not substantially touching the crown of the tooth).

With the beaks of the forceps around the upper quadrant of the root surface, as generally shown in FIG. 12, the atraumatic tooth extraction process may include applying force to the tooth in the socket, such as to loosen the tooth and eventually extract the tooth. For instance, the atraumatic tooth extraction process may include applying apical pressure and/or lateral pressure and/or an upwardly pulling force to the tooth in its socket.

Apical pressure and/or lateral pressure helps enlarge the tooth socket of the tooth because the tooth is denser than the alveolar bone; and therefore, pressure from the tooth's root applied to the alveolar bone in the socket pushes the alveolar bone away from the root (e.g., it condenses the alveolar bone surrounding the socket). As a result, the tooth socket expands. A suitable amount of pressure is applied to sufficiently enlarge the socket to allow for the tooth to loosen and for the tooth to be atraumatically extracted in accordance with the methods described herein.

Figure 13:
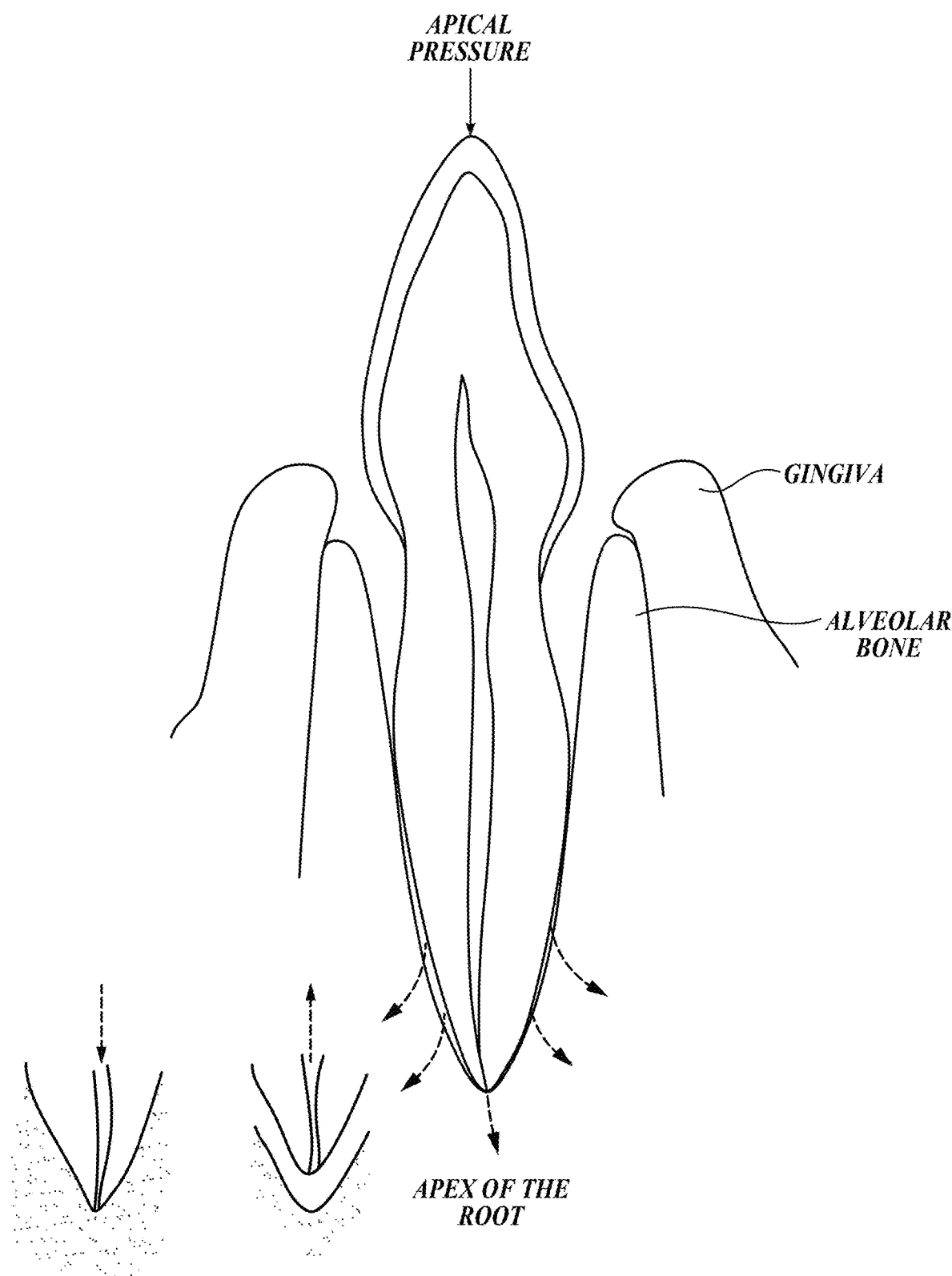
FIG. 13 depicts an image showing further aspects of an atraumatic tooth extraction in accordance with exemplary aspects of the pre-prosthetic ridge preservation process of FIG. 9.

For instance, referring to FIG. 13, the beaks of the forceps may be aligned substantially parallel to the longitudinal axis of the tooth (not shown), and apical pressure may be applied to the tooth (e.g., as if trying to move the tooth deeper down into its socket). More specifically, with the beaks of the forceps firmly holding the tooth (e.g., from the upper quadrant of the root), firm pressure may be applied to the tooth pressing it apically (upwards for upper teeth; downward for lower teeth). The apical pressure may be applied for a predetermined amount of time (e.g., for about 10 seconds), depending on the nature of the tooth, any pathologies of the tooth, the sensed movement of the tooth during application of apical pressure, etc.

Apical pressure helps enlarge the tooth socket at its apical tip. More specifically, pressure from the tooth's root applied to the alveolar bone at the apical tip pushes the alveolar bone away from the root (e.g., it condenses the apical part of the alveolar bone). After applying apical pressure, the tooth may be pulled upwardly and brought back to the starting position (e.g., substantially the original position of the tooth).

As noted above, lateral pressure and/or an upwardly pulling force may also be applied to loosen the tooth in its socket. For instance, when gripping the tooth near its root (e.g., past the crown) with beaks of forceps, as shown in FIG. 12, the tooth may be gently moved laterally in its socket, further expanding the socket in the alveolar bone. For instance, a "figure of eight" (or "FIG. 8") movement and/or a bucco-lingual movement can be used to further expand the socket in the alveolar bone, further loosening the tooth.

After a sufficient amount of lateral and/or apical pressure/movement is applied, the atraumatic tooth extraction process may further include pulling upwardly on the tooth either in isolation or when moving the tooth laterally in its socket. Extraction of the tooth is ultimately accomplished with at least some upward pulling movement/force.

As noted above with respect to FIG. 11, if a tooth breaks during extraction, and the tooth has a substantially disease-free root tip and sits firmly in the bone, the root-tip can remain in the alveolar bone substantially undisturbed, and further steps can be taken to ensure proper healing. For instance, the socket containing the root tip can be irrigated with sterile saline, and primary closure can be performed for the extraction socket as needed in accordance with known methods, such as the method described in the article "Leaving a Root Behind on Purpose—Coronectomy", by Dr. Karl Koerner. In other instances, a high-powered laser such as the Waterlase iPlus all-tissue laser may be used to help remove any necessary portions of the root tip, disinfect the extraction socket containing the root tip, control bleeding, and/or assist in primary closure. It should be appreciated that in most instances, removal of the root-tip would require more surgery and destruction of alveolar bone, which is contrary to the intention of preserving the alveolar bone using the pre-prosthetic ridge preservation process described herein. However, as is normally the case, a dental professional will take necessary measures to ensure patient safety and overall success for restoration.

Figure 14A:
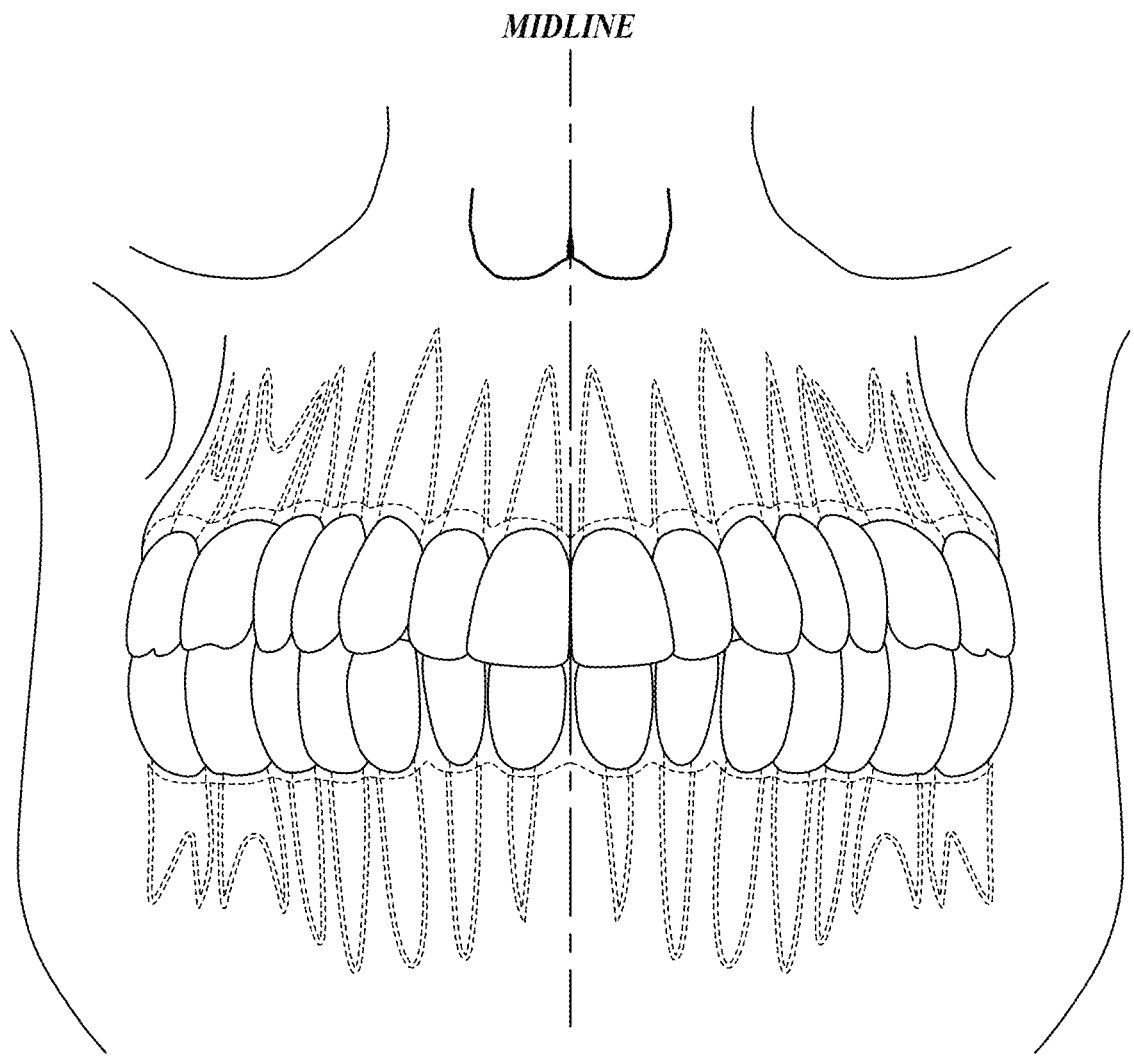
FIGS. 14A-14B depicts an image of an upper and lower jaw before and after atraumatic tooth extraction performed in accordance with exemplary aspects of the pre-prosthetic ridge preservation process of FIG. 9.
Figure 14B:
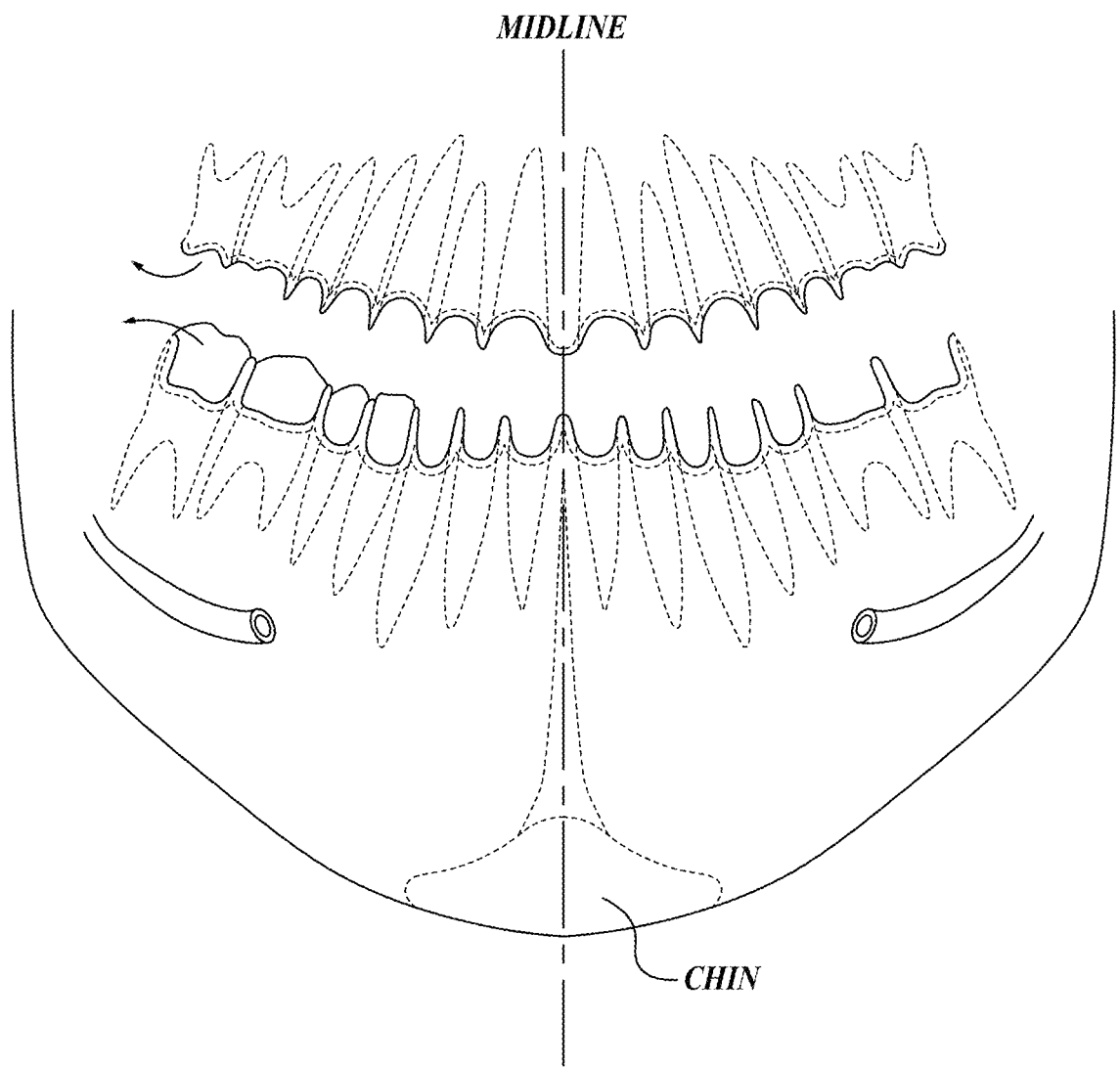
Figure 15A:
FIG. 15A depicts a photograph image of a patient's upper jaw showing all teeth extracted using an atraumatic tooth extraction process performed in accordance with exemplary aspects of the pre-prosthetic ridge preservation process of FIG. 9.

FIGS. 14A and 14B show a drawing of an upper and lower jaw before and generally after atraumatic tooth extractions performed in accordance with exemplary aspects of the pre-prosthetic ridge preservation process described herein. FIG. 15A depicts a photograph of a patient's upper jaw showing post-extraction root sockets just after all teeth were extracted using an atraumatic tooth extraction process performed in accordance with exemplary aspects of the ridge preservation process described herein. As noted above, all four walls of the post-extraction root socket (e.g., the 360-degree enclosed wall of the socket) are substantially left intact using the pre-prosthetic ridge preservation process. The pre-prosthetic ridge preservation process substantially preserves the alveolar bone and the full height of the dental inter-radicular ridge.

After the teeth are extracted, steps are taken to ensure appropriate healing of the post-extraction root sockets in preparation for implant placement. For instance, the post-extraction root sockets may be cleaned or irrigated, such as with saline rinse. A high-powered laser may also be used to help disinfect the post-extraction root socket and/or to help stop or control bleeding. For instance, the energy beam of the laser may be directed into the cavity of the post-extraction root socket to help disinfect the post-extraction root socket and/or control bleeding.

The post-extraction socket may also be inspected to ensure that all four walls (360 degrees of the socket) are intact, and if not, appropriate measures may be taken to restore the socket walls (e.g., bone grafting). The gingiva and interdental papilla may also be inspected to ensure they are intact, and if not, appropriate measures may be taken to restore the tissue (e.g., sutures for closing the gingiva). A high-powered laser may be used to help disinfect and/or control bleeding during any restoration or repair of the socket walls or gingiva.

Temporary dentures may be placed on the arch(es) of a patient's mouth after the teeth are extracted and before placement of implants in the post-extraction root sockets. A temporary denture helps protect the post-extraction root sockets during the healing process. A temporary denture may be secured to the arch in any suitable manner.

Figure 15B:
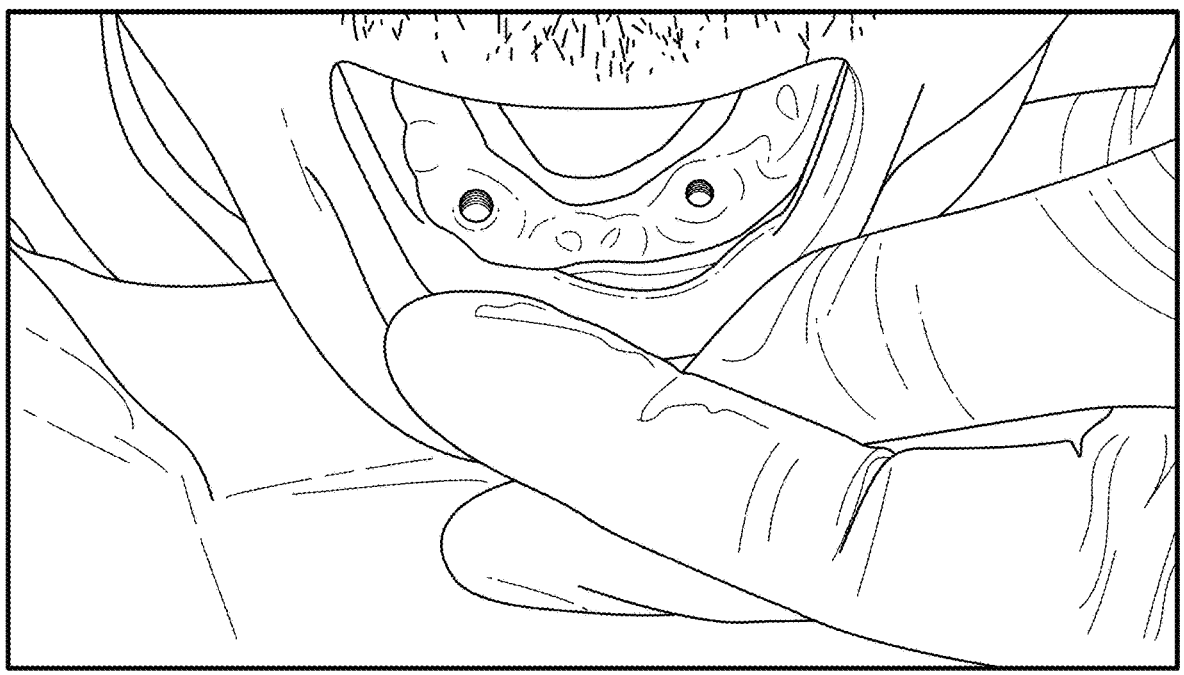
FIG. 15B depicts a photograph image of a patient's lower jaw showing post-extraction sockets about two months after all teeth were extracted using an atraumatic tooth extraction process performed in accordance with exemplary aspects of the pre-prosthetic ridge preservation process of FIG. 9.

FIG. 15B depicts a photograph image of a patient's lower jaw showing post-extraction sockets about two months after all teeth were extracted using an atraumatic tooth extraction process performed in accordance with exemplary aspects of the pre-prosthetic ridge preservation process described herein. In this example depicted, bone remodeling has occurred, and the socket tissue has substantially healed. Note that an outline of each post-extraction socket is generally defined by a dimple in the gingiva or the gum line, thereby providing a visual indication of the location of the socket for implant placement. In that regard, if a patient has healed in the manner depicted in FIG. 15B, the patient may be ready for implant placement, generally described below. In that regard, two implants are shown placed into formed sockets of the lower jaw in the image of FIG. 15B.

Placement of Implants

Exemplary aspects of steps for placing implants into post-extraction root sockets preserved using the pre-prosthetic ridge preservation process or another process that produces similar results, will now be described with reference to FIGS. 16A-16B and 17A-17C. Generally, in accordance with the examples described herein, tooth-sized (non-angulated) implants are secured in the preserved post-extraction root sockets. The tooth-sized (non-angulated) implants can be used even in the posterior region of the jaw (e.g., the first molar tooth socket) because the implants can be secured in the alveolar bone of the patient. In other words, angulated implants, as used in the prior art method, are not necessary because sufficient posterior jawbone density is preserved (i.e., it is not removed during the pre-prosthetic surgery as in the prior art method).

The tooth-sized (non-angulated) implants may be placed into the appropriate post-extraction root sockets at the most favorable stage of ossification, such as when the bone cells are actively forming new cells (osteoblasts) and these new cells can osseointegrate with the implants. In general, the implants may be placed in the post-extraction sockets after sufficient bone remodeling is complete and the socket tissue is healed (e.g., 30-60 days after extractions), as generally shown in FIG. 15B. The implants, once osseointegrated, are used to secure the dental bridge 100 to the jaw of the patient.

Figure 16A:
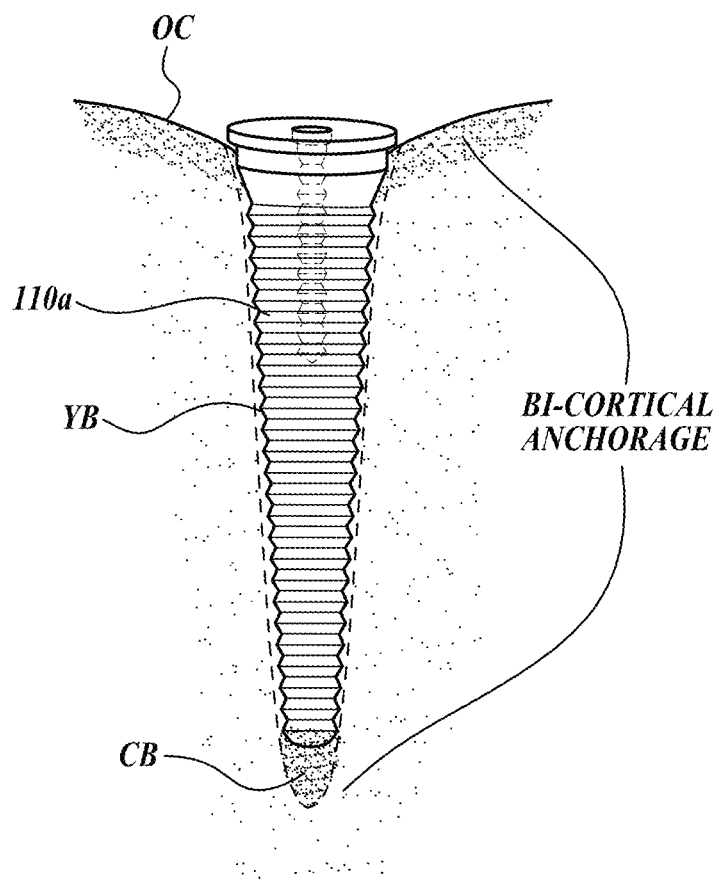
FIG. 16A depicts a front view of bi-cortical anchorage of an implant placed within a tooth socket preserved in accordance with exemplary aspects of the pre-prosthetic ridge preservation process of FIG. 9.
Figure 16B:
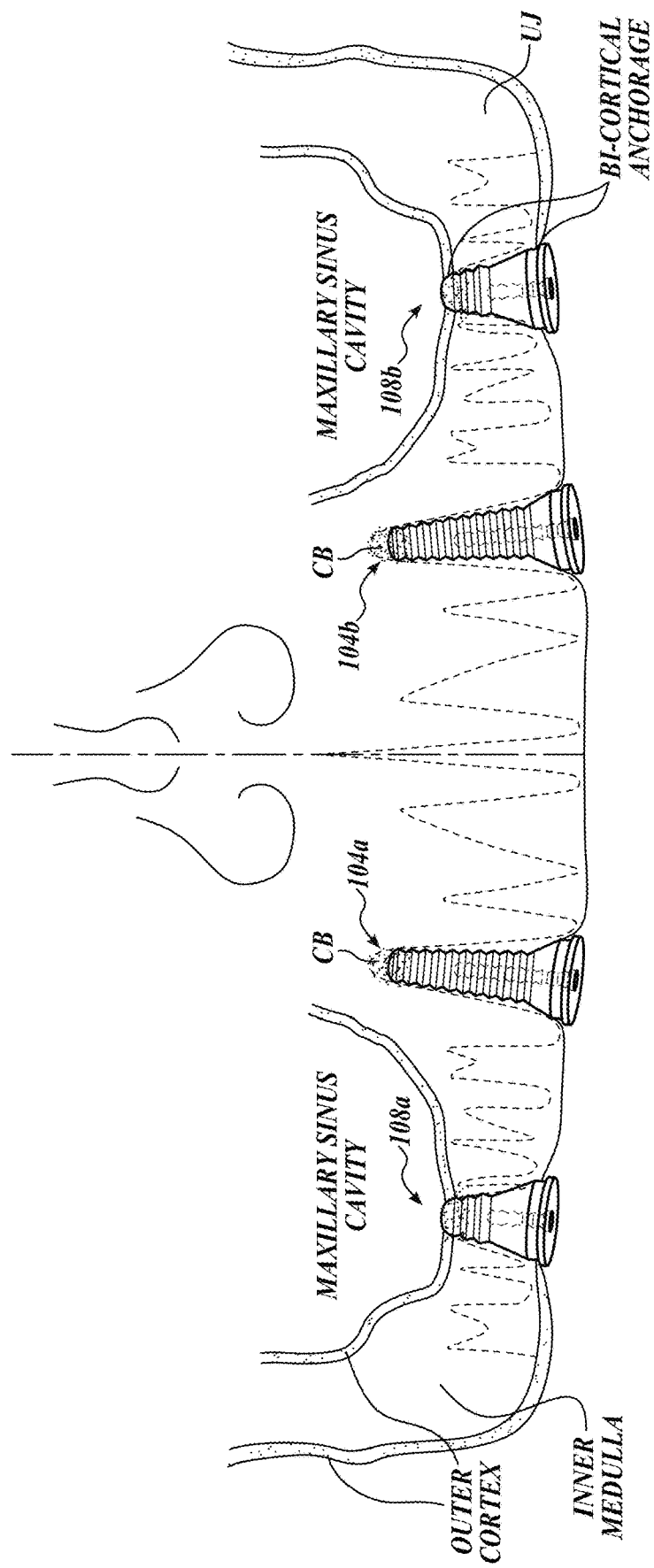
FIG. 16B depicts a front view of a plurality of implants placed within tooth sockets of an upper jaw of a patient, wherein the tooth sockets were preserved in accordance with exemplary aspects of the pre-prosthetic ridge preservation process of FIG. 9.

Referring to FIG. 16A, within a short period of time after tooth extraction, osteoblast/osteoclasts interaction and remodeling takes place and re-fills socket space with a new young bone YB. The new young bone YB, which is not yet hard and calcified, is soft, malleable, and generally easy to work with. As a result, an implant 110 can often be placed into the young bone YB without osteotomy (drilling away bone). In most instances, the implant 110 can be placed in the young bone YB without the need to even drill a pilot hole.

As noted above, apical pressure applied during extraction condenses the apical part of the alveolar bone. More specifically, the bone cells are concentrated at the apical part of the alveolar bone, forming a cortex-like layer of the bone or condensed bone CB. The condensed bone CB at the apical part of the alveolar bone, which is hard and thick, can be used for bi-cortical anchorage of the implant 110, as shown in FIG. 16A. Bi-cortical anchorage results when the implant is engaged inside the thick cortical bone from the platform (or the top of the implant) and from the apex of the implant.

As can be seen in FIG. 16A, the platform of the implant 110 is engaged in the outer cortex OC of the ridge of the alveolar bone and the apex of the implant is engaged in the condensed bone CB at the apical part of the alveolar bone. The body of the implant 110 is within the softer, young bone YB. Bi-cortical anchorage of the implant within the preserved alveolar bone minimizes any failure of the implant, e.g., it provides superior anchorage resistance, reduced cortical bone stress, and superior stability compared to, for instance, mono-cortical anchorage.

Tooth or socket sized implants are placed into a necessary number of sockets to secure the dental bridge to the preserved ridge. For instance, in the examples shown in FIGS. 16B and 17A (as well as FIG. 8), four implants are placed into four corresponding sockets for a full mouth replacement. Specifically, for the upper jaw UJ on a first side, an anterior tooth-sized implant 104a is secured in the canine tooth socket, and a posterior tooth-sized implant 108a is secured in the first molar tooth socket. Similarly, an anterior tooth-sized implant 104b is secured in the canine tooth socket on a second side of the upper jaw UJ, and a posterior tooth-sized implant 108b is secured in the first molar tooth socket on the second side of the upper jaw UJ. A similar implant arrangement may be used for the lower jaw LJ (see FIGS. 8 and 17A).

The implants are placed in sockets for former teeth #3 (upper right first molar), #6 (upper right canine), #11 (upper left canine), and #14 (upper left first molar) (see FIG. 8, which shows anterior and posterior-sized implants 104a/104b and 108a/108b secured in the canine and first molar tooth sockets, respectively, of an upper jaw UJ). Generally, such implant placement provides sufficient canine to molar spread (e.g., good anterior-posterior distance), which provides good retention and stability for the dental bridge 100.

In some cases, there may be insufficient bone in one or more of the above-noted locations. In such an instance, the placement of the implant can be moved one tooth (socket) mesially (e.g., placing posterior tooth-sized implant 108a in the upper second bicuspid tooth socket rather than in the first molar tooth socket) and/or an additional implant may be placed in the respective quadrant of the jaw. If there is insufficient bone between the maxillary sinus cavity and the posterior ridge, then a short implant (e.g., of about 8 mm height and 4.3 mm width) may be used, wherein the apex of the implant engages the bony floor of the sinus cavity floor having condensed bone, as shown for implants 108a and 108b in FIG. 16B (see also FIG. 17A).

When placing the implants (typically after local anesthetization), there is typically no need to incise the gingiva or lay a flap in order to expose the underlying bone. Rather, when using the pre-prosthetic ridge preservation process described herein, the socket space is typically well defined. More specifically, after the extraction socket has healed, it typically shows a clear dimple of the former tooth location because the pre-prosthetic ridge preservation process described herein substantially maintains the alveolar bone in its entirety, and the outline of the socket shows through the gingiva (see FIG. 15B). However, if preferred, the gingiva may be released at the height of the alveolar ridge to expose the bony ridge over the former tooth socket before implant placement.

In one example, the gingiva is released with a #15 blade and periosteal elevator or the like to lay a full thickness mucoperiosteal flap less than about 5 mm in a buccal direction and 2 mm in a palatal direction to expose the underlying bone. In such an example, a high-powered laser may be used to disinfect and/or control bleeding at a site of gingival release.

In other examples, a high-powered laser may be used to release the gingiva before implant placement. For instance, a high-powered laser may be used create a small incision (or a substantially straight cut) in substantially the center of the dimple of the healed post-extraction tooth socket. The incision may be of a sufficient length and depth to expose the underlying bone. For instance, the length of the incision may be about 1.5 mm, and the depth of the incision may be about 3 mm. A "soft tissue" laser preset or similar may be used. For instance, the laser may be used at 1.5 W and 25 Hz with suitable air and water spray (e.g., 20%) to incise the gum tissue. Again, the laser may be used to disinfect and/or control bleeding at a site of gingival release.

The exposed bone beneath the gingiva incision site is new young bone YB that has filled the post-extraction tooth socket. As discussed above, the young bone is not yet hard and calcified. Rather, it is soft, malleable, and generally easy to work with. As a result, an implant can often be placed into the young bone YB without osteotomy (drilling away bone). In most instances, the implant can be placed in the young bone YB without the need to even define a pilot hole. However, if a pilot hole is preferred, it may be done with a high-powered laser, such as the Waterlase iPlus all-tissue laser described herein.

For instance, the laser may be used on an "implant placement" or "hard tissue" laser preset, such as at 3.0 W and 25 Hz. As can be appreciated, such a setting is higher power than a "soft tissue" laser preset (e.g., 1.5 W and 25 Hz) such that the laser may penetrate the bone. In that regard, an increased amount of air and water spray (e.g., 70 and 80%, respectively) may be used to cool the bone as it is penetrated by the laser.

The laser may penetrate through the bone to create a pilot hole in the exposed bone suitable for receiving a preferred implant, such as the Hahn tapered implant discussed herein. A laser tip of an increased length (such as compared to a tip used for the gingiva release) may be used to reach down through the gap in the released gingiva and into the depth of the pilot hole.

It can be appreciated that although a pilot hole may not be necessary, it may be preferable to define a pilot hole given the ease of doing so. Conventional methods use a drill to define a pilot hole, which causes discomfort to the patient, requiring more anesthetization. Moreover, in prior art methods like an All on 4 procedure, a pilot hole is not only necessary because the implants are being secured within a region of the jaw with higher bone density, it also requires more power/energy because of the bone density. By comparison, a pilot hole may be easily created in the softer, young bone YB of the post-extraction tooth socket with a high-power laser such as that described herein.

The implant may be driven into the socket through the newly healed-over gingiva, optionally after a gingiva release and pilot hole creation, until the implant is sufficiently torqued, such as to about 35 Ncm or higher (e.g., to about 35 Ncm to 40 Ncm). A healing cap (see FIGS. 17A and 17B) is placed on the implant and sufficiently torqued, such as to about 15 Ncm. If sufficient torque of the implant is not achieved, an additional implant may be added to a nearby socket and torqued to a sufficient level, such as to about 35

Ncm or higher. Achieving bi-cortical anchorage of the implant helps allow the implant to be sufficiently torqued.

Figure 17A:
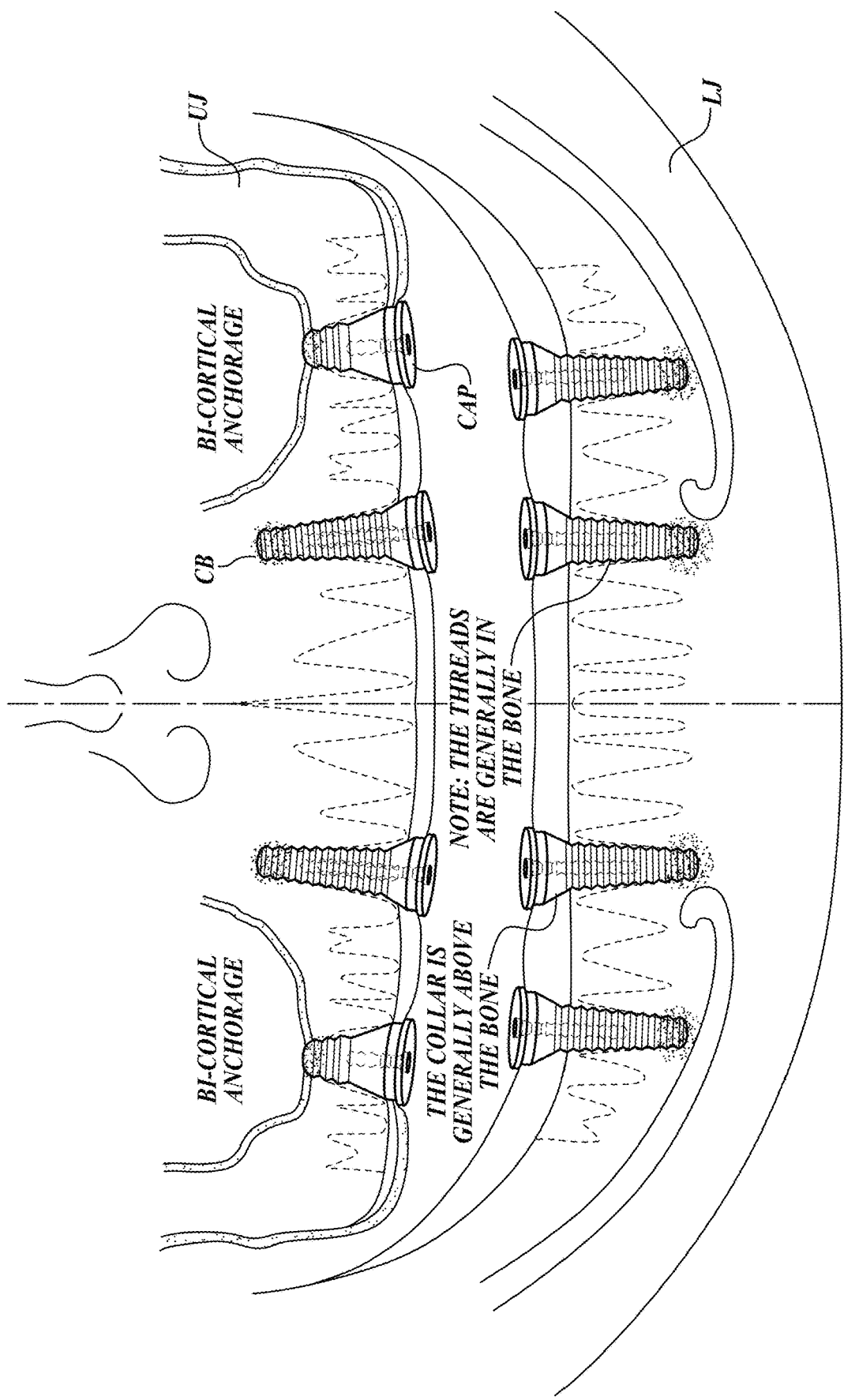
FIG. 17A depicts a front view of a plurality of implants placed within tooth sockets of upper and lower jaws of a patient, wherein the tooth sockets were preserved in accordance with exemplary aspects of the pre-prosthetic ridge preservation process of FIG. 9, and wherein healing caps have been secured to each of the implants.
Figure 17B:
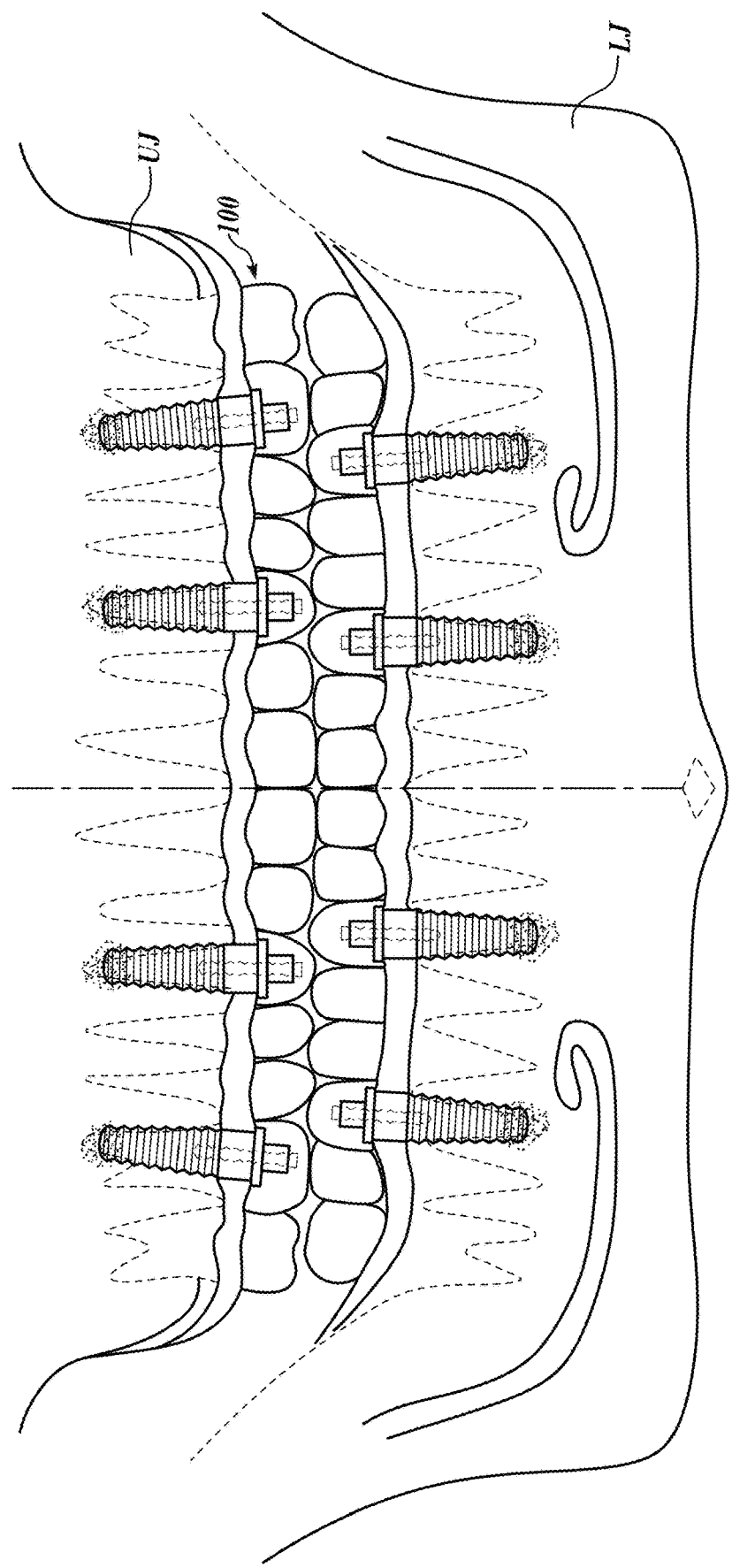
FIG. 17B depicts a front view of first and second dental bridges formed in accordance with exemplary aspects of the present disclosure secured to upper and lower jaws of a patient, respectively, using a plurality of implants placed within tooth sockets of the upper and lower jaws of a patient, wherein the tooth sockets were preserved in accordance with exemplary aspects of the pre-prosthetic ridge preservation process of FIG. 9.
Figure 17C:
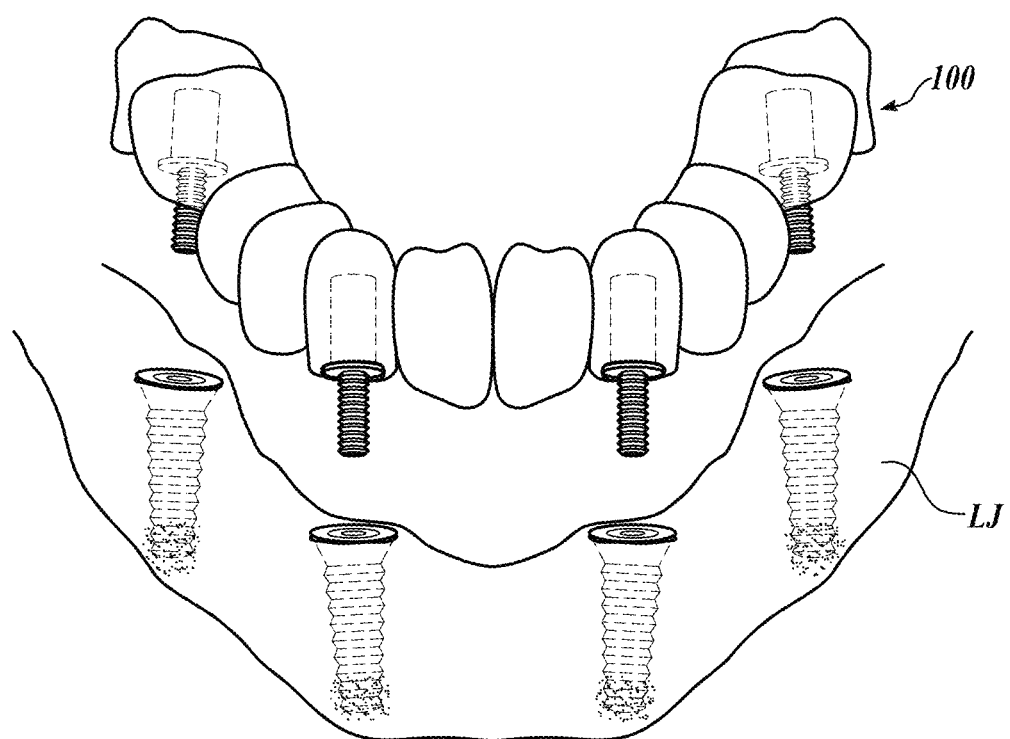
FIG. 17C depicts an isometric view of a dental bridge formed in accordance with exemplary aspects of the present disclosure being secured to a lower jaw of a patient.

Referring to FIGS. 17A-17C, the implants are preferably placed in the root sockets such that a platform of the implant is substantially flush with the gingival-periosteal interface and a collar or neck of the implant protrudes from the tooth socket. More specifically, the oblique threads defined on the body of the implant may be disposed in the newly ossifying portions of the alveolar bone defining the socket, the fine threads (not shown in detail) may be disposed in the outer cortex layer of the bone, and the collar of the implant may be located generally above the outer cortex layer of the bone at least partially in the gingiva layer.

For instance, the collar of the implant may be placed in a cleansable area of an upper-most periosteal layer of the bone/gingiva interface. In this manner, the implant can be accessed and engaged by the abutments when installing the dental bridge 100. More specifically, the collar of the implant can be accessed by both engaging and non-engaging abutments embedded within the dental bridge 100. By comparison, angulated implants used for the All on 4 method or similar locate the collar of the implant entirely within the bone.

In cases where the implant is placed but cannot be torqued such that the platform of the implant is substantially flush with the gingival-periosteal interface, the implant hole may be deepened slightly (such as with a 3.5 mm bur of length 11.5 mm and/or with a high-powered laser) to allow the implant to go deeper into the bone. However, special care is taken to avoid over-enlarging the implant hole, which would likely compromise the engagement of the implant with the alveolar bone in the socket.

As can be seen in the FIGS., the socket-sized and socket-based implants are generally tapered to substantially match at least a portion of the shape of the post-extraction socket. In this manner, the implant, when placed, does not substantially disturb the height and width of the patient's original true ridge. In other words, the tapered implants are substantially received within the post-extraction socket without destroying other portions of the alveolar bone surrounding the socket. In one example, the socket-sized and socket-based implants are Hahn™ tapered implants available from Glidewell Direct of Irvine, CA.

Each of the implants are placed into the sockets such that a longitudinal axis of each of the implants is substantially coaxially aligned with a longitudinal axis of the corresponding tooth socket, as shown in FIGS. 16A, 16B, 17A, and 17B. In this manner, the implant substantially harmoniously resembles the roots of the original teeth. Moreover, when secured within the sockets, the implant is safely housed within the jawbone, and it does not protrude buccally or lingually from the bone.

Implants may be placed into the former tooth sockets (root sockets) free-handed, with the aid of a surgical guide, or a combination thereof. If placed free-handed, the root socket longitudinal axis may be determined using, for instance, a CBCT scan and optionally an intraoral scan. In that regard, the straight, longitudinal axis of the implant may be substantially aligned with the root socket longitudinal axis, and the implant may be drilled into the bone of the root socket along that axis. For instance, if the root socket longitudinal axis extends buccally/labially from an apex of the root to the gingiva at an angle of substantially 5 degrees from vertical, the implant may be arranged such that its straight, longitudinal axis is substantially 5 degrees from vertical and then drilled into the root socket at that angle. If the root socket longitudinal axis also flares distally and/or mesially from vertical, the implant may likewise be arranged such that the implant axis also flares distally and/or mesially from vertical.

The straight, longitudinal axis of the implant may be substantially aligned with the root socket longitudinal axis using visual markers, cues, etc., such as the root socket dimple defined in the gums, the notable flare of the patient's arch, an x-ray of the patient's arch relative to a marker, a laser extending from the drill, etc. The implant can be driven into the socket at the desired angle until the collar C of the implant is located generally above the outer cortex layer of the bone at least partially in the gingiva layer.

In the alternative or in addition, a surgical guide may be used to substantially align the straight, longitudinal axis of the implant with the root socket longitudinal axis and/or define a depth limitation of the implant. As noted above, the full arch dental restoration device arch preparation system and method may incorporate aspects of a design and use of a surgical guide configured to aid in implant placement. Exemplary detailed aspects of a design and use of a surgical guide will now be described.

Surgical Guide Design and Use

A surgical guide is a physical device that is placed into the patient's mouth that provides indicators specifying the location of implant placement, assisting to drill implants into the bone with optimal accuracy. A surgical guide is typically designed with suitable software tools by digitally defining optimal implant positions according to the dental bridge design, accounting for any limitations related to bone density and locations of important structures in the bone. The surgical guide is used to transfer the digital design during the procedure, allowing a practitioner to place implants with precision.

Preferably, a tooth-borne surgical guide is used, which is designed to engage teeth of the patient during implant placement. In that regard, at least some of the teeth that are not sites for implant placement may be left intact in the replacement arch of the patient for design and use of a tooth-borne surgical guide. In other words, the teeth whose tooth sockets are intended for housing an implant will be removed for the step of implant placement and surgical guide design. At least some of the teeth that will not (at least initially) define a tooth socket for implant placement will remain in the patients replacement arch to provide base support and consistently reproducible landmarks for the tooth-borne surgical guide. A gingiva-borne surgical guide may be used for an edentulous patient, or a patient lacking all original teeth.

Figure 17D:
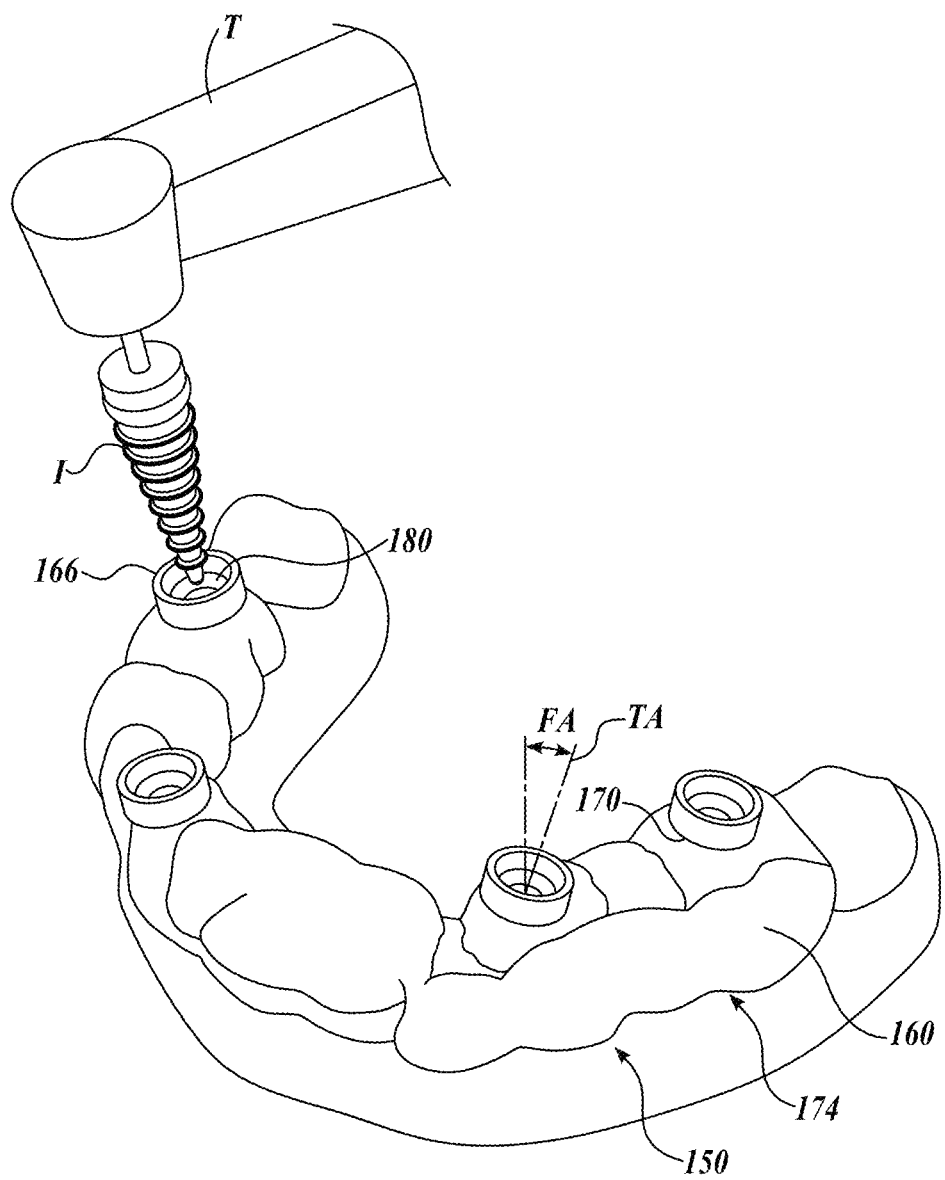
FIG. 17D shows an isometric view of a surgical guide formed in accordance with exemplary aspects of the systems and methods disclosed herein, wherein the surgical guide is shown positioned on a patient's replacement arch.

Referring to FIG. 17D, a surgical guide 150 formed in accordance with systems and methods described herein includes a surgical guide body 160 configured to mate with teeth/gums of a patient's replacement arch, and surgical guide sleeves 166 defined in or received in the body for guiding implant placement into the patient's replacement arch bone of corresponding post-extraction root sockets. The surgical guide body 160 is arch-shaped like the patient's replacement arch and contoured to fit teeth/gums of the patient's replacement arch, similar to a retainer, bite guard, or dentures. The arch-shaped surgical guide body 160 extends between an occlusal/incisal side 170 and a gingival side 174. The gingival side 174 is contoured to fit or mate with the teeth/gums of the patient's replacement arch, similar to a retainer, bite guard, or dentures. In that regard, the body 160 may have a thickness between the occlusal/incisal side 170 and the gingival side 174 suitable to retainably engage teeth/gums in the replacement arch while supporting surgical guide sleeves 166 of a predefined height.

The surgical guide body 160 may be made from any suitable material fabricable into the customized shape and size, and strong enough to retain surgical guide sleeves 166 and/or an implant tool when the implants are being placed into the bone of the replacement arch. Appropriate impressions, scans, images, etc., may be taken of the patient's replacement arch for creating fabrication instructions for the surgical guide body 160. In some examples, the surgical guide body 160 is fabricated using at least one of stereolithography, selective laser sintering, milling, and 3D printing technologies.

As noted above, surgical guide sleeves 166 are defined in or received in the surgical guide body 160 for guiding implant placement into the patient's replacement arch bone. Surgical guide sleeves, as known in the art, are cylindrical metal sleeves that are sized for a particular implant or a group of implants. The sleeves are secured within the body of the surgical guide using known techniques, such as by drilling an opening along a designated axis (per the digital design) and fitting a sleeve within the opening.

Once secured within the surgical guide body 160, the surgical guide sleeves 166 are configured to align an implant I and/or a surgical implant tool T with a root socket for driving the implant into the socket substantially along the root socket longitudinal axis.

The surgical guide sleeves 166 are also configured to limit or otherwise define the insertion depth of the implant within the socket such that the collar of the implant is located generally above the outer cortex layer of the bone at least partially in the gingiva layer.

In that regard, each of the surgical guide sleeves 166 has a longitudinal axis that is substantially coaxially aligned with the corresponding root socket longitudinal axis when the surgical guide 150 is placed on the replacement arch. Moreover, each of the cylindrical surgical guide sleeves 166 may be sized to retain a head H of a surgical implant handpiece or tool T therein while allowing an implant I to pass therethrough.

More specifically, as shown in FIG. 17D, each of the surgical guide sleeves 166 defines a cylindrical opening with an inner diameter that is substantially the same size as or is slightly larger than an outer diameter of a head H of a surgical implant handpiece or tool T. In this manner, when the head H of the surgical implant tool T is inserted into the cylindrical opening of a surgical guide sleeve 166, a longitudinal axis of the head H is maintained in substantial alignment with the corresponding root socket longitudinal axis.

At the same time, each of the surgical guide sleeves 166 has an inner diameter that is larger than an outer nominal diameter of the implant I such that the implant I may pass therethrough for being driven into the root socket by the head H of the surgical implant handpiece or tool T. Upon placement of the surgical guide 150 on the patient's replacement arch, the head H of a surgical implant tool T, together with an implant I, is inserted into each of the surgical guide sleeves 166. A driving component inside the head H of the surgical implant tool T is then used to drill the implant I into the root socket bone substantially along the root socket longitudinal axis.

Each of the surgical guide sleeves 166 is configured to substantially maintain a driving axis of the head H of a surgical implant tool T in alignment with the corresponding root socket longitudinal axis when placing the implant I into the root socket bone. In that regard, each surgical guide sleeve 166 has a depth or length substantially the same as or greater than the height of the head H to maintain alignment of the surgical implant tool T with the corresponding root socket longitudinal axis during placement of the implant. In that manner, head H maintains engagement with the surrounding, tightly fitting sleeve the entire time it is being used to drive the implant into the bone. In the other words, the interface between the surgical guide sleeves 166 and the head H substantially maintains the axis of the implant driving component in alignment with the corresponding root socket longitudinal axis when placing the implant I into the root socket bone.

The surgical guide sleeves 166 may also have a depth limiting feature configured to limit an insertion depth of the implant I. For instance, a counterbore 180 may be defined at a bottom interior end of each of the surgical guide sleeves 166 that limits the depth of a surgical implant tool T when driving an implant I. In other words, axial movement of the surgical implant tool T is stopped by the counterbore 180, preventing the surgical implant tool T from driving the implant I deeper into the root socket. In this manner, the implant can only be driven into the bone at a certain depth, such as at a depth that locates the collar of the implant generally above the outer cortex layer of the bone at least partially in the gingiva layer.

A surgical guide formed in accordance with the systems and methods disclosed herein may be designed and fabricated using a tooth socket implant locating step, a virtual implant placement step, a surgical guide design step, and a fabrication step. Generally, the tooth socket implant locating step may include determining which of the patient's tooth sockets are the intended locations of the implants. The virtual implant placement step may generally include interacting with a digital design platform to digitally place each of the implants in a digital representation of the patient' replacement arch, thereby defining a location of each sleeve of the surgical guide. The surgical guide design step may include designing a body of the surgical guide and defining additional aspects of the sleeves. Finally, a fabrication step may include making a physical version of a surgical guide based on the digital design.

Each of the steps will be further described below. For ease of description, reference will be made to the surgical guide 150 and the dental bridge 100 described herein. However, it should be appreciated that the design and fabrication steps may be used to create any suitable surgical guide for use in placing implants for any suitable full arch dental bridge formed in accordance with the systems and methods disclosed herein, such as dental bridge 200. Moreover, although the steps are described in a particular order, it should be appreciated that any suitable order of steps may be used.

The tooth socket implant locating step, which may include determining which of the patient's tooth sockets are the intended locations of the implants, will first be described. As noted above, each of the implants for supporting placement of a dental bridge 100 on a patient's replacement arch are optimally placed in a post-extraction root socket of the replacement arch. One or more implant placement factors or strategies may be considered for determining which of the patient's tooth sockets are optimal for implant placement.

For instance, an implant placement strategy may include locating implants in suitable tooth sockets such that there is sufficient canine to molar spread (e.g., good anterior-posterior distance). According to known engineering principles and techniques used in the industry for dental bridge stability and balance, sufficient canine to molar spread provides sufficient load transfer paths suitable for transferring biting forces from the bridge to the implants. In other words, sufficient canine to molar spread allows for optimal occlusal forces (chewing forces) to be transmitted from the tooth portions of the bridge to the socket-placed implants. Suitable load paths supported by sufficient canine to molar spread thus helps prevent the bridge from breaking and helps prevent complications with the implants (e.g., loose implants, sinus problems, peri-implantitis, etc.).

Generally, four to six tooth or socket sized implants are used to secure the dental bridge to the preserved ridge with sufficient canine to molar spread. For instance, in the examples shown in FIGS. 17A and 17B, four implants are placed into four corresponding sockets for each upper and lower arch for a full mouth replacement. Preferably, first, second, third, and fourth replacement arch tooth sockets are designated as intended locations of implants, and each of the replacement arch tooth sockets designated as intended locations of implants are adjacent to a replacement arch tooth socket that is not designated as an intended location of an implant. In this manner, the four implants can provide sufficient canine to molar spread to support the full arch, dental bridge.

The number and socket location of each of the implants may also depend on other implant placement factors or strategies. For instance, implant placement strategy may include whether a root of a tooth is disease free and/or whether all four walls of a tooth root socket (e.g., the 360-degree enclosed wall of the socket) are substantially intact. Sufficient bone must surround the implant to allow for osseointegration of the implant. In that regard, implant placement strategy may include designating a root socket having a sufficient thickness of bone surrounding the root socket.

Other factors considered for implant placement strategy may include whether the tooth root socket is a sufficient distance from significant anatomical structures, such as a sinus cavity and an inferior alveolar nerve. For instance, if an implant would be more than 3-4 mm from a sinus cavity and more than 2 mm from an inferior alveolar nerve, it is likely considered a safe distance.

If a desired tooth socket has insufficient bone, is too close to significant anatomical structures, etc., implant placement strategy can include moving the implant location one tooth (socket) mesially and/or planning to place an additional implant in the respective quadrant of the jaw. If there is insufficient bone between the maxillary sinus cavity and the posterior ridge, then an implant strategy may include using a short implant (e.g., of about 8 mm height and 4.3 mm width), wherein the apex of the implant engages the bony floor of the sinus cavity floor having condensed bone.

The tooth socket implant locating step may be performed during a preparatory step of the pre-prosthetic ridge preservation process. Generally, the pre-prosthetic ridge preservation process involves atraumatically extracting all the teeth of the patient's replacement arch to prepare the arch for the bridge. When a surgical guide is used, however, only the teeth defining post-extraction root sockets for implant placement may be extracted such that a tooth-borne surgical guide may be designed and used for implant placement in the post-extraction root sockets. In that regard, tooth socket implant location may be defined when preparing for or at the beginning of the pre-prosthetic ridge preservation process. After a tooth socket location for each implant is decided, the corresponding teeth may be atraumatically extracted in accordance with the principles discussed herein.

The virtual implant placement step will now be described. As noted above, the virtual implant placement step may generally include interacting with a digital design platform to digitally place each of the implants in a digital representation of the patient' replacement arch. Digital placement of each of the implants may include defining the precise type, location and orientation of the implants within the desired root sockets. The precise type, location and orientation of the implants is needed for defining a location of the corresponding sleeves of the surgical guide, which are later used for accurately placing the implants.

The virtual implant placement step may be carried out using one or more platforms available for surgical guide design and fabrication. For instance, one or more digital design platforms, such as the 3Shape™ TRIOS™ software platform, the Planmeca Romexis® platform, the Atomica.ai™ design platform, etc., may be used to carry out the virtual implant placement step as well as any other steps described herein.

Generally, a surgical guide design and fabrication platform may allow a user to digitally design aspects of the surgical guide with reference to a digital representation of the patient' replacement arch. In that regard, a surgical guide digital design platform may be configured to use at least one of intraoral scan images (which shows both the teeth and bone (hard tissue) and the gums (soft tissue)), CBCT scan images (shows only hard tissue), or other images of or data regarding the patient's replacement arch or a denture prosthetic for the arch.

The replacement arch images may be displayed (after any necessary processing) in a graphical user interface (GUI) for a surgical guide design platform. In some instances, at least two images, such as an intraoral scan image and a CBCT scan image of a patient's replacement arch, may be superimposed by the software or otherwise available simultaneously in a GUI such that various aspects of the surgical guide may be designed with simultaneous reference to the images.

Figure 17E:
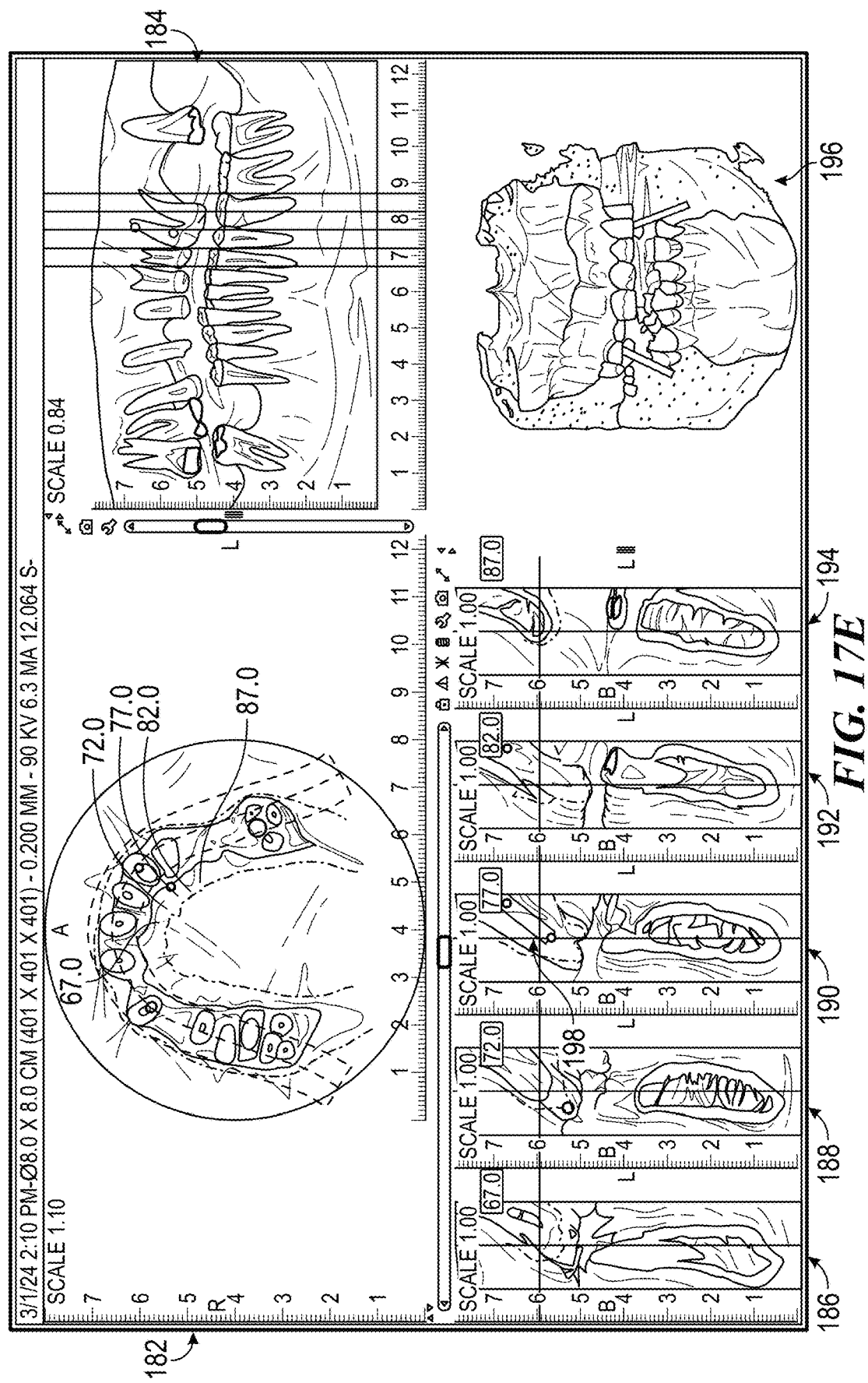
FIG. 17E depicts an exemplary graphical user interface (GUI) generated by a computing device that may be used for carrying out various surgical guide design steps for a replacement arch.
Figure 17F:
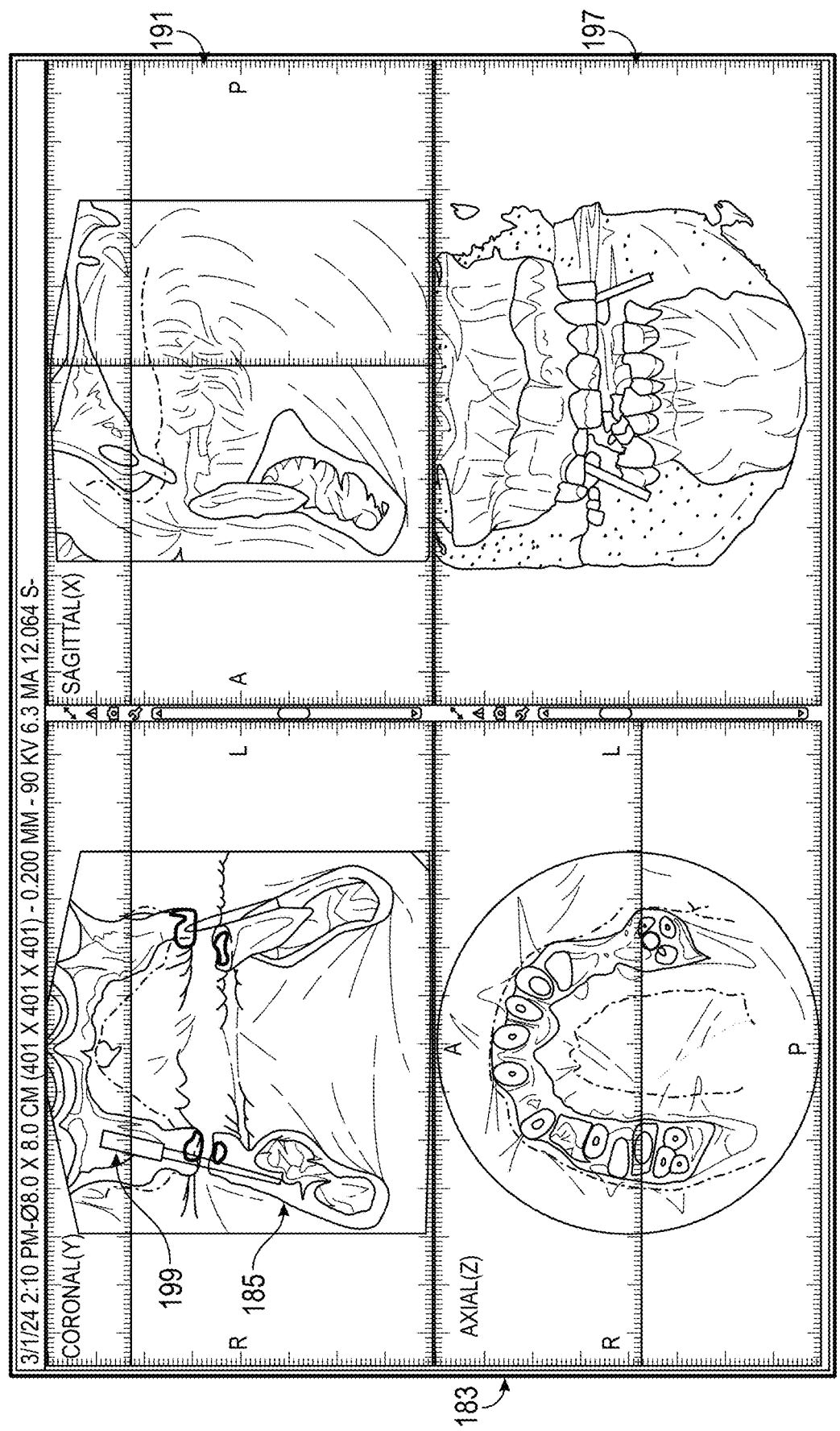
FIG. 17F depicts an exemplary graphical user interface (GUI) generated by a computing device that may be used for carrying out various surgical guide design steps for a replacement arch.

As a non-limiting example, FIGS. 17E and 17F show examples of a GUI for a surgical guide design platform including both CBCT scan images and an intraoral scan image of a patient's replacement arch. A CBCT scan image, as known in the art, shows hard tissue, such as bone and teeth, even if covered by soft tissue (similar to an X-ray). An intraoral scan image, as known in the art, shows both soft tissue (gingiva) and exposed hard tissue, such as a coronal portion of teeth.

Figure 17G:
FIG. 17G shows a 3D model of a replacement arch from a first perspective.
Figure 17H:
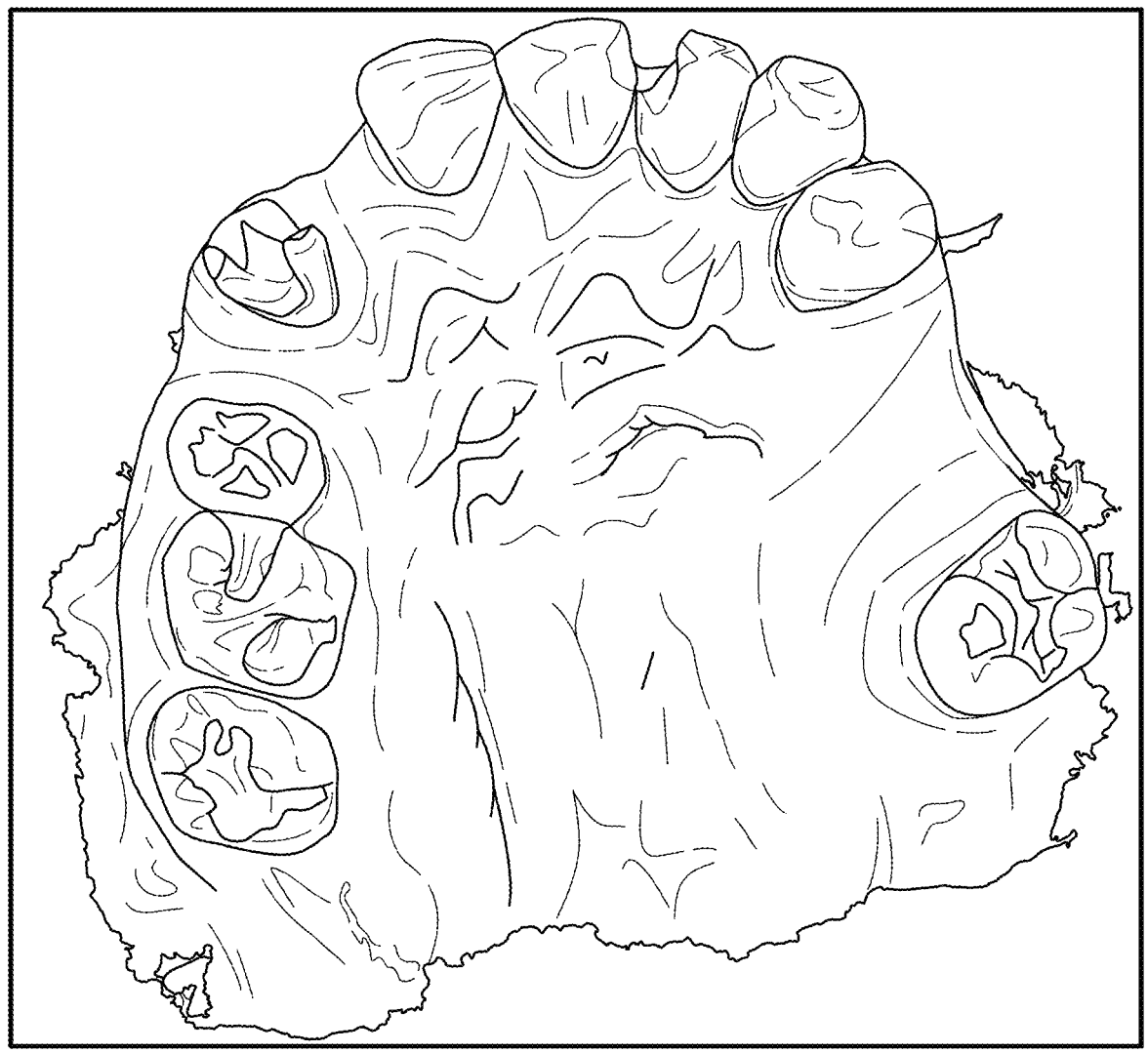
FIG. 17H shows a 3D model of a replacement arch from a second perspective.

The images shown in the surgical guide design platform GUI of FIG. 17E show various views of a CBCT scan or a superimposed intraoral and CBCT scan of the patient's replacement arch, antagonist arch, or portions thereof. For instance, going clockwise from an upper left corner of FIG. 17E, the surgical guide design platform GUI shows an axial view 182 of a CBCT scan of a patient's entire replacement arch, a panoramic view 184 of a CBCT scan of a patient's entire replacement arch and an antagonist arch, an isometric (skeletal) view 196 of a superimposed intraoral and CBCT scan of the patient's replacement arch and the antagonist arch, and individual (selected) teeth/socket sagittal views 186, 188, 190, 192, and 194 of a CBCT scan of a patient's replacement arch (taken along axial view section lines at 67.0, 72.0, 77.0, 82.0, and 87.0, respectively. For reference, an image of the intraoral scan of the patient's replacement and antagonist arch used for generating the isometric (skeletal) view 196 is shown in FIGS. 17G and 17H.

The images shown in the surgical guide design platform GUI of FIG. 17F show various views of a CBCT scan or a superimposed intraoral and CBCT scan of the patient's replacement arch, antagonist arch, or portions thereof. For instance, going clockwise from an upper left corner of FIG. 17F, the surgical guide design platform GUI shows a coronal view 185 of a CBCT scan of a portion of a patient's replacement arch, a sagittal view 191 of a CBCT scan of a portion of a patient's replacement arch, an isometric (skeletal) view 197 of a superimposed intraoral and CBCT scan of the patient's replacement arch and the antagonist arch, and an axial view 183 of a CBCT scan of a patient's entire replacement arch. An image of the intraoral scan of the patient's replacement and antagonist arch used for generating the isometric (skeletal) view 197 is shown in FIG. 17G.

As noted above, a CBCT scan image shows only hard tissue, such as bone and teeth. An intraoral scan image shows the soft tissue, but only exposed hard tissue (i.e., hard tissue not covered by soft tissue). However, in designing a surgical guide, it is helpful and typically necessary to know the location of the soft tissue, or the gums. In that regard, in the CBCT-only scan images of FIGS. 17E and 17F (specifically, 182, 184, 186, 188, 190, 192, 194, 183, 185, and 191), a drawing tool, superimposing tool, etc. may be used to define an outline of the soft tissue, such as the gums. The gum outline may be created by digitally aligning or superimposing a CBCT scan with a corresponding intraoral scan, such as by aligning or matching the positions of the coronal portions of the teeth, which is shown in both the CBCT scan and the intraoral scan. A user may then trace around the gum tissue outline in the superimposed image with a tracing/drawing tool. Thereafter, the intraoral scan can be digitally removed from the superimposed image, leaving only the CBCT scan image with the gum outline. In this manner, the gum outline can be seen in the CBCT scan image without obscuring the CBCT scan image with a superimposed image of the intraoral scan. It should be appreciated that any of the foregoing steps may instead be performed automatically with a suitable software program.

A user may interact with various views of the patient's replacement arch shown in the surgical guide design platform GUI to carry out the virtual implant placement step. For instance, one or more tools of the surgical guide design platform may allow a user to define a type, location, and orientation of each implant within the replacement arch bone. As non-limiting examples, the user may access an implant selection tool, a tooth/socket selection tool, an implant stamping tool, a graphic design drag and drop tool, a measurement tool, a tracing/drawing tool, a highlighting tool, or the like, to define a type, location, and orientation of each implant within a designated root socket.

In one design step, a user may select a type of socket-based implant to be used (such as from a drop-down list) based on one or more factors, such as a measurement of bone surrounding the intended root socket, an implant brand, an implant material, or other factors. After a type of socket-based implant is selected, the user may interact with a tooth/socket selection tool to select the desired tooth socket for placement of that selected socket-based implant. For instance, a user may click on an area in the replacement arch axial view 182 and/or on an area in a replacement arch panoramic view 184 to define a section line for displaying a detailed tooth socket. Upon selection, a detailed image of the tooth socket may be presented on the surgical guide design platform GUI. For instance, the selected root socket may be displayed in at least one of the socket teeth/socket sagittal views 186, 188, 190, 192, and 194 and/or the coronal view 185 or sagittal view 191 of a CBCT scan of a portion of a patient's replacement arch.

With a sagittal view or other suitable depiction of the selected tooth socket shown in an image, such as in one of the teeth/socket sagittal views 186, 188, 190, 192, and 194 and/or the coronal view 185 or sagittal view 191 of a CBCT scan of a portion of a patient's replacement arch, a user may place an implant graphical representation in a desired area of the root socket. The implant graphical representation may be placed on the image of the root socket with a suitable tool, such as a stamping tool, a graphic design drag and drop tool, etc. For instance, the user may drag a graphical image of an implant from a window of the GUI onto an image showing a sagittal view of the desired tooth root. In other examples, the user may designate an initial placement of the selected implant with a tracing/drawing tool or another type of tool.

The teeth/socket sagittal view 190 shows an exemplary implant graphical representation 198 virtually placed in the tooth socket. Upon placement of the exemplary implant graphical representation 198 in the desired teeth/socket sagittal view, the implant graphical representation may appear within other views, such as in the axial view 182 and the panoramic view 184, and/or the isometric superimposed view 196.

The coronal view 185 of a CBCT scan of a portion of a patient's replacement arch similarly shows an exemplary implant graphical representation 199 virtually placed in the tooth socket. Upon placement of the exemplary implant graphical representation 198 in the coronal view 185, the implant graphical representation may appear within other views, such as in the sagittal view 191, the axial view 183, and/or the isometric superimposed view 197.

With a graphical image or other representation of the implant initially placed in the tooth socket, the user may proceed to use other digital design tools to adjust the location and orientation of the implant. For instance, with reference to the exemplary implant graphical representation 198 shown in the teeth/socket sagittal view 190, the user may use one or more tools to move the exemplary implant graphical representation 198 up, down, left right, and/or diagonally relative to the socket. The user may also use one or more tools to move the exemplary implant graphical representation 198 about an axis transverse to the implant longitudinal axis to substantially align the implant longitudinal axis with the tooth socket axis. The same or similar steps can be carried out for precise placement of each implant in a corresponding tooth socket.

Exemplary aspects of the surgical guide design step, which may include designing a body of the surgical guide and defining additional aspects of the sleeves, will now be described. In some examples, a user may interact with various images of the patient's replacement arch (and optionally the antagonist arch) shown in the surgical guide design platform GUI to design the digital design of the surgical guide body 160 and the surgical guide sleeves 166. For instance, one or more tools of the surgical guide design platform may allow a user to designate the size, length, shape, etc., of the digital design of the surgical guide body 160.

As an example, in the axial views 182 and 183 of the patient's replacement arch, a user has generally outlined the soft tissue of the entire replacement arch, such as with a drawing tool. Such an outline of the soft tissue may be used as an aid to designate a general size and shape of the digital design of the surgical guide body 160.

For instance, a user may define the arc length of the digital design of the surgical guide body 160 to be substantially the same arc length as the patient's replacement arch. Similarly, a user may define the overall size and/or height of the digital design of the surgical guide body 160 to be substantially the same arc length as the patient's replacement arch.

A user may designate a size, length, shape, etc., of the digital design of the surgical guide body 160 by highlighting a relevant portion of the patient's replacement arch in a GUI image, such as with a highlighting tool. For instance to designate the overall height of the digital design of the surgical guide body 160, a user may highlight from an incisal/occlusal edge of the teeth to a buccal portion of the gums of the patient's replacement arch, to. A user may similarly highlight a portion of the palatal side of the gums and teeth. In other examples, a size designation tool may be used to define the height of the digital design of the surgical guide body 160, such as with markers, a spanning tool, etc. In any event, a minimum thickness, height, or overall size of the digital design of the surgical guide body 160 may be designated by the digital design platform to support the height and thickness of the surgical guide sleeves 166 in the digital design.

An interior portion of the digital design of the surgical guide body 160 may also be contoured to engage teeth of the patient's replacement arch that have not been extracted, while at the same time engaging or being positioned adjacent to the gums of the extracted teeth. The surgical guide body 160 may be designed to tightly engage or mate with teeth and/or gums of the patient's replacement arch. In this manner, and as noted above, the surgical guide 150 is held tightly in place relative to the replacement arch as the implants are being placed. In some examples, the digital design platform may be configured to automatically, digitally define the interior contour of the surgical guide body 160. The interior contour of the surgical guide body 160 may be based on the known contour of the teeth and gums of which the surgical guide body 160 will cover/engage.

It should be appreciated that any suitable methods known in the art may also/instead be used for defining the size, length, shape, contour, etc., of the digital design of the surgical guide body 160. In some examples, one or more of the steps and techniques described above for designing a surgical guide 150 may be carried out automatically by a module of the surgical guide design platform, such as in reference to the patient's replacement arch (and optionally the antagonist arch) represented in the views of the surgical guide design platform GUI.

In some examples, one or more of the steps and techniques described above for designing a surgical guide 150 may be carried out automatically with artificial intelligence, such as by executing one or more machine learning models on a computing device (e.g., a computing device configured to run a digital design platform such as those described herein, and/or a computing device in communication therewith). For instance, one or more machine learning models may be used to output a digital design for the surgical guide 150 using information regarding the patient's replacement arch (e.g., teeth and gum profile, which of the patient's tooth sockets are selected for implant placement, etc.) as input.

The fabrication step, which may include making a physical version of a surgical guide based on the digital design, will now be described. Initially, the fabrication step may include creating fabrication instructions for fabricating the surgical guide body 160 with a fabrication machine, where in the instructions are based on the digital design created for the surgical guide. As noted above, in some examples, the surgical guide body 160 is fabricated using at least one of stereolithography, selective laser sintering, milling, and 3D printing technologies. In that regard, the digital design platform may be configured to create and output fabrication instructions (e.g., instructions for printing, milling, sintering, etc.) based on the digital design. Any suitable method of creating and outputting fabrication instructions, as well as the method of fabricating the physical version of a surgical guide body 160 based on the digital design, may be used.

The fabrication step may further include placing the surgical guide sleeves 166 in the fabricated surgical guide body 160. In that regard, the surgical guide body 160 may be fabricated (based on digital design instructions) to include markers, posts, or other suitable structure supportive for locating the surgical guide sleeves 166 within the surgical guide body 160. In some examples, and as is sometimes done in the industry, the surgical guide body 160 may be fabricated with posts extending from an outer surface of the body that are substantially aligned within the implant longitudinal axis when the surgical guide body 160 is secured on the replacement arch. The posts may be used to drill into the surgical guide body 160 or otherwise secure the surgical guide sleeves 166 within the body along that implant longitudinal axis. The fabrication step may include any other finishing steps needed to prepare the surgical guide 150 for use.

Figure 17I:
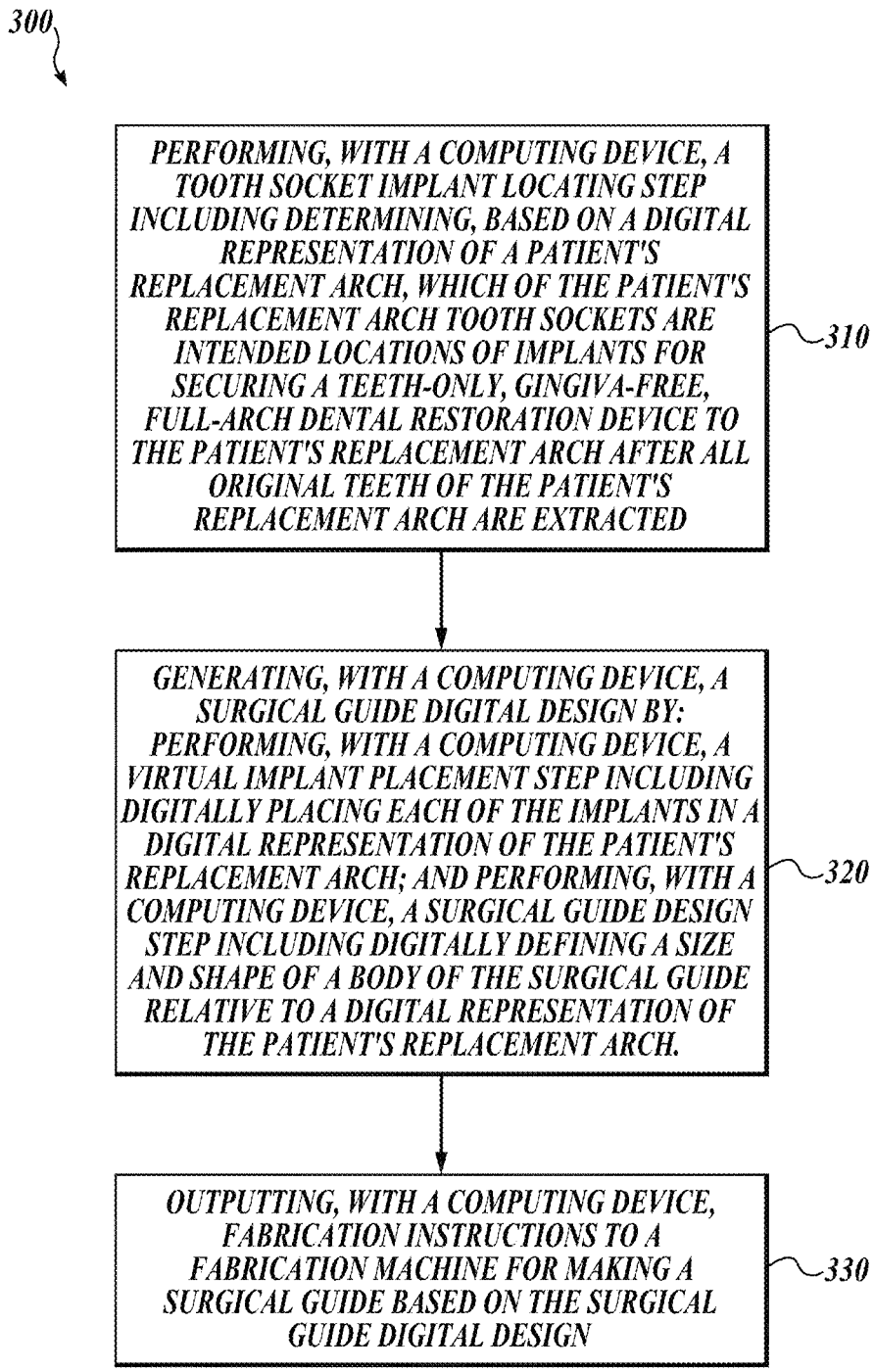
FIG. 17I is a flowchart that illustrates an exemplary method of making a surgical guide configured for placing implants in a patient's replacement arch to support a teeth-only, gingiva-free, full-arch dental restoration device, as described herein.

FIG. 17I is a flowchart of an example method 300 for making a surgical guide configured for placing implants in a patient's replacement arch to support a teeth-only, gingiva-free, full-arch dental restoration device, as described herein. In that regard, the method 300 may be used to create a surgical guide 200 or similar. Moreover, the method 300 may be carried out at least in part by one or more suitable computing devices that support a digital design platform or any computing device (including any devices, such as scanners, machines, etc.) in communication therewith.

At step 310, the method 300 may include performing, with a computing device, a tooth socket implant locating step. As discussed above, the tooth socket implant locating step may include determining, based on a digital representation of a patient's replacement arch, which of the patient's replacement arch tooth sockets are intended locations of implants for securing a teeth-only, gingiva-free, full-arch dental restoration device to the patient's replacement arch after all original teeth of the patient's replacement arch are extracted. For instance, one or more implant placement factors or strategies may be considered, such as whether there is sufficient canine to molar spread, whether the root socket is disease free, whether the walls of the root socket are intact, whether the tooth root socket is a sufficient distance from significant anatomical structures, etc. The tooth socket implant locating step may be performed during a preparatory step of the pre-prosthetic ridge preservation process, such as before any teeth are extracted.

At step 320, the method 300 may include generating, with a computing device, a surgical guide digital design. Generating the surgical guide digital design may include performing, with a computing device, a virtual implant placement step including digitally placing each of the implants in a digital representation of the patient's replacement arch. The socket sagittal view 190 shown in the GUI of FIG. 17E shows an exemplary implant graphical representation 198 virtually placed in the tooth socket. As discussed above, digital placement of each of the implants may include defining the precise type, location and orientation of the implants within the desired root sockets. The precise type, location and orientation of the implants is needed for defining a location of the corresponding sleeves of the surgical guide, which are later used for accurately placing the implants.

Generating the surgical guide digital design may include performing, with a computing device, a surgical guide design step including digitally defining a size and shape of a body of the surgical guide relative to a digital representation of the patient's replacement arch. For instance, a user may interact with various images of the patient's replacement arch shown in a surgical guide design platform GUI to design the surgical guide body and the surgical guide sleeves. For instance, one or more tools of the surgical guide design platform may allow a user to designate the size, length, shape, etc., of the surgical guide body of the surgical guide digital design.

At step 330, the method 300 may include outputting, with a computing device, fabrication instructions to a fabrication machine for making a surgical guide based on the surgical guide digital design. Initially, the fabrication step may include creating fabrication instructions for fabricating the surgical guide body with a fabrication machine, wherein the instructions are based on the digital design created for the surgical guide. The fabrication step may further include placing the surgical guide sleeves in the fabricated surgical guide body.

A completed surgical guide 150 may be used to place implants in the patient's replacement arch along the root socket longitudinal axis at a preferred depth, as described above. After the implants are placed, any remaining teeth may be extracted. After a suitable amount of time needed for implant osseointegration and gingiva/bone healing, the dental bridge 100 may be secured on the replacement arch, as described herein.

As noted above, in some examples, the implants are installed without the aid of a surgical guide. In such an example, all teeth of the patient's replacement arch may be extracted before implant placement.

Regardless of whether a surgical guide is used, all teeth may be extracted after implant placement to prepare the patient's replacement arch for bridge placement. After the implants are placed, all teeth are extracted, and during osseointegration of the implants into the patient's bone, the patient may wear dentures as the primary means of replacement teeth. In that regard, the dentures are adjusted as needed to ensure there is no interference with the healing caps on the implants. The patient may wear dentures a sufficient amount of time to allow for osseointegration of the implants (e.g., 3-6 months) within the existing bone. Osseointegration of the implants, or integration of the implants with existing bone in the jaw, typically occurs when the tissue and bone surrounding the implants have sufficiently healed.

After osseointegration, each implant axis, which is substantially the same as the corresponding tooth socket axis, is determined for designing a custom dental bridge 100. The dental bridge 100 is custom in that it will align and mate with a patient's implants having an implant axis that are unique to that patient's corresponding tooth socket axes. To measure the implant axis of each implant, healing caps may be removed from the implants and replaced with scan bodies, and digital and actual impressions may be taken to capture the angulation of the implants and the naturally shaped gingival ridge achieved by the atraumatic extractions.

Sometimes, during the time necessary for gingiva/bone healing and for osseointegration of implants to occur, a bacterial biofilm (plaque) and calculus (calcified plaque) may build up over the implant healing caps and/or in the surrounding area of the gingival tissue. Such a build-up can cause gingival inflammation around the top part of the implant (e.g., the collar, neck, and/or platform of the implant), making it difficult for the implant to mate with a corresponding abutment during bridge placement. In that regard, corresponding steps may be taken to clean or debridge the top part of the implant (e.g., the collar), including the healing cap, to recover the implant. Steps may also be taken to reduce inflammation in the gingival tissue surrounding the implant.

For instance, the build-up on the top (e.g., collar and/or healing cap) of the implant and/or surrounding the implant may be cleaned or otherwise removed ("debridged") using standard dental hygiene techniques, such as using a dental pick, a brush, an ultrasonic cleanser, etc. Sufficient steps may be taken to fully cleanse the area for sufficient mating with the abutments received in the dental bridge.

By removing build-up and/or cleaning the implant (e.g., collar and/or healing cap) and its surrounding gingival tissue, optionally in combination with topical and/or oral anti-inflammatory treatments, the inflammation in the surrounding gingival tissue eventually subsides. However, it can be appreciated that the time needed for inflammation reduction may require one or more additional visits before digital and actual impressions may be taken.

In that regard, in some examples, the inflammation in the gingival tissue around the top part of the implant (e.g., collar and/or healing cap) may be treated using a high-powered laser, such as the Waterlase iPlus all-tissue laser described herein. The water-energized laser beam can be directed at the inflamed tissue, and energy of the laser interacts with biological components of the tissue to reduce inflammation. In one example, the laser may be used at a lower power (W) and high frequency (Hz) setting for effectively reducing inflammation in the gum tissue.

In some examples, the build-up on the top of the implant (e.g., collar and/or healing cap) and/or surrounding the implant may be cleaned or otherwise removed ("debridged") using a high-powered laser, such as the Waterlase iPlus all-tissue laser described herein. The water-energized laser beam can be directed at the build-up, and energy of the laser excites molecules in the build-up, causing it to break up. In one example, the laser may be used at an implant debridgement setting for effectively removing the build-up. If tissue inflammation is present, the high-powered laser may also be used to treat and reduce the inflammation, as described above.

Sometimes, during the time necessary for gingiva/bone healing and for osseointegration of implants to occur, gingival tissue grows over the top of the implant healing cap, and the implant needs to be recovered. The implant is recovered by removing the gingival tissue overgrowth.

In one example, the gingival tissue overgrowth is removed using standard dental tissue removal/contouring techniques. For instance, after numbing the area with a local anesthetic, a scalpel blade may be used to cut the gingival tissue. Standard practices may then be used to control bleeding and to support tissue recovery. As can be appreciated, the extra time needed and discomfort causes by numbing the area, controlling bleeding, and allowing for healing adds significant time and stress to the overall process. Moreover, in some instances, when bleeding cannot be controlled, the next steps of applying scan bodies to the implants and performing intraoral scanning may need to be delayed. Bleeding can cause distortion in the scan data and therefore affect the accuracy of the scan data.

Thus, in some examples, the gingival tissue overgrowth may be removed using a high-powered laser, such as the Waterlase iPlus all-tissue laser described herein. The water-energized laser beam can be directed at the tissue overgrowth, and energy of the laser excites molecules in the tissue to cut through the tissue. In that regard, the laser may be used to make one or more incisions in the tissue to cut away or otherwise remove portions covering the implant/ healing cap and in any surrounding areas. Such tissue removal can be done with little to no local anesthetic, seeing as a high-powered laser, such as the Waterlase iPlus all-tissue laser causes little to no pain as it penetrates tissue. Thus, as noted above, use of a high-powered laser, such as the Waterlase iPlus all-tissue laser described herein, supports a natural, gentle, atraumatic approach to tooth extraction and ridge preservation.

Moreover, as noted above, a high-powered laser, such as the Waterlase iPlus all-tissue laser cauterizes the tissue as it cuts through the tissue. Thus, bleeding is substantially minimized or controlled when using a laser to remove overgrown tissue. In that regard, scan bodies may typically be placed on the implants on the same day of tissue removal, and accurate intraoral scan data may be obtained.

The dental bridge 100 for that patient may be designed and created using a suitable process, such as the system and method described in U.S. application Ser. No. 18/631,602, entitled "System and Method for Full Arch, Teeth-Only Bridge Design", filed Apr. 10, 2024, incorporated herein. Aspects of the dental bridge 100, such as the design of the bridge for securing to a patient's jaw prepared using the full arch dental restoration device arch preparation system and method described herein or another suitable process, will be described below.

Detailed Exemplary Aspects of the Dental Bridge

A dental bridge 200 formed in accordance with exemplary aspects of the present disclosure will now be described with respect to FIGS. 18-24. Although not identically shown in FIGS. 18-24, each of the dental bridges shown in FIGS. 18-24 (as well as FIGS. 25-28) is identified by reference numeral 200 for ease of description. The dental bridges 200 shown in FIGS. 18-28 are substantially identical to and/or incorporate the features described above with reference to the dental bridge 100, and vice versa.

The dental bridge 200 is generally a full-arch (e.g., fourteen teeth, twelve teeth, or ten teeth) dental bridge made from zirconia or a similar material to provide the strength of natural teeth. The dental bridge 200 is made without artificial gingiva such that it can attach to socket-based implants for a full mouth teeth replacement. In that regard, the dental bridge 200 is generally configured to be secured to socket-based implants secured in a patient's jaw having teeth removed atraumatically, such as using the pre-prosthetic ridge preservation process described herein, or another suitable process.

Figure 18:
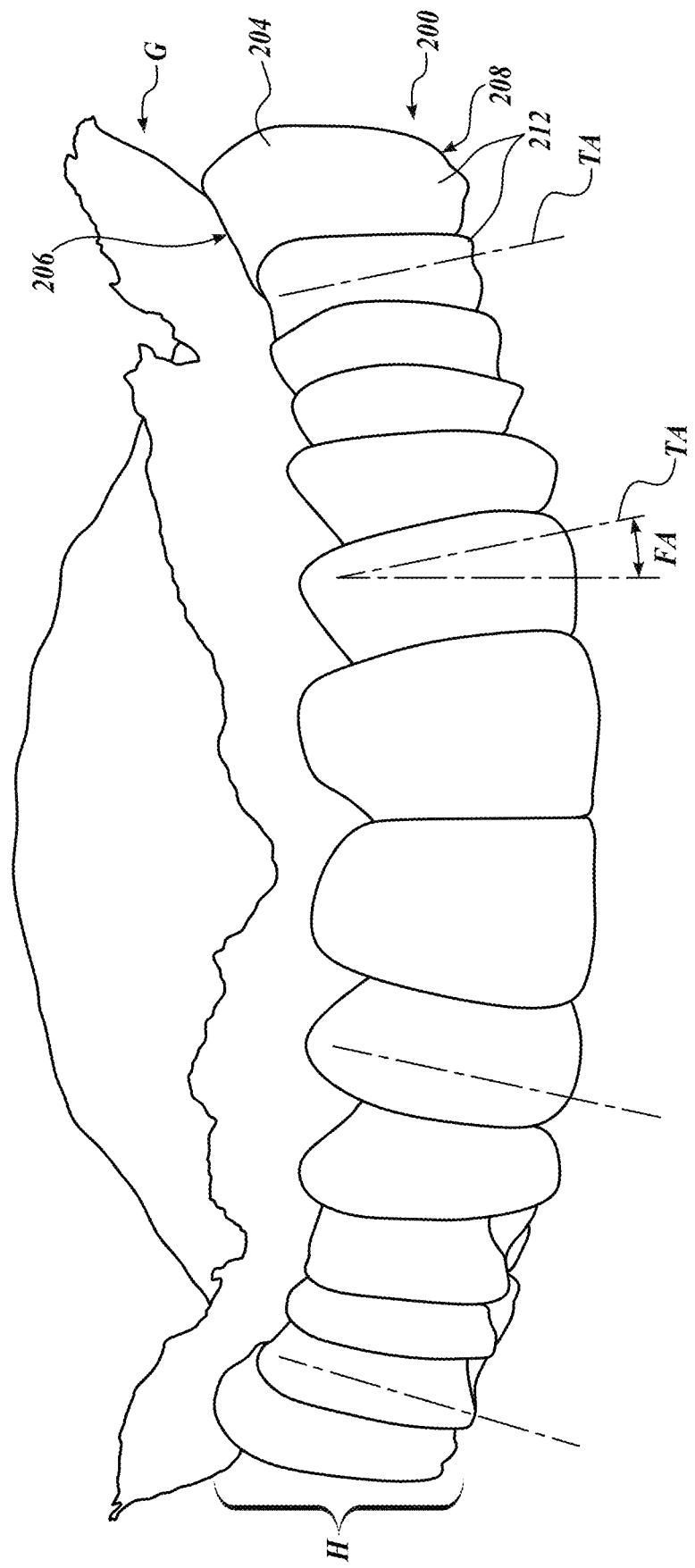
FIG. 18 depicts an isometric view of an example of a fourteen teeth dental bridge shown seated against a ridge/gingiva of a patient's upper jaw preserved in accordance with exemplary aspects of the pre-prosthetic ridge preservation process of FIG. 9.

FIG. 18 depicts an example of a fourteen teeth dental bridge 200 shown seated against the ridge/gingiva G of a patient's upper jaw. The dental bridge 200 includes a generally arc-shaped body 204 made from zirconia or a similarly strong, non-porous (e.g., non-staining), hygienic material to provide the strength of natural teeth while still being generally light weight. Along its height, the body 204 extends between a gingival side 206 and an occlusal/incisal side 208 to generally define a height H of the body 204 that is a height of natural teeth protruding from a gingival ridge.

The body 204 defines a plurality of teeth portions 212 extending along its arced length that are shaped and sized to generally mimic the teeth required for a full mouth teeth replacement. The dental bridge 200 is shown having fourteen teeth portions 212, including four incisors, two canines, four premolars and four molars. It should be appreciated that a fourteen teeth dental bridge for use with a patient's lower jaw would have similar features and will therefore not be separately described. Moreover, it should be appreciated that a ten or twelve teeth upper or lower dental bridge would have similar features and will therefore also not be separately described.

The gingival side 206 of the dental bridge 200 is configured to seat against a patient's gums G, which are left intact during the pre-prosthetic ridge preservation process, and which follow the contour of the patient's original bony ridge. In that regard, the dental bridge 200 is custom-made to fit the unique shape and contours of the patient's gum line defined by the preserved tooth sockets. When mated to the patient's original bony ridge, parallelism is substantially achieved between the interpupillary line (the line between the left and right pupils) and the occlusal plane (OP) of the patient (e.g., the average plane established by the incisal and occlusal surfaces of the teeth) as well as between the ala-tragus line (ATL) and the OP.

Further referring to FIGS. 19-20, exemplary aspects of the dental bridge 200 for allowing the bridge to fit the unique shape and contours of the patient's gum line defined by the preserved tooth sockets will now be described. Generally, the gingival side 206 of the dental bridge 200 has an ovate pontic contour that generally follows the gingival contour of the patient (e.g., the unique shape and contours of the patient's gum line defined by the preserved tooth sockets). In other words, the ovate pontic contour of the gingival side 206 of the bridge 200 is designed to substantially mate with the correspondingly-shaped residual tissue ridge of the gums G preserved during the pre-prosthetic ridge preservation process. In that regard, each tooth portion 212 is generally of an ovate pontic shape to define an ovate pontic contour on its gingival side 206. As can be appreciated, the ovate pontic shape of each tooth portion 212 substantially mimics the shape of the natural root and crown for that tooth.

Each tooth portion of a bridge, as is well known in the industry, has a middle section, a gingival section extending from the middle section to the gingival side of the body (e.g., gingival side 206), and an occlusal/incisal section extending from the middle section to the occlusal/incisal side of the body (e.g., occlusal/incisal side 208). The ovate pontic portion is defined on each tooth portion on the gingival section of the body.

The ovate pontic portion of each tooth portion substantially conforms in shape to the corresponding post-extraction tooth socket defined by keratinized gingiva covered interdental and interseptal bone of the patient after a tooth is extracted. In that regard, the ovate pontic portion is configured to seal against the keratinized gingiva when the ovate pontic portion is engaged with the corresponding post-extraction tooth socket.

FIGS. 19A-19C depict illustrations of a dental bridge 200 as well as individual teeth portions 220 and 223 showing the generally ovate pontic contour of the ovate pontic portion on the gingival side 206 designed to substantially mate with the correspondingly shaped residual tissue ridge of the gums G. Specifically, FIG. 19A depicts a front planar view of a dental bridge 200 showing an ovate pontic contour of an ovate pontic portion on a gingival side 206 of the bridge body 204. As can be seen, the ovate pontic portion on the gingival side 206 of each tooth portion 212 of the bridge body 204 has an ovate pontic contour or a generally ovate pontic shape that generally corresponds to the shapes of the depressions left in the residual tissue ridge of the gums G. FIG. 19B shows a side (lateral) view of an incisor tooth portion 220, and FIG. 19C shows a side (lateral) view of a molar tooth portion 222, each having an ovate pontic portion on its gingival side 206 with an ovate pontic shape/contour that substantially matches the contour of the residual tissue ridge R.

The ovate pontic shapes of each tooth portion may be either generally convex, concave, or a combination thereof to substantially match the bumps, valleys, and contours of the residual tissue ridge. For instance, FIG. 20 shows a bridge 200 having an ovate pontic shape/contour on the ovate pontic portion on the gingival side 206 of its body 204, with a first molar tooth portion 222 generally having a convex ovate shape and a second molar tooth portion 224 having a generally concave ovate shape.

Figure 21:
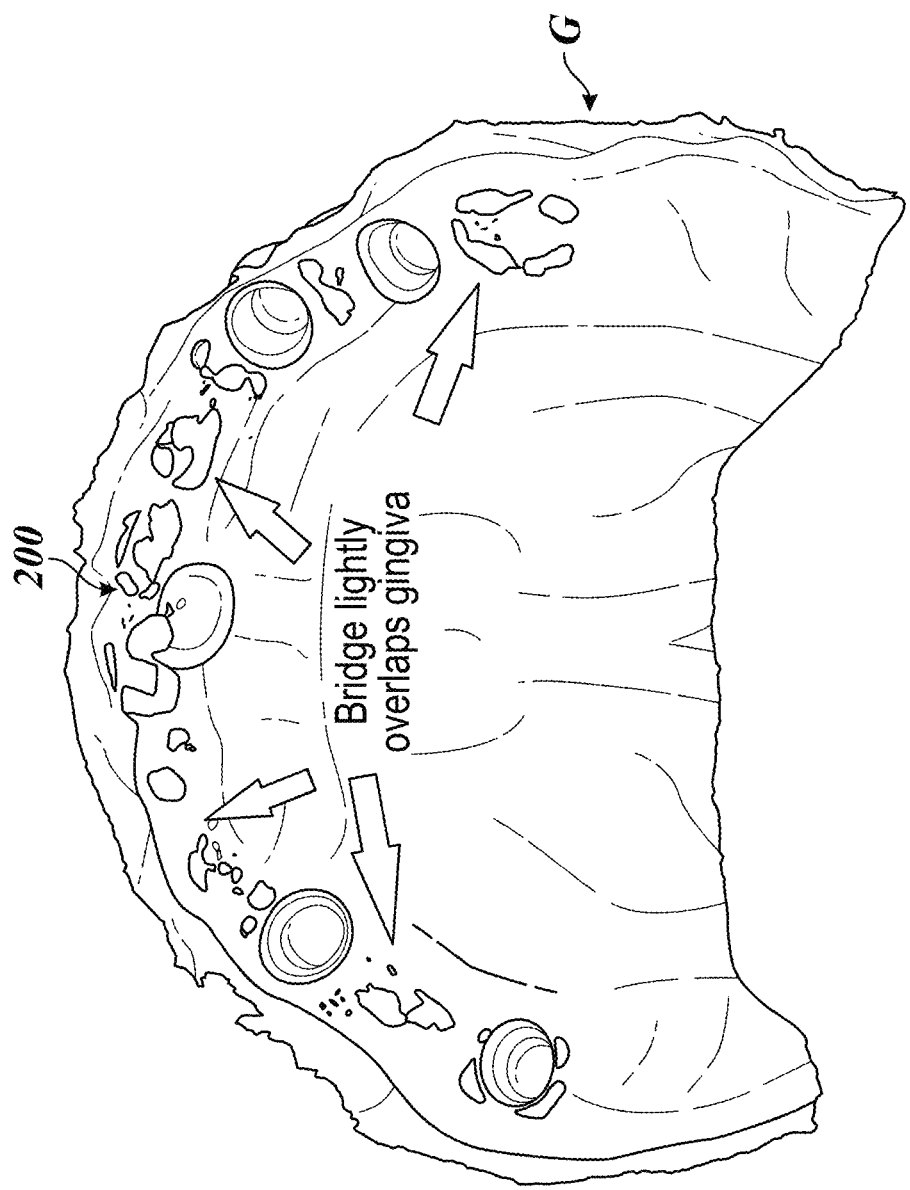
FIG. 21 depicts a bottom view of an upper jaw of a patient showing portions of a dental bridge formed in accordance with exemplary aspects of the present disclosure at least partially overlapping the gingiva of the patient.
Figure 22:
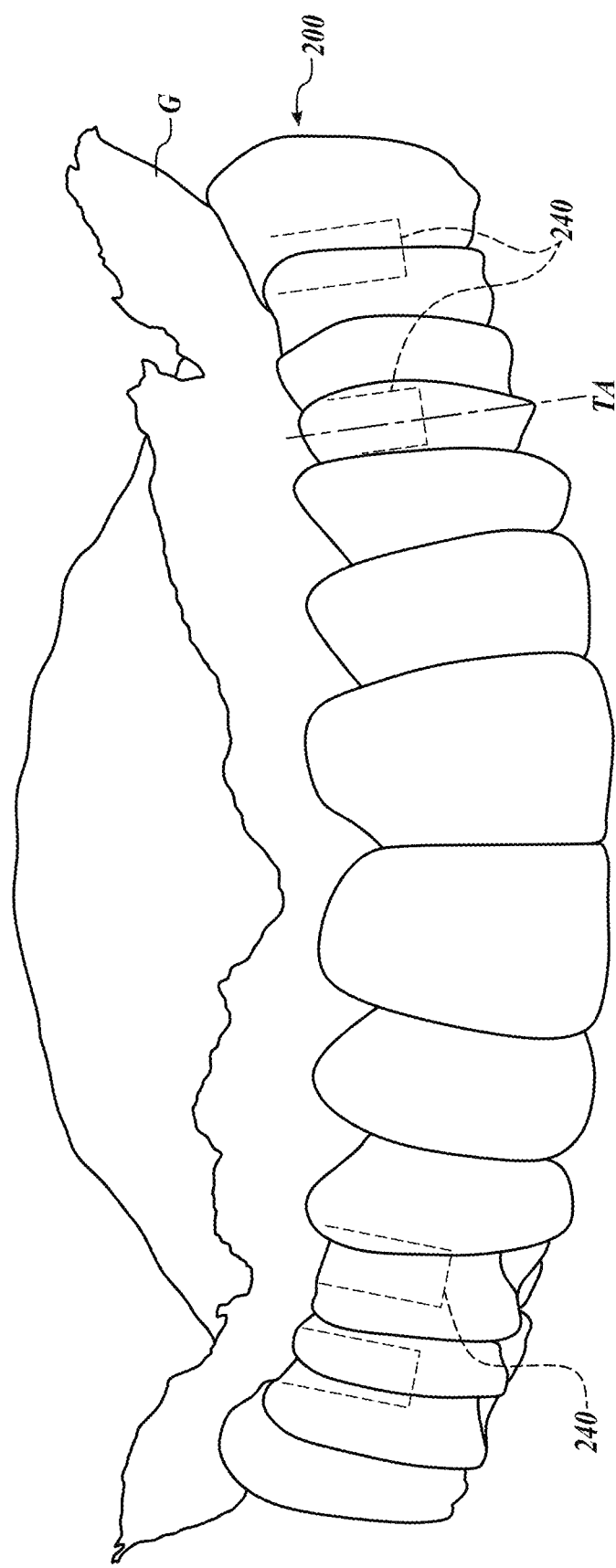
FIG. 22 depicts a front view of a dental bridge formed in accordance with exemplary aspects of the present disclosure shown secured to a patient's upper jaw.

Referring to FIG. 21, the ovate pontic shape/contour of the gingival side of bridge 200 defines a gingival interface that is configured to slightly overlap with or penetrate with the gingival surface of the gum G. Such overlap ensures a tight fit, with substantially no gap defined between the ovate pontic gingival interface of the dental bridge 200 and the gum G. As can be appreciated, any gaps or irregular surfaces would be difficult to clean.

For instance, prior art methods such as the All on 4 method cut down and flatten the bone, eliminating the tooth sockets entirely as well as major portions of the gingiva. As a result, the All on 4 bridge requires an artificial gum portion having a substantially flat bottom that must rest on the "bulldozed" bone/gingival surface. Resting a flattened bottom artificial gum portion against a flattened bone/gingival surface results in undercuts and hidden areas for food entrapment (see the gaps between the prosthetic P and the patient's gums in FIG. 7). By comparison, the dental bridge 200 formed herein ensures a tight fit between the bridge and the patient's gums.

Moreover, the All on 4 bridge must be significantly bigger to replace not only the original teeth, but the lost bone and gingiva. For instance, the prosthetic P shown in FIGS. 2-4 is about one-half inch in height (½"). By comparison, the dental bridge 200 has a height H that is only about one-eighth inch in height (⅛") when seated against a patient's gums (see FIG. 18).

Referring back to FIG. 18, the arc-shaped body 204 of the dental bridge 200 has an overall flared shaped to accommodate the anatomical shape of the patient's palette at the intersection of the gingiva. For instance, each tooth portion 212 has a tooth axis TA extending buccally/labially (and sometimes distally and/or mesially) from its gingival side 206 to the incisal/occlusal side 208 (e.g., the bottom of the bridge to the top of the bridge).

The tooth axis TA is generally the same as the longitudinal axis of the original teeth, and therefore, the tooth axis TA is generally the same as the longitudinal axis of the preserved tooth sockets and the implants placed into the sockets. The tooth axis TA is typically offset from a vertical axis by a flare angle FA. Generally, the flare angle is between 1-20° from a vertical axis, such as between 10-15° from a vertical axis, but it varies based on patient's palate and alveolar ridge shape.

Figure 20:
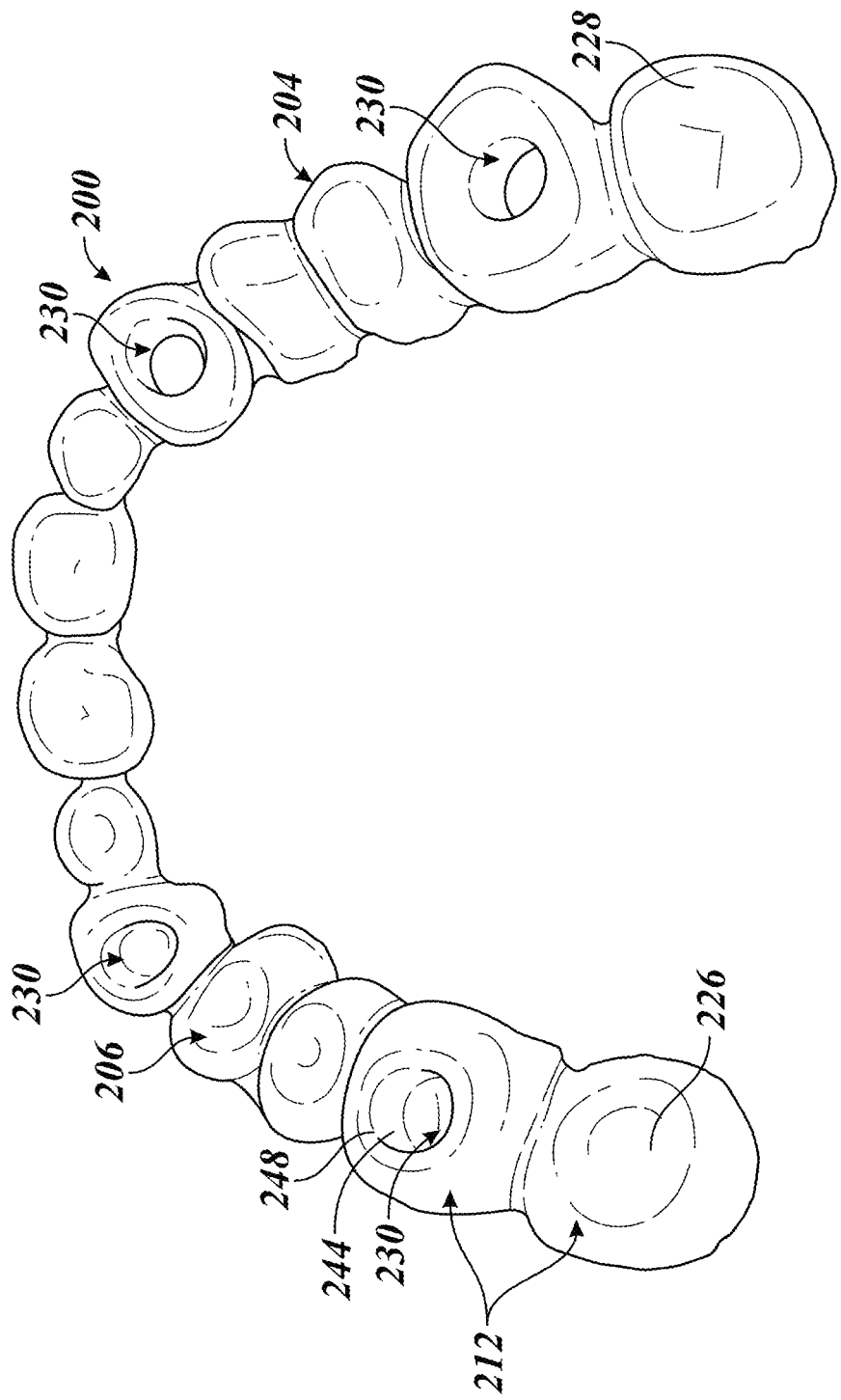
FIG. 20 depicts a bottom view of a dental bridge formed in accordance with exemplary aspects of the present disclosure.

Referring to FIG. 20, the dental bridge 200 includes a plurality of abutment holes 230 for receiving abutments/screws for mating to implants. Each abutment hole 230 is formed in a tooth portion 212 of the dental bridge 200 corresponding to a location of an implant. For instance, for the dental bridge 200 shown in FIG. 20, an abutment hole 230 is defined in the following tooth portions of the dental bridge 200: tooth #3 (upper right first molar), tooth #6 (upper right canine), tooth #11 (upper left canine), and tooth #14 (upper left first molar). In that regard, in the example shown, each tooth portion having an abutment hole is located adjacent to a tooth portion without an abutment hole. However, it should be appreciated that the abutment holes 230 may of course be defined in other tooth portions depending on the socket location of the implants.

Figure 23:
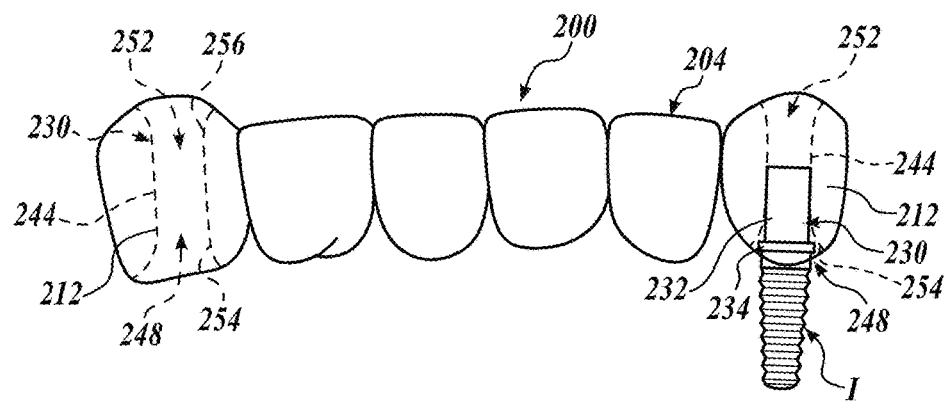
FIG. 23 depicts a front view of a dental bridge formed in accordance with exemplary aspects of the present disclosure, showing a cross-sectional shape of hidden abutment holes of the dental bridge.

In general, each abutment hole 230 is defined by a generally cylindrical through-hole 244 formed in a tooth portion 212 of the dental bridge 200 that extends between a gingival opening 248 and an incisal/occlusal opening (see incisal/occlusal opening 252 shown in FIG. 23). In some examples, the abutment hole 230 flares outwardly as it extends from an interior surface of the through-hole 244 toward the gingival or incisal/occlusal outer surface. In the depicted example, a first substantially smooth, curved, convexly shaped tooth portion interface 254 may extend between the gingival end of the through-hole 244 and the gingival outer surface of the bridge body 204 to define a gradually widened gingival opening 248. Similarly, a second substantially smooth, curved, convexly shaped tooth portion interface 256 may extend between the incisal/occlusal end of the through-hole 244 and the incisal/occlusal outer surface of the bridge to define a gradually widened incisal/occlusal opening 252. In this manner, sharp edges, which can cause tissue irritation and/or susceptibility to breakage and/or compromise fit or sealing against the gingiva, may be avoided.

The curved tooth portion interfaces 254 and 256 also help guide abutment components into engagement with the tooth portion 212. For instance, the curved tooth portion interface 256 at the incisal/occlusal opening 252 can help guide the abutment screws into engagement with the abutments. More specifically, an abutment screw shaft may be guided easily and smoothly along the curved surface of the curved tooth portion interface 256 at the incisal/occlusal opening 252 into an opening in a body 232 of the abutment 240 (see abutment screws extending from abutments 240 in FIG. 17C). Similarly, the curved tooth portion interface 254 at the gingival opening 248 can help guide the abutment body 232 into engagement with the through-hole 244. More specifically, the abutment body 232 may follow the path along the curved surface of the curved tooth portion interface 254 at the gingival opening 248 into the through-hole 244.

The abutment hole through-hole 244, which is generally an elongated cylindrical shape, has a diameter that is substantially the same size or slightly larger than a diameter of the abutment body 232. In this manner, the abutment body 232 may extend into the tooth portion 212 for securing the abutment to the bridge 200, as shown in FIG. 23. At the same time, the through-hole 244 has a diameter than is smaller than a diameter of a ring or skirt 234 of the abutment 240. In that regard, the abutment skirt 234 rests against the gingival opening 248, with the abutment body 232 extending into the abutment hole 230. The abutment skirt 234 may rest inside the gradually widened gingival opening 248 such that the skirt may be at least somewhat nested within the gingival side 206 of the bridge 200. In this manner, the abutment skirt 234 is substantially flush with the gingival side 206 of the bridge 200 when mated against the gingival opening 248.

However, as can be appreciated, the size (e.g., diameter), shape, and contour of each gingival opening 248 may differ based on the shape of the individual teeth portion 220. Accordingly, it should be appreciated that the abutment skirt 234 may be slightly recessed within the bridge body 204 or instead protrude slightly from the gingival side 206 of the bridge body to accommodate the contours of the bridge. Thus, when generally stating that the abutment skirt 234 is substantially flush with the gingival side 206 of the bridge 200, it includes any suitable location of the abutment skirt 234 relative to the gingival side 206 of the bridge 200 to accommodate mating of the abutments and implants (and therefore engagement of the bridge with the patient's preserved ridge) in the manners described herein.

Each abutment through-hole 244 is substantially coaxially aligned with the tooth axis TA of its tooth portion 212 (see FIG. 22), which is substantially aligned with the tooth socket axis of the corresponding post-extraction tooth socket, to enable the abutments 240 to be aligned with and mated with the corresponding implants extending along the tooth axis TA. Substantial axial alignment of the abutment through-hole 244 with the longitudinal axis of the implant allows a non-angulated abutment 240 to be received within the abutment hole 230 and secured to a socket-sized implant. In that regard, the abutment holes 230, the abutments 240, and the corresponding implants have a longitudinal axis that substantially matches the tooth axis TA to accommodate the flare of the patient's palette. Substantially axial alignment of the abutment holes 230, the abutments 240, and the corresponding implants with the tooth axis TA of the tooth portion 212 allows for optimal occlusal forces (chewing forces) to be transmitted from the tooth portions to the socket-placed implants.

As noted above, the tooth axis TA flares buccally/labially (and sometimes distally and/or mesially) from the gingival side 206 of the bridge to the incisal/occlusal side 208 of the bridge. In that regard, the abutments 240 collectively define an overall flared shape that helps retain the dental bridge 200 on the implants. In other words, the dental bridge 200 cannot substantially move axially along the abutments 240 due to the flared or non-vertical interface defined between the abutments 240 and the abutment holes 230. Accordingly, in addition to anatomically accommodating the shape of the patient's pallet, the flared shape of the dental bridge 200 and its corresponding features (e.g., the abutment holes 230, the abutments 240, and the corresponding implants) help retain the bridge in its restoration position against the patient's gums.

However, such flared or non-vertical interface defined between the abutments 240 and the abutment holes 230 means that, during installation of the dental bridge 200, the bridge typically cannot be simply placed over abutments that are screwed into the implants. Replacement teeth are typically installed on an implant by first placing an abutment on the implant, and then securing the tooth to the abutment. Accordingly, if the longitudinal axes of the abutment holes 230 and the abutments 240 are offset from vertical (e.g., they are not perfectly parallel to one another, but rather, they flare to match the vertically offset angle of the implants), the abutment holes 230 cannot be simultaneously aligned with the corresponding abutments 240 for receiving the abutments.

One solution for accommodating the flared or non-vertical interface defined between the abutments 240 and the abutment holes 230 would be to use angulated abutments with the implants. However, angulated abutments can cause undue stress on the bridge and/or the implants when transferring biting forces from the bridge to the implants. When using angulated abutments, the biting forces are not transferred along the axis of the implant, the abutment, and the tooth portion of the bridge. Rather, the biting force must pass through the angulated abutment, which has a longitudinal axis that is offset from the longitudinal axes of the implants and the bridge tooth portion. The dental bridge of the present disclosure accommodates the flared or non-vertical interface between the abutments and the abutment holes without compromising the mechanical strength and/or interface between the bridge and the implants.

Exemplary aspects of the dental bridge 200 configured to accommodate the flared or non-vertical interface defined between the abutments 240 and the abutment holes 230 without compromising the mechanical strength and/or interface between the bridge and the implants will now be described. In general, the dental bridge 200 is designed such that abutments may first be placed inside the vertically offset abutment holes 230, and then the dental bridge 200 may be placed into the patient's mouth and screwed down into the underlying implants.

As may best be seen by referring to FIGS. 20 and 23, the abutment holes 230 may be suitably shaped, sized, and contoured to mate with or otherwise receive the abutments 240 and to allow for securing the abutments to the corresponding implants. As noted above, each abutment hole 230 is defined by a generally cylindrically shaped through-hole 244 in a tooth portion 212 that extends between an outwardly extending gingival opening 248 in the gingival surface of the tooth portion and an outwardly extending incisal/occlusal opening 252 in the incisal/occlusal surface of the tooth portion.

The through-hole 244 may have a minimum and/or maximum circumference to suitably mate with or otherwise receive the abutments 240. The minimum and/or maximum circumference of the abutment through-hole 244 may be determined using standards well known in the art. For instance, the circumference of the abutment through-hole 244 may be determined using suitable CAD modeling software (e.g., the Ivoclar™ zirconia restoration platform) or other suitable technology based on the known circumference of the chosen abutments.

At the same time, the tooth portion 212 may be designed to have a sufficient size surrounding the abutment hole 230 to prevent any cracking or breakage of the tooth portion surrounding the hole. As can be appreciated, if the tooth portion 212 surrounding the abutment hole 230 was not sufficiently thick, the bridge body 204 would be prone to breakage in that area. More specifically, even when made from a strong material such as zirconia, the bridge body 204 can break under biting/chewing forces if it is insufficiently thick around the retaining abutments. In that regard, a tooth portion having an abutment hole 230 has a sufficient tooth portion thickness or a minimum amount of body material surrounding the entire circumference of the abutment hole 230. For instance, a minimum tooth portion thickness of about 2 mm defined by the body material (e.g., zirconia) may surround the through-hole 244. In some instances, the tooth portion 212 is intentionally enlarged to accommodate a sufficiently sized through-hole 244 (see enlarged tooth portion 213 shown in FIG. 27).

The abutment holes 230 may also be shaped, sized, and/or contoured to allow for alignment of and engagement of the abutments with the corresponding implants. When securing an abutment to an implant, the abutments are aligned with the implant, and then a screw is passed through an opening of the abutment and into a threaded opening of the implant. In that regard, the abutment holes 230 may be shaped, sized, and/or contoured to allow for alignment of the abutment screws with the threaded openings in the corresponding implants.

For instance, in the depicted example, the through-hole 244 may have a slightly larger inner diameter than an outer diameter of abutment body 232 to accommodate alignment of and installation of an abutment screw in a threaded opening of a corresponding implant. For instance, the through-hole 244 may have an inner diameter that provides sufficient clearance for aligning and installing (torquing) the abutment screws in the threaded openings of the implants. In other words, the through-hole 244 defines an opening of a sufficient diameter to allow for the abutment body 232 and the abutment screw received therein to move sufficiently laterally relative to the tooth axis TA to align the screw with the implant screw hole. In that regard, the through-hole 244 allows for sufficient "wiggle room" when inserting and aligning an abutment screw through the abutment body 232 and into the implant.

The diametrical size of the through-hole 244 may be defined at least in part by the size, shape, and type of the abutment, the abutment screw, and/or the implant used. For instance, the through-hole 244 may be designed to have a minimum inner diametrical opening along the length of the through-hole 244 that is larger than the abutment body 232 by a minimum amount, thereby allowing for sufficient lateral movement of the abutment body 232 and the abutment screws when aligning the abutment screws with the threaded openings in the implants.

At the same time, the through-hole 244 may be designed to have a maximum diametrical opening along the length of the through-hole 244 that is larger than the abutment body 232 by an amount to sufficient restrain the abutment body 232 with the through-hole 244 while allowing sufficient lateral movement for alignment. The through-hole 244 may be sized to define minimum and/or maximum clearance between an interior surface of the through-hole 244 and the abutment body 232 using known mechanical clearance standards and/or through experimental use.

In general, the radial clearance between the interior surface of the through-hole 244 and the abutment body 232 should generally not be larger than needed because it would unnecessarily remove material from the bridge tooth portion, comprising mechanical integrity. Moreover, an unnecessarily large gap between the interior surface of the through-hole 244 and the abutment body 232 would cause pooling of or an excessive use of adhesive material, such as cement, when securing the abutment body 232 to the dental bridge 200. Pooled or excess cement decreases the strength of the mechanical attachment between the dental bridge 200 and the implants.

The inventor has found that a radial clearance of about 1.00 mm between the interior surface of the through-hole 244 and the abutment body 232 along the length of the through-hole 244 provides sufficient lateral "wiggle room" when inserting/installing the abutment screws while sufficiently restraining the abutment body 232 in the abutment hole 230. Further, using a minimal radial clearance such as about 1.00 mm limits pooling of or excess use of cement between the abutment body 232 and the interior surface of the through-hole 244.

The through-hole 244 may have substantially the same inner diameter along its length. In other words, the radial clearance between the interior surface of the through-hole 244 and the abutment body 232 may be substantially the same along the length of the through-hole 244. In this manner, a substantially equal amount of cement may be deposited between the abutment body 232 and the interior surface of the through-hole 244 on all sides of the abutment body 232. Such a substantially equal distribution of cement provides a substantially evenly distributed mechanical attachment throughout the interface of the abutment body 232 and the interior surface of the through-hole 244.

The radial clearance of the through-hole 244 may be determined, for instance, using suitable CAD modeling software (e.g., the Ivoclar™ zirconia restoration platform) or other suitable technology. In the alternative or in addition, the radial clearance of the through-hole 244 may be determined through experimental testing using various abutment designs and sizes, abutment screw sizes, abutment hole sizes, and/or flared gingival opening circumferences/contours (e.g., a gradual v. immediate flare, a curved v. straight flare ("beveled"), various axial lengths, etc.).

The overall design of the dental bridge 200, including the tooth design, bite, abutment holes 230, etc., may be uniquely designed for each patient. The dental bridge 200 may be designed at least in part using a suitable restoration platform, such as the Ivoclar™ zirconia restoration platform. Generally, the restoration platform is used to scan, design, and produce a dental bridge suitable for a patient.

For instance, to design and create an upper jaw full teeth replacement dental bridge, the upper jaw may be scanned before atraumatic extractions are performed to create a replacement dental bridge that generally mimics the shape of the original teeth. Further, the lower jaw and teeth may be scanned to ensure that the upper jaw replacement bridge suitably overlaps/engages the patient's lower teeth (whether being replaced or retained).

The upper jaw may also be scanned after atraumatic extractions are performed to ensure that the "flare" of the replacement dental bridge substantially matches the flare of the implants (as measured with scan bodies secured to the implants). In that regard, the post-atraumatic extraction scan of the upper jaw may also be used to design the abutment holes of the bridge. For instance, the abutment holes may be designed to have substantially the same longitudinal axis as the scan bodies and/or the implants. Further, the abutment holes may be designed to have a suitable opening diameter/circumference for receiving the abutments (which may be comparable in size to the scan bodies or otherwise a known circumference). Finally, the abutment holes may be designed to have a suitable diameter, to provide a needed clearance needed for aligning the screws in the abutments/implants, as described above.

Figure 24:
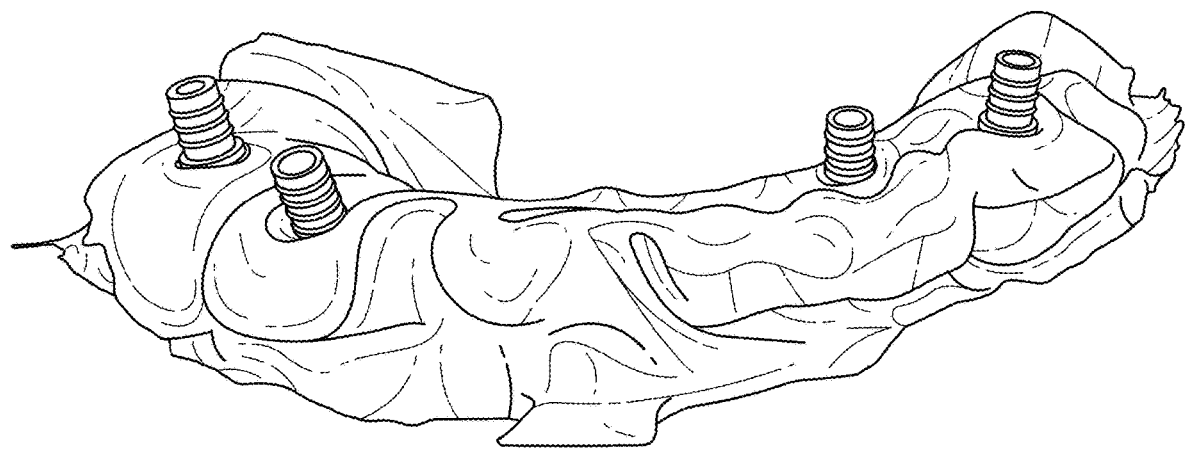
FIG. 24 depicts an intraoral scan image depicting an implant longitudinal axis (for instance, using scan bodies) for a lower jaw.
Figure 25:
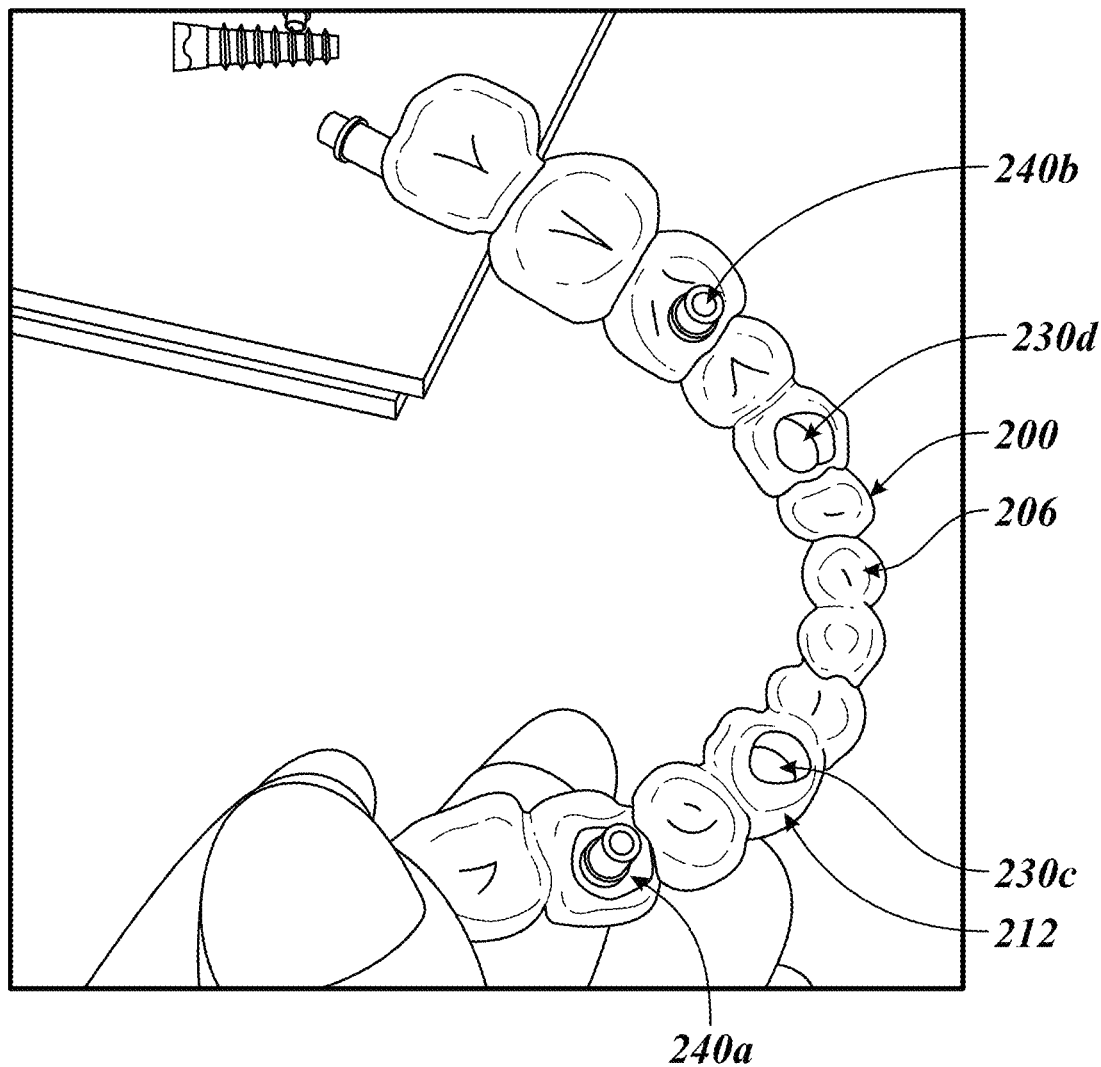
FIGS. 25-28 depict aspects of an exemplary method of installing a dental bridge formed in accordance with exemplary aspects of the present disclosure.
Figure 26:
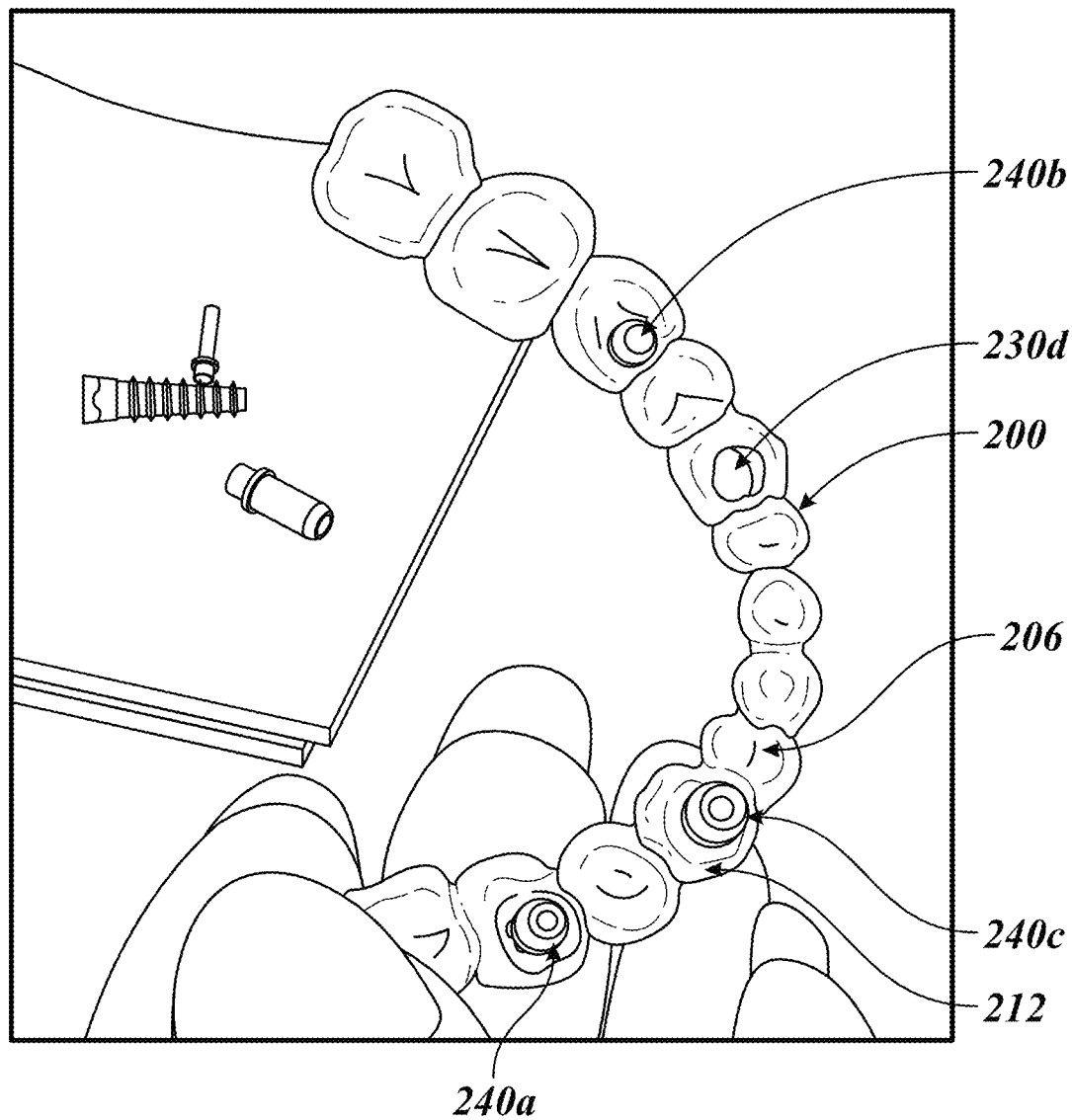

The scan data may be used to produce digital impressions that may be used to assess and modify the design of the bridge. For instance, FIG. 24 shows an intraoral scan depicting the abutment body longitudinal axis (for instance, using scan bodies) for a lower jaw. Actual impressions may also be created, as discussed above, at various stages of the pre-prosthetic ridge preservation process to aid in the bridge design. Once designed, the replacement bridge may be manufactured from zirconia or another suitable material using suitable milling/sintering techniques or the like (such as the using the milling machine and sintering furnace available from Ivoclar™). For instance, a final bridge may be custom milled from a solid piece of IPS e.max ZirCAD Prime ("Zirconia") with natural looking color shades that are absorbed into the bridge prior to furnace curing and final polishing. In that regard, the bridge may be formed from a homogenous material.

Exemplary Method of Installing a Dental Bridge

Referring to FIGS. 25-28, an exemplary method of installing the dental bridge 200 will now be described. The method is described as installing the dental bridge 200 in a patient's mouth, although for illustrative purposes, in some FIGS. the dental bridge 200 is shown as being installed on a 3D model created by an impression of a patient's mouth. Moreover, it should be appreciated that although the exemplary method is described as having a particular sequence of operations, the sequence may be altered without departing from the scope of the present disclosure. For example, some of the operations depicted may be performed in parallel or in a different sequence that does not materially affect the function of the method. In yet some examples, some of the steps of the method may be omitted. In yet some examples, additional steps not specifically discussed may be included. In other examples, different components of an example device or system may be used to implement the method.

In an initial step, the abutment holes of the dental bridge 200 and/or the corresponding abutments may be cleaned, abraded, etc. ("treated"), in preparation for securing abutments to the dental bridge 200. More specifically, the interior surface of each the abutment holes and/or the exterior surface of each the corresponding abutments may be cleaned, abraded, etc., to increase the respective bond strength to an adhesive material deposited between the abutment holes and the abutments.

As noted above with respect to FIGS. 20 and 23, an adhesive material such as cement may be deposited between the abutment body 232 of the abutment and the interior surface of the through-hole 244 of the abutment hole to define a mechanical attachment between the abutment and the abutment hole. If the abutment body 232 and the interior surface of the corresponding abutment through-hole 244 are cleaned, abraded, etc., prior to applying cement, the mechanical attachment between the abutment and the abutment hole is enhanced.

Each abutment body 232 and the interior surface of each abutment through-hole 244 may be cleaned, abraded, etc., using any suitable method. For instance, microairborne-particle abrasion, zirconia cleaning solutions, desiccating agent, hydrofluoric acid, alcohol, and/or rubber-rotary instruments may be used to clean the abutment body 232 and the interior surface of the corresponding abutment through-hole 244, e.g., the surface of the dental bridge 200 extending along the abutment through-holes 244. Each abutment body 232 and the interior surface of each corresponding abutment through-hole 244 may be cleaned, abraded, etc., on substantially all sides, e.g., substantially around their respective circumferences.

In addition or in the alternative, each abutment body 232 and the interior surface of each abutment through-hole 244 may be cleaned, abraded, etc., using a high-powered laser, such as the Waterlase iPlus all-tissue laser described herein. The water-energized laser beam can be directed at surfaces of the abutment body 232 and the abutment through-hole 244, and energy of the laser excites molecules in any surface contaminates and/or in material of the abutment or dental bridge, causing it to break up. The laser can create tiny little holes in the material surface, enhancing the ability of the material to bond to cement. In one example, the laser may be used in a "bond prep" configuration or setting for effectively cleaning, abrading, etc., the surfaces of the abutment body 232 and the abutment through-hole 244.

In a next step, an abutment may be placed inside each of the abutment holes. For instance, in the dental bridge 200 shown and described herein, first, second, third, and fourth abutments may be placed inside corresponding first, second, third, and fourth abutment holes. In the images shown in FIGS. 25 and 26, first and second abutments 240a and 240b are shown already received within corresponding first and second abutment holes 230a and 230b (such as in accordance with steps described below), and a third abutment 240c is shown being placed in a corresponding third abutment hole 230c.

The third abutment 240c is placed inside the corresponding third abutment hole 230c such that the abutment body extends into the through-hole of the abutment hole and the skirt of the abutment abuts rest against or at least somewhat within the gradually widened gingival opening (see FIG. 23). In this manner, the abutment skirt 234 is substantially flush with the gingival side 206 of the bridge 200. A fourth abutment (not shown) may be placed inside a corresponding fourth abutment hole 230d in a similar manner.

Various types of non-angulated abutments may be used with the dental bridge 200. For instance, one or more of the abutments may be engaging abutments (which generally include a post extending axially from the skirt that is configured to go about 3.5-4 mm down into the body of the implant), and one or more of the non-angulated abutments may be non-engaging abutments (which include a portion extending from the skirt that may go only about 1 mm down into the body of the implant). An engaging abutment may be used, for instance, if the implant collar is located deeper within the gum. In such an instance, an engaging abutment may be used to help access the implant. In other instances, an engaging implant may be used to help anchor the dental bridge 200 to the patient's jaw. With a portion of the abutment extending down into the implant, the engaging abutment can help define a mechanically strong, rigid connection between the bridge and the implant.

However, engaging abutments can be more difficult to align with the corresponding implant, especially in this instance where both the abutment and the implant extend along the tooth axis TA to accommodate the overall flare of the bridge 200. With the extended portion of the engaging abutment received within the body of the implant, the abutment may be moved laterally relative to the tooth axis TA very little if at all relative to the implant during alignment. In other words, the elongated axial interface between the extended post of the engaging abutment and the implant substantially prevents any lateral movement of the engaging abutment relative to the implant.

In that regard, in an example using four abutments, all four abutments may be non-engaging abutments to allow for ease of installation and removal of the bridge 200. The American Academy of Prosthodontics requires that a prosthetic, such as the bridge 200, be removable for repairs or cleaning. Accordingly, by using only non-engaging abutments, the bridge 200 may be easily removed and re-installed for cleaning, repairs, maintenance, etc.

In other examples, one engaging abutment may be used with three non-engaging abutments to provide both mechanical strength and some flexibility during installation. For instance, the first abutment 240a shown in FIG. 26 may be an engaging abutment, and the second, third, and fourth abutments 240b, 240c, and 240d may be non-engaging abutments. In this manner, the first engaging abutment 240a may enhance the mechanical connection between the bridge and the implant, whereas the non-engaging abutments 240b, 240c, and 204d provide the adjustability needed during installation (e.g., the non-engaging abutments 240b, 240c, and 204d can move sufficiently laterally relative to the tooth axis TA for alignment and threading of the abutment screws into the implants).

It should be appreciated that in general, a suitable number of engaging and non-engaging abutments are used to ensure sufficient mechanical connection of the bridge to the implants while supporting ease of bridge installation. In most instances, where four abutments are used for bridge installation, all four abutments are non-engaging abutments. Using all non-engaging abutments provides for ease of installation and removal of the bridge while providing a suitable mechanical connection between the bridge and the implants (through the abutments).

In one example, the abutments may be non-platform switching abutments. As is known in the art, platform switching abutments have an implant-engaging portion that is smaller in diameter than the implant platform. In that regard, platform switching abutments may be used in situations to help prevent crestal bone loss and/or to increase the volume of soft tissue surrounding the implant platform, such as with a single tooth replacement. With an abutment having an implant-engaging portion smaller in diameter than the implant platform, gingiva will grow into the space surrounding the smaller diameter portion. Such gingiva growth can compromise the sealing interface between the dental bridge 200 and the gingiva. Accordingly, the inventor has found that non-platform switching abutments, which allow for a substantially smooth transition from the implant to the abutment and which prevent substantial gingiva overgrowth in that area, are generally preferred.

Figure 27:
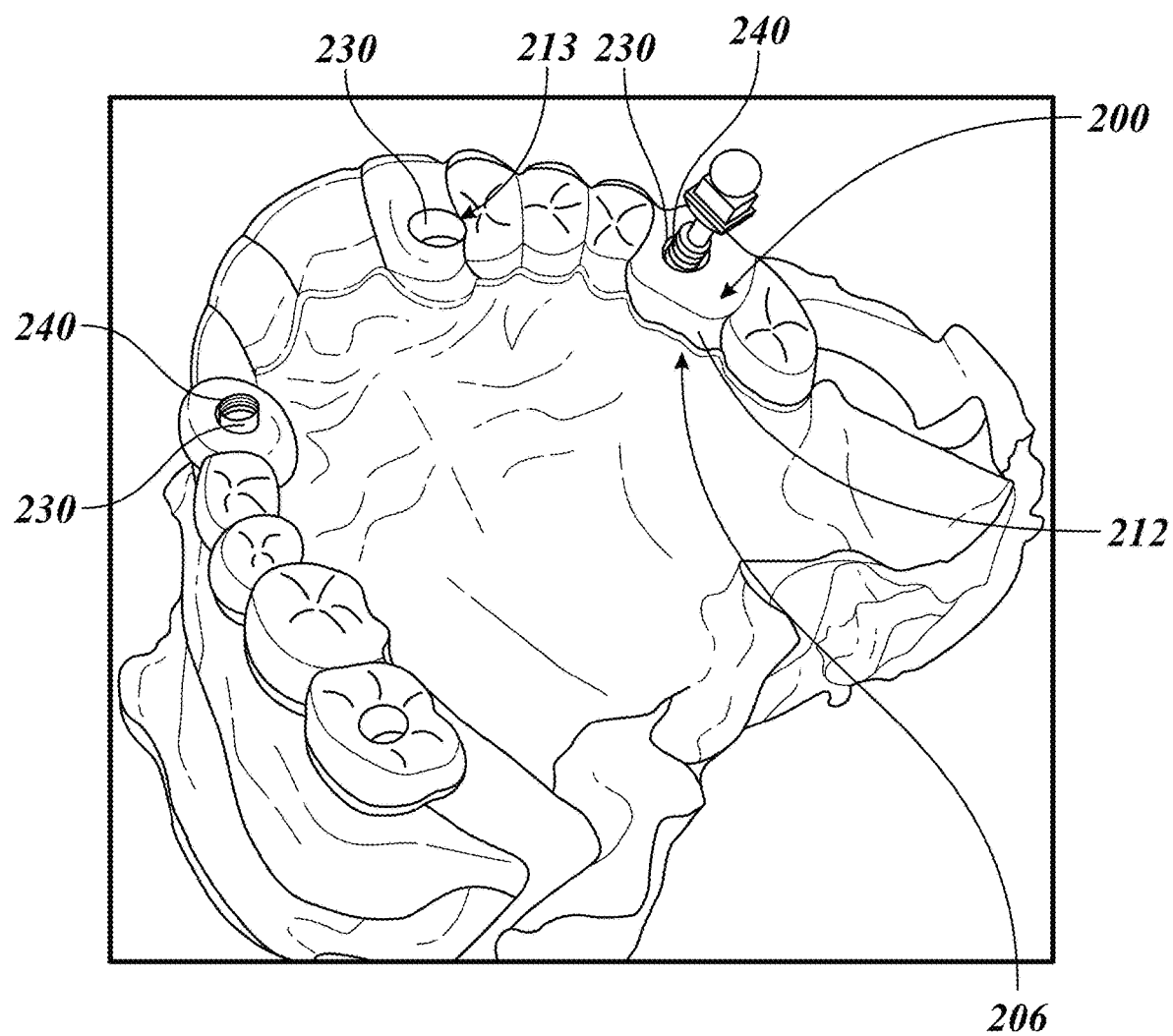

In a next step, generally shown in FIG. 27, the dental bridge 200 may be placed into the patient's mouth. More specifically, the ovate pontic portion on the gingival side 206 of the dental bridge 200 is seated or otherwise sealed against the correspondingly-shaped bony/gingival ridge of the patient. Once properly seated/sealed, abutment screws may be placed into each of the abutments 240 and aligned with the threaded openings in the implants. The abutment screws may then be screwed down into the underlying implants (see a screwdriver being used to align and/or apply torque to a screw received in abutment 240).

Figure 28:
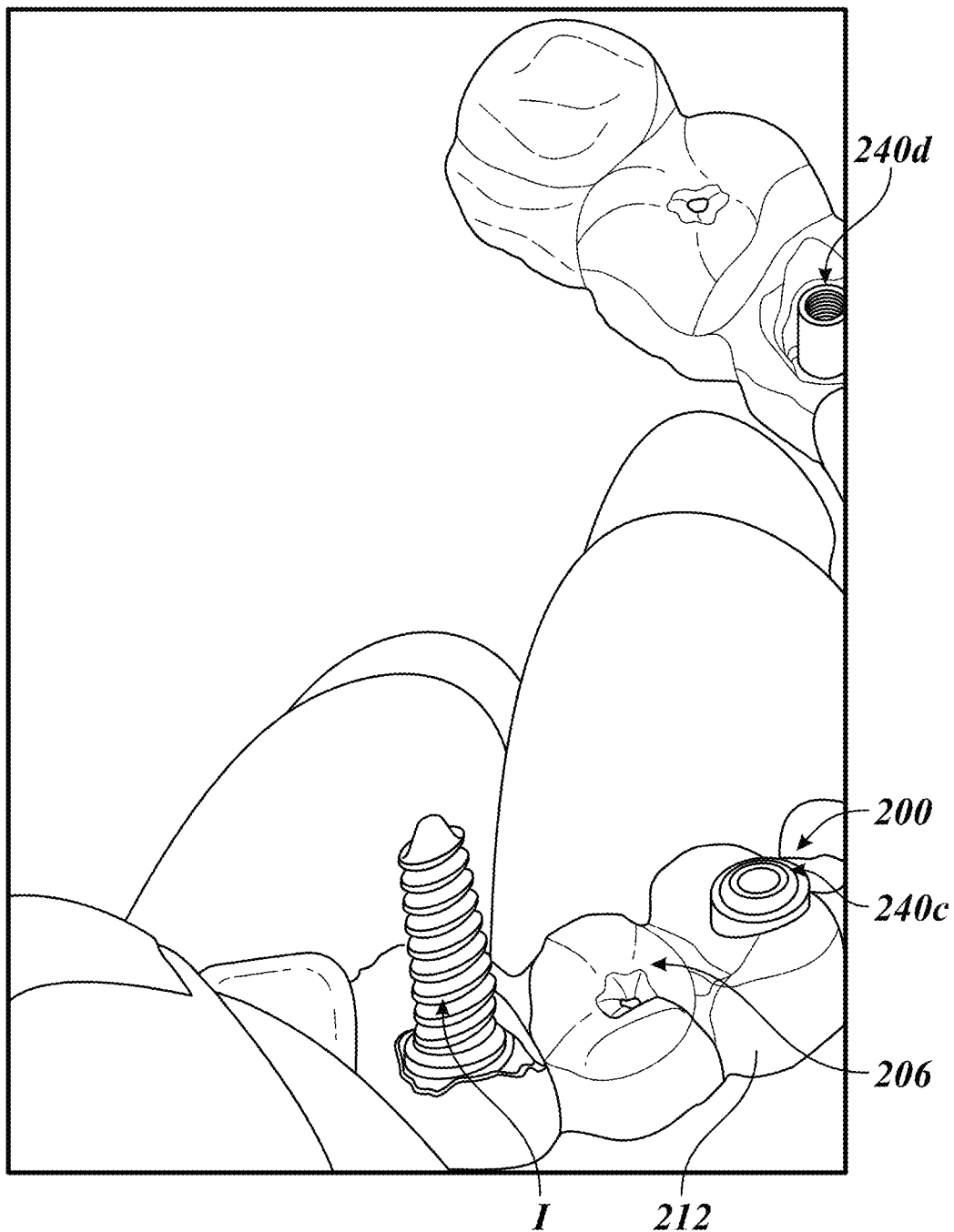

For instance, the abutment screws may be inserted into substantially aligned through-holes of the abutments and the implants, and the screws may be held in position magnetically or otherwise by a small screwdriver. The abutments may then be tightened down into the implants, at least partially, with the abutment screws. If four abutments are used, the first, second, third, and fourth abutments 240 may be screwed into the corresponding implants either in parallel or in series. FIG. 28 shows an implant seated against an abutment secured in an abutment hole of the bridge.

With the bridge 200 seated/sealed against the bony/gingival ridge of the patient and with the abutments 240 at least partially secured to the implants, the abutments are generally located within the bridge in the final position. As such, a dental professional can add/clean/cure cement at the base of the dental bridge 200 (on the gingival side) at the intersection of the abutment holes/abutments to secure the abutments within the bridge in their substantially "final" location. Once cured, the abutment screws can be unscrewed, and the dental bridge 200 can be removed from the implants (e.g., it can be disengaged from the bony/gingival ridge). With dental bridge 200 removed, any additional excess cement can be cleaned off the base of the bridge and it can be cured (e.g., light cured) to fully secure the abutments to the bridge at the base. By adding/cleaning/curing/cleaning/curing cement in this manner, any excess cement underneath the dental bridge 200, which would irritate the tissue, is minimized.

The dental bridge 200 may then be put back into the patient's mouth such that the bridge is seated/sealed against the bony/gingival ridge of the patient and the abutments engage the implants. Thereafter, all the abutment screws may be inserted into the through-holes of the abutments and implants (either in parallel or in series), and the abutment screws may be fully screwed into the implants with sufficient torque, such as about 15 Ncm. The doctor can then add/clean/cure cement at the top (incisal/occlusal) side of the dental bridge 200 at the intersection of the occlusal/incisal portion of the abutment holes and the abutments after, for instance, adding a layer of cotton balls or pellets into the abutment holes from the occlusal side. The cotton pellets or similar help prevent cement from covering the abutment screw head. As such, the screw heads remain accessible (after drilling through the cement) for any bridge maintenance or cleaning. After the cotton pellets are placed, cement may be added to the abutment holes from the occlusal side and light cured. The cement may be added/cleaned in a manner such that it is substantially flush with the occlusal side of the bridge. The cement may also be substantially tooth colored to match the tooth portion of the bridge.

The dental bridge 200 formed in accordance herein, when installed in the manner described above or in a similar manner, is superiorly hygienic to prior art full mouth dental restoration devices in that there are no undercuts or hidden areas of food entrapment. Rather, the ovate shape of the dental bridge 200 seats against the natural bony/gingival ridge of the patient to seal against the gums in a manner similar to a natural tooth, a single replacement tooth, a partial bridge, a crown, etc. The natural teeth look and feel of the dental bridge 200 allows for easy cleaning of the bridge, both by a toothbrush/floss and by self-cleansing via normal, un-obstructed salivary flow, whereby saliva moves naturally across the bridge removing and flushing away any plaque or food debris.

Exemplary Overview of the Dental Restoration Method

Referring to FIGS. 29A-29F, an exemplary method of performing a full mouth dental restoration will now be described. The method generally includes performing a full arch dental restoration device arch preparation system and method, as described herein. As noted above, the full arch dental restoration device arch preparation system and method may incorporate aspects of a preliminary bridge design process, a pre-prosthetic ridge preservation process including performing atraumatic dental extractions and preserving the original tooth sockets to prepare a patient's mouth for bridge placement, and a design and use of a surgical guide configured to aid in implant placement. Regardless of whether a surgical guide is used, the method may include placing socket sized, non-angulated implants into the preserved tooth sockets. The method may further generally include creating and installing a uniquely designed dental bridge on the upper and/or lower jaw that is configured to mate with the preserved tooth sockets and the socket sized, non-angulated implants. The method may be carried out using some or all of the aspects described above with respect to FIGS. 8-28.

It should be appreciated that although the example method is described as having a particular sequence of operations, the sequence may be altered without departing from the scope of the present disclosure. For example, some of the operations depicted may be performed in parallel or in a different sequence that does not materially affect the function of the method. In yet some examples, some of the steps of the method may be omitted. In yet some examples, additional steps not specifically discussed may be included. In other examples, different components of an example device or system may be used to implement the method.

Figure 29A:
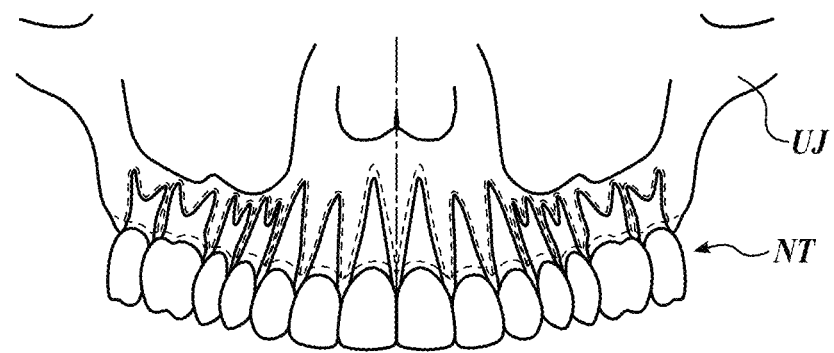
FIG. 29A depicts an upper jaw having a full mouth of teeth, e.g., fourteen teeth.

FIG. 29A depicts an upper jaw UJ having a full mouth of natural teeth NT, e.g., fourteen teeth. In that regard, the method will be described with regard to a dental restoration of all the teeth (e.g., ten, twelve, or fourteen teeth) of an upper jaw, although it should be appreciated that a similar method may be used for the lower jaw.

In one step, a patient may be evaluated and selected as a candidate for a full mouth, upper jaw dental restoration, such as using information gathered from a physical exam, a CBCT scan, an intraoral scan, etc. Aspects of the evaluation may include reviewing any pathologies of the teeth NT or other aspects of the teeth that may require special attention during atraumatic extraction (e.g., a hooked root tip), as discussed above.

In another step, a preliminary bridge design process may be performed. The preliminary bridge design process may include using foresight, such as with visualization of a final bridge design and/or visualization of bridge design steps, to determine a strategy for performing at least one of the pre-prosthetic ridge preservation process and a design and use of a surgical guide.

Figure 29B:
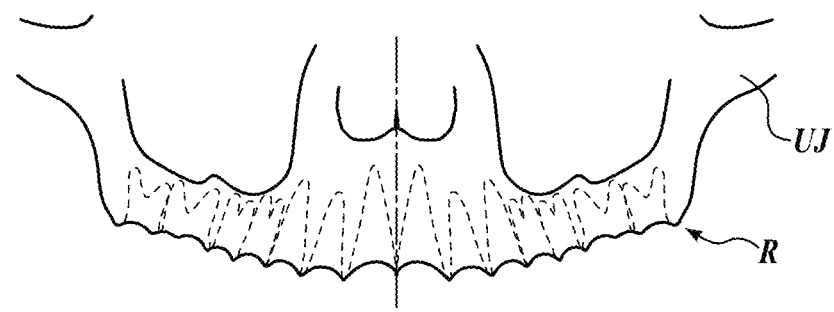
FIG. 29B depicts an upper jaw having a full mouth of teeth, e.g., fourteen teeth, atraumatically extracted with the tooth sockets preserved in accordance with exemplary aspects of the pre-prosthetic ridge preservation process of FIG. 9.

In another step, aspects of the pre-prosthetic ridge preservation process may be performed. The pre-prosthetic ridge preservation process may include atraumatically extracting some or all of the teeth using the techniques described herein, or similar techniques. FIG. 29B shows all of the teeth NT extracted. The teeth are extracted atraumatically such that the alveolar bone surrounding each tooth socket S is preserved substantially in its entirety, along with the keratinized gingiva that defines the naturally shaped gingival ridge R. Further, apical pressure may be applied during extraction to condense the apical part of the alveolar bone, providing the foundation for bi-cortical anchorage of the implant.

Figure 29C:
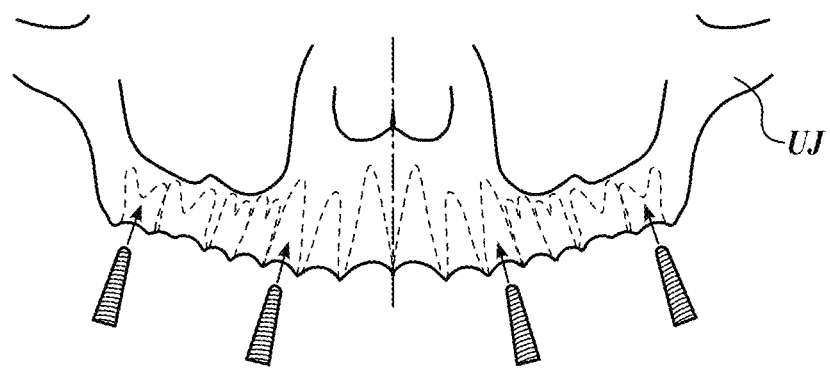
FIG. 29C depicts implants being placed in tooth sockets of the upper jaw of FIG. 29B.
Figure 29D:
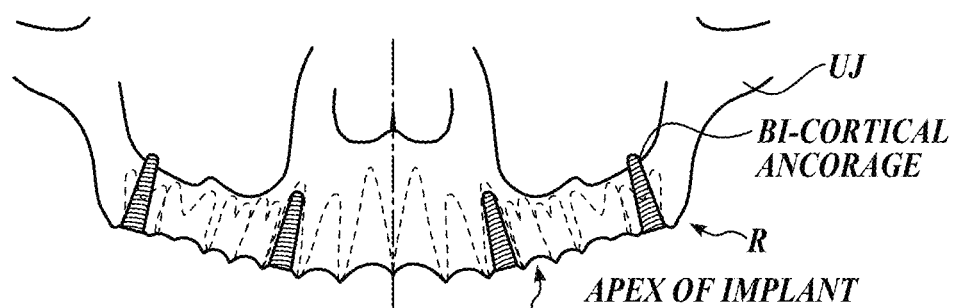
FIG. 29D depicts implants placed in tooth sockets of the upper jaw of FIG. 29B.

In that regard, in other steps, as shown in FIGS. 29C and 29D, socket sized, non-angulated implants I are placed into preserved tooth sockets S, as discussed above. For instance, the implants may be placed in sockets for former teeth #3 (upper right first molar), #6 (upper right canine), #11 (upper left canine), and #14 (upper left first molar), unless there is insufficient bone in which case the implant can be moved one tooth socket or an additional implant can be placed in a nearby socket.

The implants may be placed into the former tooth sockets (root sockets) either free handed or with the aid of a surgical guide. Generally, each of the implants I is placed into a corresponding socket S such that a longitudinal axis of the implant is substantially coaxially aligned with a longitudinal axis of the corresponding tooth socket S (defined by the original tooth having a tooth axis TA), as shown in FIGS. 16A-17C. As noted above, the condensed apical part of the alveolar bone (see, e.g., condensed bone CB shown in FIG. 16A), which is hard and thick, can be used for bi-cortical anchorage of the implant, as shown for implant 110a in FIG. 16A. Moreover, the implant may be placed such that the threads of the implant are generally located in the bone, and the collar of the implant is generally disposed above the bone (such as at least partially in the gingival layer), as shown in FIGS. 17A-17C.

Figure 29E:
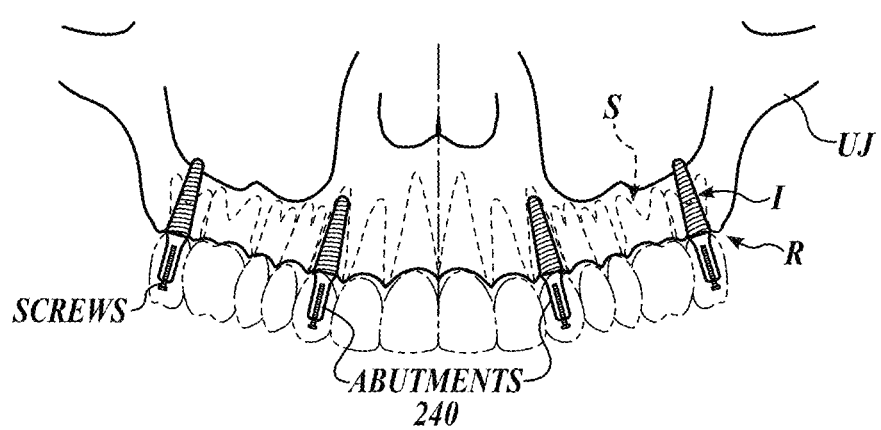
FIG. 29E depicts a dental bridge formed in accordance with exemplary aspects of the present disclosure being secured to the implants of the upper jaw of FIG. 29D, wherein abutments received within the dental bridge are being secured to implants.
Figure 29F:
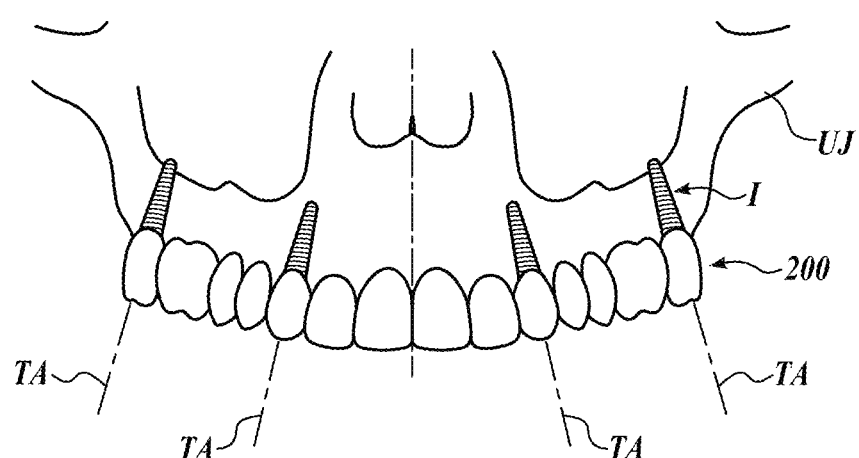
FIG. 29F depicts a dental bridge formed in accordance with exemplary aspects of the present disclosure secured to the implants of the upper jaw of FIG. 29D.

In another step, as shown in FIG. 29E, the abutments 240 may be located within the abutment holes 230 of the dental bridge 200, and abutment screws may be used to at least partially secure the abutments to the implants I. The abutments 240 may then be at least partially secured to the gingival side of the bridge 200 with cement or the like, and the bridge may be removed (by unscrewing the screws) for cleaning and fully securing the abutments to the bridge at the gingival base. The dental bridge 200 may then be put back into the patient's mouth and the abutment screws may be fully screwed into the implants with sufficient torque, substantially completing the dental restoration process, as shown in FIG. 29F.

Figure 30:
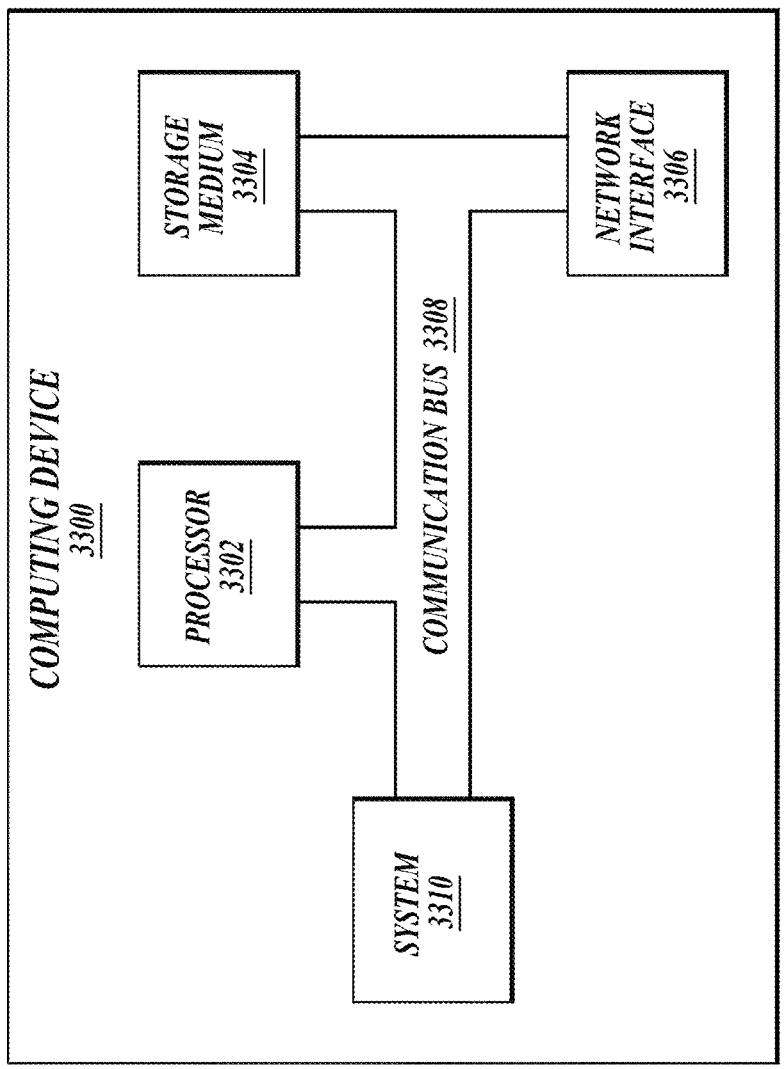
FIG. 30 shows a block diagram that illustrates a non-limiting example embodiment of a computing device appropriate for use as a computing device with embodiments of the present disclosure.

FIG. 30 is a block diagram that illustrates aspects of an exemplary computing device 3000 appropriate for use as a computing device of the present disclosure. While multiple different types of computing devices were discussed above, the exemplary computing device 3000 describes various elements that are common to many different types of computing devices. While FIG. 30 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Some embodiments of a computing device may be implemented in or may include an application-specific integrated circuit (ASIC), a field-programmable gate array (FPGA), or other customized device. Moreover, those of ordinary skill in the art and others will recognize that the computing device 3000 may be any one of any number of currently available or yet to be developed devices.

In its most basic configuration, the computing device 3000 includes at least one processor 3002 and a system memory 3010 connected by a communication bus 3008. Depending on the exact configuration and type of device, the system memory 3010 may be volatile or nonvolatile memory, such as read only memory ("ROM"), random access memory ("RAM"), EEPROM, flash memory, or similar memory technology. Those of ordinary skill in the art and others will recognize that system memory 3010 typically stores data and/or program modules that are immediately accessible to and/or currently being operated on by the processor 3002. In this regard, the processor 3002 may serve as a computational center of the computing device 3000 by supporting the execution of instructions.

As further illustrated in FIG. 30, the computing device 3000 may include a network interface 3006 comprising one or more components for communicating with other devices over a network. Embodiments of the present disclosure may access basic services that utilize the network interface 3006 to perform communications using common network protocols. The network interface 3006 may also include a wireless network interface configured to communicate via one or more wireless communication protocols, such as Wi-Fi, 2G, 3G, LTE, WiMAX, Bluetooth, Bluetooth low energy, and/or the like. As will be appreciated by one of ordinary skill in the art, the network interface 3006 illustrated in FIG. 30 may represent one or more wireless interfaces or physical communication interfaces described and illustrated above with respect to particular components of the computing device 3000.

In the exemplary embodiment depicted in FIG. 30, the computing device 3000 also includes a storage medium 3004. However, services may be accessed using a computing device that does not include means for persisting data to a local storage medium. Therefore, the storage medium 3004 depicted in FIG. 30 is represented with a dashed line to indicate that the storage medium 3004 is optional. In any event, the storage medium 3004 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

Suitable implementations of computing devices that include a processor 3002, system memory 3010, communication bus 3008, storage medium 3004, and network interface 3006 are known and commercially available. For ease of illustration and because it is not important for an understanding of the claimed subject matter, FIG. 30 does not show some of the typical components of many computing devices. In this regard, the computing device 3000 may include input devices, such as a keyboard, keypad, mouse, microphone, touch input device, touch screen, tablet, and/or the like. Such input devices may be coupled to the computing device 3000 by wired or wireless connections including RF, infrared, serial, parallel, Bluetooth, Bluetooth low energy, USB, or other suitable connections protocols using wireless or physical connections. Similarly, the computing device 3000 may also include output devices such as a display, speakers, printer, etc. Since these devices are well known in the art, they are not illustrated or described further herein.

Numerous specific details are described to provide a thorough understanding of the disclosure. However, in certain instances, well-known or conventional details are not described in order to avoid obscuring the description. Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

While the concepts of the present disclosure are susceptible to various modifications and alternative forms, specific examples thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Although the example method is described as having a particular sequence of operations, the sequence may be altered without departing from the scope of the present disclosure. For example, some of the operations depicted may be performed in parallel or in a different sequence that does not materially affect the function of the method. In yet some examples, some of the steps of the method may be omitted. In other examples, different components of an example device or system may be used to implement the method.

References in the specification to "one example," "an example," "an illustrative example," etc., indicate that the example described may include a particular feature, structure, or characteristic, but every example may or may not necessarily include that particular feature, structure, or characteristic. Moreover, such phrases are not necessarily referring to the same example. Further, when a particular feature, structure, or characteristic is described in connection with an example, it is submitted that it is within the knowledge of one skilled in the art to affect such feature, structure, or characteristic in connection with other examples whether or not explicitly described.

As used herein, the terms "about" and "approximately," in reference to a number, is used herein to include numbers that fall within a range of 10%, 5%, or 1% in either direction (greater than or less than) the number unless otherwise stated or otherwise evident from the context (except where such number would exceed 100% of a possible value).

Language such as "top", "bottom", "upper", "lower", "vertical", "horizontal", "lateral", etc., in the present disclosure is meant to provide orientation for the reader with reference to the drawings and is not intended to be the required orientation of the components or to impart orientation limitations into the claims.

In the drawings, some structural or method features may be shown in specific arrangements and/or orderings. However, it should be appreciated that such specific arrangements and/or orderings may not be required. Rather, in some examples, such features may be arranged in a different manner and/or order than shown in the illustrative figures. Additionally, the inclusion of a structural or method feature in a particular figure is not meant to imply that such feature is required in all examples and, in some examples, it may not be included or may be combined with other features.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term.

Likewise, the disclosure is not limited to various example examples given in this specification. Unless otherwise defined, technical and scientific terms used herein have the meaning as commonly understood by one of ordinary skill in the art to which this disclosure pertains. In the case of conflict, the present document, including definitions will control.

Note that titles or subtitles may be used in the disclosure for convenience of a reader, which in no way should limit the scope of the disclosure.

While illustrative examples have been illustrated and described, it will be appreciated that various changes can be made therein without departing from the spirit and scope of the disclosure.

The examples of the invention in which an exclusive property or privilege is claimed are defined as follows:

1. A dental restoration device arch preparation method for replacing a full arch with a teeth-only, gingiva-free, full-arch dental restoration device having a plurality of integrally formed teeth portions and first, second, third, and fourth abutment holes, each abutment hole having a longitudinal axis that is substantially coaxially aligned with a tooth axis of a corresponding tooth portion of the plurality of integrally formed teeth portions and a tooth socket axis of a corresponding post-extraction tooth socket when the corresponding tooth portion is engaged with the corresponding post-extraction tooth socket, comprising:

performing, with a computing device, a tooth socket implant locating step including determining, based on a digital representation of a patient's replacement arch, first, second, third, and fourth tooth sockets of the patient's replacement arch that are intended locations of first, second, third, and fourth straight implants, respectively, for securing a teeth-only, gingiva-free, full-arch dental restoration device to the patient's replacement arch after all original teeth of the patient's replacement arch are extracted, wherein each of the replacement arch tooth sockets designated as intended locations of straight implants are adjacent to a replacement arch tooth socket that is not designated as an intended location of a straight implant;

extracting any teeth in the first, second, third, and fourth tooth sockets of the patient's replacement arch, wherein each tooth is extracted in a manner that substantially maintains the original alveolar bone and original keratinized gingiva of the patient's replacement arch;

placing a body of a surgical guide against at least one of teeth remaining in the patient's replacement arch and against gums of the patient's replacement arch such that first, second, third, and fourth surgical guide sleeves located in the body of the surgical guide are aligned with the first, second, third, and fourth tooth sockets of the patient's replacement arch, wherein each of the surgical guide sleeves is an elongated cylindrical shape and has a center longitudinal axis that is substantially aligned with an axis of the corresponding tooth socket when the surgical guide body is mated with the at least one of teeth and gums of a patient's replacement arch;

inserting the first, second, third, and fourth straight implants into the first, second, third, and fourth surgical guide sleeves;

placing each of the first, second, third, and fourth straight implants into the first, second, third, and fourth tooth sockets of the patient's replacement arch, respectively, with a surgical implant tool such that a longitudinal axis of each straight implant is substantially aligned with an axis of the corresponding tooth socket, wherein when placing each of the first, second, third, and fourth straight implants into the first, second, third, and fourth tooth sockets of the patient's replacement arch, respectively, a portion of the surgical implant tool engages a depth limiting feature of the surgical guide such that when the straight implant is placed in the corresponding tooth socket, a collar of each straight implant is generally above an outer cortex layer of bone at least partially in a gingiva layer of the corresponding tooth socket; and extracting any remaining teeth of the patient's replacement arch in a manner that substantially maintains the patient's original alveolar bone and original keratinized gingiva of the patient's replacement arch.

2. The method of claim 1, further comprising making a surgical guide by:
  performing, with a computing device, a virtual implant placement step including digitally placing each of the first, second, third, and fourth straight implants in a digital representation of the patient's replacement arch;
  performing, with a computing device, a surgical guide design step including digitally defining a size and shape of the body of the surgical guide relative to a digital representation of the patient' replacement arch; and
  outputting, with a computing device, fabrication instructions to a fabrication machine for making a surgical guide based on the surgical guide digital design.

3. The method of claim 1, wherein the tooth socket implant locating step includes determining which of a patient's replacement arch tooth sockets are intended locations of straight implants by confirming at least one of a tooth root socket is disease free, all four walls of a tooth root socket are substantially intact, and a tooth root socket is a sufficient distance from a sinus cavity and an inferior alveolar nerve.

4. The method of claim 1, further comprising performing, with a computing device, a preliminary bridge design process to determine at least one of a preliminary socket designation for straight implant placement, surgical guide use strategy, surgical guide design, and teeth extraction and ridge preservation strategy.

5. The method of claim 1, further comprising extracting only teeth in the first, second, third, and fourth tooth sockets of the patient's replacement arch before the step of placing each of the first, second, third, and fourth straight implants into the first, second, third, and fourth tooth sockets of the patient's replacement arch, respectively.

6. The method of claim 1, further comprising designating, with a computing device, replacement arch tooth sockets as intended locations of straight implants adjacent to a replacement arch tooth socket that is not an intended location of an implant.

* * * * *